United States Patent
Haque et al.

(10) Patent No.: US 12,019,155 B2
(45) Date of Patent: Jun. 25, 2024

(54) ULTRASONIC IMAGING DEVICE WITH PROGRAMMABLE ANATOMY AND FLOW IMAGING

(71) Applicant: EXO IMAGING, INC., Redwood City, CA (US)

(72) Inventors: Yusuf Haque, Woodside, CA (US); Sandeep Akkaraju, Wellesley, MA (US); Janusz Bryzek, Oakland, CA (US); Brian Bircumshaw, Oakland, CA (US)

(73) Assignee: Exo Imaging, Inc., Santa Clara, CA (US)

( * ) Notice: Subject to any disclaimer, the term of this patent is extended or adjusted under 35 U.S.C. 154(b) by 4 days.

(21) Appl. No.: 17/522,206

(22) Filed: Nov. 9, 2021

(65) Prior Publication Data

US 2022/0066026 A1    Mar. 3, 2022

Related U.S. Application Data

(63) Continuation of application No. 17/153,631, filed on Jan. 20, 2021, now Pat. No. 11,199,623.
(Continued)

(51) Int. Cl.
*G01S 15/89* (2006.01)
*A61B 8/00* (2006.01)
(Continued)

(52) U.S. Cl.
CPC ............ *G01S 15/89* (2013.01); *A61B 8/4427* (2013.01); *A61B 8/4488* (2013.01);
(Continued)

(58) Field of Classification Search
CPC .. G01S 15/89; G01S 15/8925; G01S 15/8988; G01S 7/5208; G10K 11/34;
(Continued)

(56) References Cited

U.S. PATENT DOCUMENTS

| | | |
|---|---|---|
| 4,211,949 A | 7/1980 | Brisken et al. |
| 4,236,137 A | 11/1980 | Kurtz et al. |

(Continued)

FOREIGN PATENT DOCUMENTS

| | | |
|---|---|---|
| CN | 1677706 A | 10/2005 |
| CN | 103842841 A | 6/2014 |

(Continued)

OTHER PUBLICATIONS

APC International, Ceramic manufacturing series—poling PZT ceramics. https://www.americanpiezo.com/blog/ceramic-manufacturing-series-poling-pzt-ceramics/ [1-3] (2016).
(Continued)

*Primary Examiner* — David L Singer
(74) *Attorney, Agent, or Firm* — Morgan, Lewis & Bockius LLP

(57) ABSTRACT

An imaging device includes a transducer that includes an array of piezoelectric elements formed on a substrate. Each piezoelectric element includes at least one membrane suspended from the substrate, at least one bottom electrode disposed on the membrane, at least one piezoelectric layer disposed on the bottom electrode, and at least one top electrode disposed on the at least one piezoelectric layer. Adjacent piezoelectric elements are configured to be isolated acoustically from each other. The device is utilized to measure flow or flow along with imaging anatomy.

18 Claims, 37 Drawing Sheets

Related U.S. Application Data

(60) Provisional application No. 62/985,574, filed on Mar. 5, 2020.

(51) Int. Cl.

| | | |
|---|---|---|
| *B06B 1/06* | (2006.01) | |
| *B81B 3/00* | (2006.01) | |
| *G01N 29/06* | (2006.01) | |
| *G01N 29/24* | (2006.01) | |
| *G01N 29/26* | (2006.01) | |
| *G01N 29/34* | (2006.01) | |
| *G01S 7/52* | (2006.01) | |
| *G10K 11/34* | (2006.01) | |
| *H10N 30/20* | (2023.01) | |
| *A61B 8/08* | (2006.01) | |
| *G01N 29/02* | (2006.01) | |
| *G01N 29/04* | (2006.01) | |

(52) U.S. Cl.
CPC .......... *A61B 8/4494* (2013.01); *B06B 1/0622* (2013.01); *B81B 3/0021* (2013.01); *G01N 29/2437* (2013.01); *G01N 29/2456* (2013.01); *G01N 29/262* (2013.01); *G01N 29/343* (2013.01); *G01N 29/345* (2013.01); *G01S 7/5208* (2013.01); *G01S 15/8925* (2013.01); *G01S 15/8988* (2013.01); *G10K 11/34* (2013.01); *H10N 30/2047* (2023.02); *A61B 8/0883* (2013.01); *A61B 8/4472* (2013.01); *A61B 8/483* (2013.01); *A61B 8/488* (2013.01); *A61B 8/546* (2013.01); *B06B 2201/76* (2013.01); *G01N 29/02* (2013.01); *G01N 29/04* (2013.01); *G01N 29/0654* (2013.01); *G01N 2291/017* (2013.01); *G01N 2291/02466* (2013.01); *G01N 2291/02475* (2013.01); *G01N 2291/02836* (2013.01); *G01N 2291/0289* (2013.01); *G01N 2291/044* (2013.01); *G01N 2291/106* (2013.01)

(58) Field of Classification Search
CPC .. G01N 29/343; G01N 29/345; G01N 29/262; G01N 29/2437; G01N 29/2456; G01N 29/0654; G01N 29/04; G01N 29/02; G01N 2291/106; G01N 2291/017; G01N 2291/0289; G01N 2291/044; G01N 2291/02466; G01N 2291/02475; G01N 2291/02836; G01N 29/2406; B81B 3/0021; B06B 1/0622; B06B 2201/76; A61B 8/4427; A61B 8/4488; A61B 8/4494; A61B 8/488; A61B 8/4472; A61B 8/483; A61B 8/546; A61B 8/0883; H01L 41/0973

See application file for complete search history.

(56) References Cited

U.S. PATENT DOCUMENTS

| | | |
|---|---|---|
| 4,281,298 A | 7/1981 | Gounji et al. |
| 4,375,042 A | 2/1983 | Marcus |
| 4,731,865 A | 3/1988 | Sievenpiper |
| 5,160,870 A | 11/1992 | Carson |
| 5,230,340 A | 7/1993 | Rhyne |
| 5,520,187 A | 5/1996 | Snyder |
| 5,605,154 A | 2/1997 | Ries et al. |
| 5,763,785 A * | 6/1998 | Chiang ............... G10K 11/346 73/609 |
| 5,906,580 A | 5/1999 | Kline-Schoder |
| 5,957,846 A | 9/1999 | Chiang |
| 5,969,621 A | 10/1999 | Getman et al. |
| 6,023,977 A | 2/2000 | Langdon et al. |
| 6,083,168 A | 7/2000 | Hossack et al. |
| 6,108,121 A | 8/2000 | Mansell et al. |
| 6,359,367 B1 | 3/2002 | Sumanaweera et al. |
| 6,542,846 B1 | 4/2003 | Miller |
| 7,005,776 B1 | 2/2006 | Iino et al. |
| 7,532,093 B1 | 5/2009 | Pulskamp et al. |
| 8,004,158 B2 | 8/2011 | Hielscher |
| 8,182,428 B2 | 5/2012 | Angelsen et al. |
| 9,067,779 B1 | 6/2015 | Rothberg et al. |
| 10,835,209 B2 | 11/2020 | Haque et al. |
| 2001/0005776 A1 | 6/2001 | Holley et al. |
| 2003/0178914 A1 | 9/2003 | Ogawa et al. |
| 2003/0181814 A1 | 9/2003 | Ji et al. |
| 2004/0085858 A1 | 5/2004 | Khuri-Yakub et al. |
| 2004/0190377 A1 | 9/2004 | Lewandowski |
| 2004/0195937 A1 | 10/2004 | Matsubara et al. |
| 2005/0025377 A1 | 2/2005 | Avinash et al. |
| 2005/0228282 A1 | 10/2005 | Wang et al. |
| 2005/0228284 A1 | 10/2005 | Baumgartner |
| 2006/0113866 A1 | 6/2006 | Ganor |
| 2006/0122486 A1 | 6/2006 | Tamez-Pena et al. |
| 2006/0173313 A1 | 8/2006 | Liu et al. |
| 2007/0120896 A1 | 5/2007 | Stephens et al. |
| 2007/0167752 A1 | 7/2007 | Proulx et al. |
| 2008/0194053 A1 | 8/2008 | Huang |
| 2008/0255451 A1 | 10/2008 | Cohen et al. |
| 2009/0001853 A1 | 1/2009 | Adachi et al. |
| 2009/0069686 A1 | 3/2009 | Daft |
| 2009/0140609 A1 | 6/2009 | Huang |
| 2009/0182237 A1* | 7/2009 | Angelsen ............... B06B 1/064 600/459 |
| 2010/0020645 A1 | 1/2010 | Wodnicki et al. |
| 2010/0168583 A1 | 7/2010 | Dausch et al. |
| 2010/0266186 A1 | 10/2010 | Hebrank et al. |
| 2010/0324423 A1* | 12/2010 | El-Aklouk ............ A61B 8/4488 600/444 |
| 2011/0051461 A1 | 3/2011 | Buchwald et al. |
| 2011/0115333 A1 | 5/2011 | Ezaki |
| 2011/0115337 A1 | 5/2011 | Nakamura et al. |
| 2011/0120971 A1 | 5/2011 | Martin |
| 2011/0218594 A1 | 9/2011 | Doron et al. |
| 2011/0249878 A1 | 10/2011 | Pagoulatos et al. |
| 2012/0068571 A1 | 3/2012 | Chen |
| 2012/0116220 A1 | 5/2012 | Burcher et al. |
| 2012/0127136 A1 | 5/2012 | Schneider et al. |
| 2012/0146642 A1 | 6/2012 | Du |
| 2012/0238880 A1 | 9/2012 | Davidsen |
| 2012/0319535 A1 | 12/2012 | Dausch |
| 2013/0206962 A1 | 8/2013 | Barr |
| 2013/0303919 A1 | 11/2013 | Corl |
| 2014/0024928 A1 | 1/2014 | Boctor et al. |
| 2014/0035735 A1 | 2/2014 | Zellers et al. |
| 2014/0117812 A1 | 5/2014 | Hajati |
| 2014/0155747 A1 | 6/2014 | Bennett et al. |
| 2014/0184023 A1 | 7/2014 | Rice et al. |
| 2014/0184027 A1 | 7/2014 | Rice |
| 2014/0219063 A1 | 8/2014 | Hajati et al. |
| 2014/0220723 A1 | 8/2014 | Liu et al. |
| 2014/0221838 A1* | 8/2014 | Loupas ............... G01S 7/52071 600/454 |
| 2014/0226430 A1 | 8/2014 | Bloch |
| 2014/0249419 A1 | 9/2014 | Morita |
| 2014/0276069 A1 | 9/2014 | Amble |
| 2014/0276087 A1 | 9/2014 | Corl |
| 2014/0328504 A1 | 11/2014 | Stephanou et al. |
| 2014/0355377 A1 | 12/2014 | Hiriyannaiah |
| 2015/0023561 A1 | 1/2015 | Hamilton |
| 2015/0087988 A1 | 3/2015 | Lee |
| 2015/0145374 A1 | 5/2015 | Xu et al. |
| 2015/0158052 A1 | 6/2015 | Hajati |
| 2015/0160322 A1 | 6/2015 | Matthews |
| 2015/0265245 A1 | 9/2015 | Von Ramm et al. |
| 2015/0333730 A1 | 11/2015 | Meltaus et al. |
| 2016/0007961 A1 | 1/2016 | Lee et al. |
| 2016/0033454 A1* | 2/2016 | Matsuda ............... H10N 30/00 29/25.35 |
| 2016/0041129 A1 | 2/2016 | Cho et al. |
| 2016/0045935 A1 | 2/2016 | Yoon et al. |

(56) References Cited

U.S. PATENT DOCUMENTS

| | | | |
|---|---|---|---|
| 2016/0107194 A1 | 4/2016 | Panchawagh et al. | |
| 2016/0211828 A1 | 7/2016 | Simmonds et al. | |
| 2016/0262725 A1 | 9/2016 | Boser et al. | |
| 2016/0288168 A1 | 10/2016 | Hynynen et al. | |
| 2017/0000461 A1 | 1/2017 | Wong et al. | |
| 2017/0224312 A1 | 8/2017 | Call et al. | |
| 2017/0232474 A1 | 8/2017 | Oralkan et al. | |
| 2017/0262598 A1 | 9/2017 | Petkov et al. | |
| 2017/0312782 A1 | 11/2017 | Morelli et al. | |
| 2017/0328870 A1 | 11/2017 | Garlepp et al. | |
| 2018/0153510 A1 | 6/2018 | Haque et al. | |
| 2018/0153512 A1 | 6/2018 | Akkaraju et al. | |
| 2018/0154393 A1 | 6/2018 | Viegas et al. | |
| 2018/0154394 A1 | 6/2018 | Haque et al. | |
| 2018/0192999 A1 | 7/2018 | Song et al. | |
| 2019/0090857 A1 | 3/2019 | Yamamoto et al. | |
| 2019/0126317 A1* | 5/2019 | Pernot | A61B 8/429 |
| 2019/0151898 A1* | 5/2019 | Matsuda | H04R 17/00 |
| 2019/0184426 A1 | 6/2019 | Kojima et al. | |
| 2019/0290243 A1 | 9/2019 | Bryzek | |
| 2019/0302256 A1* | 10/2019 | Bouzari | G01S 15/892 |
| 2019/0316957 A1 | 10/2019 | Akkaraju | |
| 2019/0316958 A1 | 10/2019 | Akkaraju | |
| 2019/0387321 A1 | 12/2019 | Dayton et al. | |
| 2020/0007991 A1 | 1/2020 | Fanget | |
| 2020/0046320 A1 | 2/2020 | Wodnicki et al. | |
| 2020/0101492 A1 | 4/2020 | Akiyama et al. | |
| 2020/0225082 A1 | 7/2020 | Akkaraju | |
| 2020/0249079 A1 | 8/2020 | Akkaraju | |
| 2021/0022706 A1 | 1/2021 | Haque | |
| 2021/0022707 A1 | 1/2021 | Haque | |
| 2021/0124044 A1 | 4/2021 | Haque | |
| 2021/0137497 A1 | 5/2021 | Bryzek | |
| 2021/0172788 A1 | 6/2021 | Akkaraju | |
| 2021/0331204 A1* | 10/2021 | Zhang | G01H 11/08 |

FOREIGN PATENT DOCUMENTS

| | | |
|---|---|---|
| CN | 105310721 A | 2/2016 |
| CN | 108886659 A | 11/2018 |
| CN | 109416907 A | 3/2019 |
| CN | 110227640 A | 9/2019 |
| CN | 110546775 A | 12/2019 |
| CN | 112118791 A | 12/2020 |
| EP | 0308899 A2 | 3/1989 |
| EP | 1992290 A1 | 11/2008 |
| EP | 2745137 | 6/2014 |
| EP | 1436097 B1 | 2/2016 |
| JP | H0723500 A | 1/1995 |
| JP | 2005-295553 A | 10/2005 |
| JP | 2007229327 A | 9/2007 |
| JP | 2012084748 A | 4/2012 |
| JP | 2013-518530 A | 5/2013 |
| JP | 2014-528266 A | 10/2014 |
| JP | 2017528940 A | 9/2017 |
| JP | 2020-500682 A | 1/2020 |
| KR | 20100121544 A | 11/2010 |
| WO | WO-2013044471 A1 | 4/2013 |
| WO | WO2016054447 A1 | 4/2016 |
| WO | 2018102621 | 6/2018 |
| WO | WO-2018102621 A1 | 6/2018 |
| WO | WO-2018102622 A1 | 6/2018 |
| WO | 2019182771 | 9/2019 |
| WO | WO-2020139775 A1 | 7/2020 |

OTHER PUBLICATIONS

Assef et al., A reconfigurable arbitrary waveform generator using PWM modulation for ultrasound research. BioMedical Engineering OnLine 12:24 [1-13] (2013).
Choudhry et al., Comparison of tissue harmonic imaging with conventional US in abdominal disease. RadioGraphics: Imaging and Therapeutic Technology 20:1127-1135 (2000).
Dahl, Ultrasound beamforming and image formation. http://people.duke.edu/-jjd/RSNA_USbeamforming.pdf [Slide presentation] (c. 2005).
Dausch et al., Theory and operation of 2-D array piezoelectric micromachined ultrasound transducers. IEEE Transactions on Ultrasonics, Ferroelectrics, and Frequency Control 55(11):2484-2492 (2008).
Doerry, Generating nonlinear FM chirp waveforms for radar. Sandia Report, SAND2006-5856:1-34 (2006).
Felix et al., Biplane ultrasound arrays with integrated multiplexing solution for enhanced diagnostic accuracy in endorectal and transvaginal imaging. http://www.vermon.com/vermon/publications/Felix_UFFC_2005.pdf (2005).
Goldman, Apple's Lightning connector and you: what you should know. CNET Sep. 19, 2012: https://www.cnet.com/news/apples-lightning-connector-and-you-what-you-should-know/ (2012).
Guedes et al., Aluminum nitride pMUT based on a flexurally-suspended membrane. IEEE 16th International Solid-State Sensors, Actuators and Microsystems Conference: 12169346 (2011), Abstract Only Provided.
Hajati et al. ,Three-dimensional micro electromechanical system piezoelectric ultrasound transducer. Appl. Phys. Lett. 101:253101 (2012); doi: 10.1063/1.4772469 (2012), Abstract Only Provided.
Harput, Use of chirps in medical ultrasound imaging. Ultrasound Group, School of Electronic and Electrical Engineering, University Of Leeds, PhD Thesis, Dec. 2012.
Karki, Signal conditioning piezoelectric sensors. Texas Instruments Application report, SLA033A:1-5 (2000).
Khuri-Yakub et al., Capacitive micro machined ultrasonic transducers for medical imaging and therapy. Journal of Micromech Microeng. 21(5):054004-054014 (2011).
Lach et al., Piezoelectric materials for ultrasonic probes. http://www.ndt.net/article/platte2/platte2.htm NDTnet 1(9):1-9 (1996).
Lee et al., Wafer-to-wafer alignment for three-dimensional integration: a review. Journal of MicroElectroMechanical Systems 20(4):885-898 (2011).
Lu et al., High frequency piezoelectric micromachined ultrasonic transducer array for intravascular ultrasound imaging. Proceedings of the IEEE International Conference on Micro Electro Mechanical Systems (MEMS):06765748 (2014).
Martin, Introduction to B-mode imaging. Cambridge University Press; Diagnostic Ultrasound: Physics and equipment, 2nd Edition. Chapter 1:1-10 (2010).
Mina, High frequency transducers from PZT films. Materials Science and Engineering Thesis; Pennsylvania State University:1-199 (2007).
Moazzami et al., Electrical characteristics of ferroelectric PZT thin films for DRAM applications. IEEE Transaction on Electron Devices 39(9):2044-2049 (1992).
Orenstein Scanning in pain—sonographers seek relief from job-related hazard. Radiology Today 10(8):24 (2009).
Ovland, Coherent plane-wave compounding in medical ultrasound imaging. NTNU—Trondheim, Norwegian University of Science and Technology, Master of Science Thesis, 1-62 (Jun. 2012).
PCT/US2017/064090 International Search Report and Written Opinion dated Mar. 28, 2018.
PCT/US2017/064091 International Search Report and Written Opinion dated Mar. 28, 2018.
PCT/US2019/068004 International Search Report and Written Opinion dated Apr. 21, 2020.
Pye et al., Adaptive time gain compensation for ultrasonic imaging. Ultrasound in Medicine and Biology 18(2):205-212 [abstract] (1992).
Rodriguez et al., Low cost matching network for ultrasonic transducers. Physics Procedia 3:1025-1031 (2010).
Smyth, Design and modeling of a PZT thin film based piezoelectric micromachined ultrasonic transducer (PMUT). MSME Thesis, MIT 1-156 (2012).
Spectral doppler. http://www.echocardiographer.org/Echo%20Physics/spectral%20doppler.html (2017).
Szabo. Diagnostic ultrasound imaging: inside out. Elsevier Academic Press, ISBN: 0-12-680145-2 (572 pgs) (2014), Abstract Only Provided.

(56) References Cited

OTHER PUBLICATIONS

Trots et al., Synthetic aperture method in ultrasound imaging. In Tech Press; Ultrasound Imaging, Masayuki Tanabe (Ed.). http://www.intechopen.com/books/ultrasound-imaging/synthetic-aperture-method-in-ultrasound-imaging. Chapter 3:37-56 (2011).
U.S. Appl. No. 15/826,614 Office Action dated Oct. 1, 2020.
Wang et al., Broadband piezoelectric micromachined ultrasonic transducer (pMUT) using mode-merged design. Proceedings of the 10th IEEE International Conference on Nano/Micro Engineered and Molecular Systems (IEEE-NEMS 2015):15260900. Xi'an, China, Apr. 7-11, 2015, Abstract Only Provided.
Wang et al., Zero-bending piezoelectric micromachined ultrasonic transducer (pMUT) with enhanced transmitting performance. Journal of Microelectromechanical Systems 24(6):2083-2091 (2015).
Yoon; "Orthogonal Quadratic Chirp Signals for Simultaneous Multi-Zone Focusing in Medical Ultrasound Imaging"; IEEE Transactions on Ultrasonics, Ferroelectrics, and Frequency Control; vol. 59, Issue 5, May 21, 2012; pp. 1061-1069.
Bjastad; "High Frame Rate Ultrasound Imaging Using Parallel Beamforming"; Jan. 2009; 136 pages; Norweigan University of Science and Technology.
D. Evans; "Doppler Ultrasound: Physics, Instrumentation and Signal Processing"; Second Edition; John Wiley & Sons Ltd., New York, 2000; Abstract Provided.
Jensen; "Estimation of Blood Flow Velocities Using Ultrasound"; Cambridge University Press, Cambridge, 1996; Abstract Provided.
Bjaerum; "Statistical Evaluation of Clutter Filters in Color Flow Imaging"; Elsevier Ultrasonics; 38, pp. 376-380; 2000.
Bjaerum; "Clutter Filter Design for Ultrasound Color Flow Imaging"; IEEE Transaction of Ultrasonic, Ferroelectrics and Frequency Control; 49 (2), pp. 204-216; 2002.
Bjaerum; "Clutter Filters Adapted to Tissue Motion in Ultrasound Color Flow Imaging"; IEEE Transaction on Ultrasonic, Ferroelectronics and Frequency Control; 49, pp. 693-704; 2002.
Korean Office Action for Application No. 10-2022-7035417, dated Aug. 22, 2023, 13 pages including translation.
U.S. Appl. No. 17/507,615 Office Action dated May 1, 2024.
U.S. Appl. No. 17/215,776 Office Action dated Apr. 16, 2024.

\* cited by examiner

ULTRASONIC IMAGING DEVICE WITH PROGRAMMABLE ANATOMY AND FLOW IMAGING

BACKGROUND

Transducers in ultrasonic imagers transmit an ultrasonic beam towards the target to be imaged and a signal from the reflected waveform is used to create an image. The reflected waveform from tissue is used to form an image of the anatomy being viewed, whereas blood flow, velocity and direction of flow is measured using Doppler shift principles under electronic control.

BRIEF DESCRIPTION OF THE DRAWINGS

The accompanying drawings illustrate various examples of the principles described herein and are part of the specification. The illustrated examples are given merely for illustration, and do not limit the scope of the claims.

Figure 1:
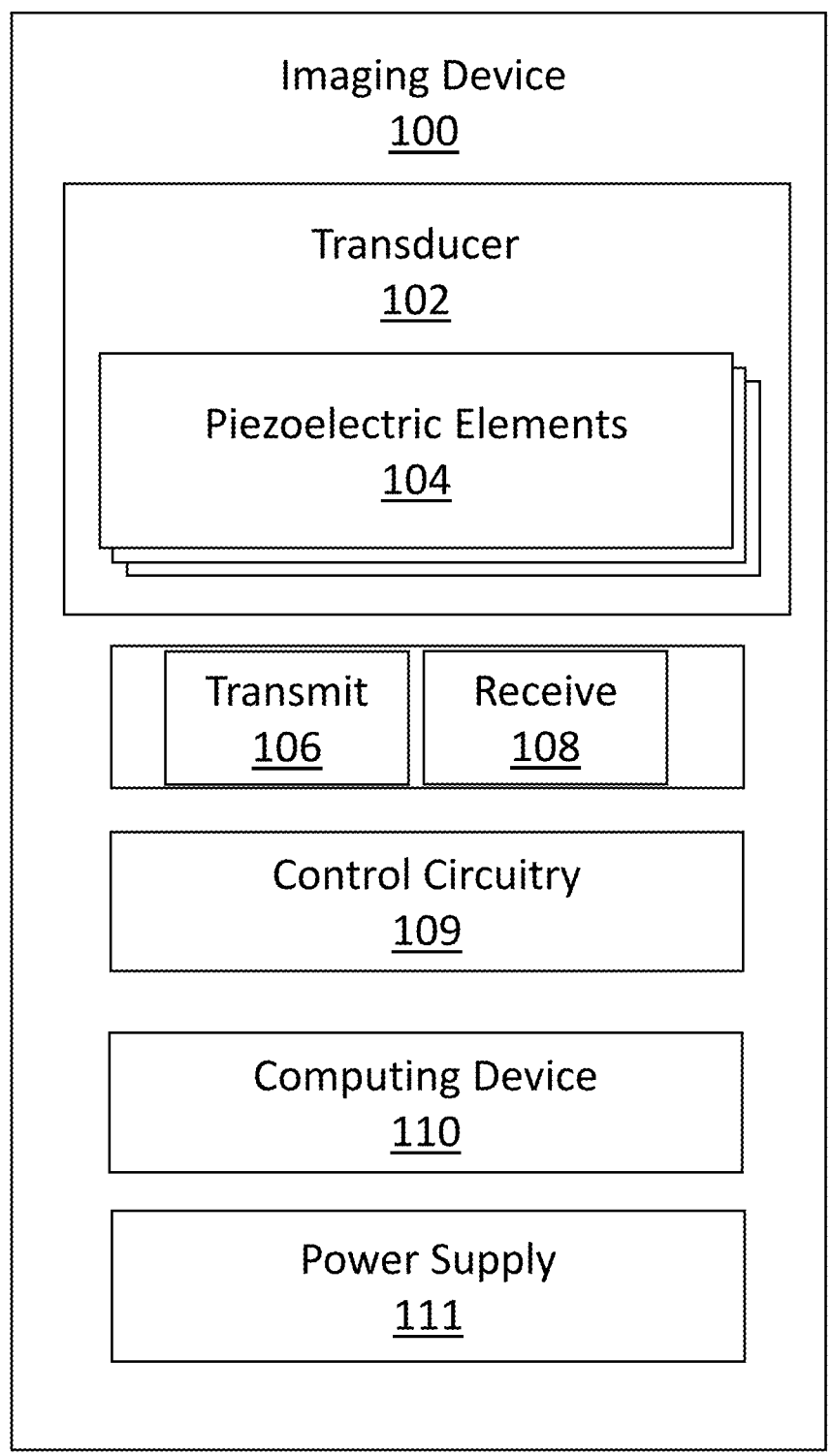
FIG. 1 illustrates a block diagram of an imaging device for anatomy and flow imaging, according to an example of the principles described herein.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION

The present invention relates to imaging devices, and more particularly to portable handheld ultrasonic imaging devices having the ability to perform flow and anatomy imaging.

Ultrasound imaging (sonography) uses high-frequency sound waves to view inside the body. Because ultrasound images are captured in real-time, they can also show movement of the body's internal organs as well as blood flowing through the blood vessels. The sound waves are used to create and display images of internal body structures such as tendons, muscles, joints, blood vessels, and internal organs.

To perform imaging, the imaging device transmits a signal into the body and receives a reflected signal from the body part being imaged. Types of imaging devices include transducers, which may also be referred to as transceivers or imagers, and which may be based on either photo-acoustic or ultrasonic effects. Such transducers can be used for imaging as well as other applications. For example, transducers can be used in medical imaging to view anatomy of tissue or other organs in a body. Transducers can also be used in industrial applications such as materials testing or therapeutic applications such as local tissue heating of HIFU based surgery. When imaging a target and measuring movement of the target, such as flow velocity and direction blood, Doppler measurements techniques are used. Doppler techniques are also applicable for industrial applications to measure flow rates, such as fluid or gas flow in pipes.

The difference between transmitted and reflected wave frequencies due to relative motion between the source and the object is known as a Doppler effect. The frequency shift is proportional to the movement speed between the transducer and the object. This effect is exploited in ultrasound imaging to determine blood flow velocity and direction.

Doppler imagers may generate either continuous wave (CW) or a pulsed wave (PW) ultrasound beam. In CW Doppler, signals are continuously transmitted and received, requiring two element transducers, one for transmitting and another for receiving. In PW operation, a single-element transducer is used for transmitting and receiving the ultrasound signals.

For ultrasound imaging, transducers are used to transmit an ultrasonic beam towards the target to be imaged. A reflected waveform is received by the transducer, converted to an electrical signal and with further signal processing, an image is created. Velocity and direction of flow may be measured using an array of micro-machined ultrasonic transducers (MUTs).

B-mode imaging for anatomy is a two-dimensional ultrasound image display composed of dots representing the ultrasound echoes. The brightness of each dot is determined by the amplitude of the returned echo signal. This allows for visualization and quantification of anatomical structures, as well as for the visualization of diagnostic and therapeutic procedures. Usually, the B-mode image bears a close resemblance to the actual anatomy of a cutout view in the same plane. In B-mode imaging, a transducer is first placed in a transmit mode and then placed in receive mode to receive echoes from the target. The echoes are signal processed into anatomy images. The transducer elements are programmable such that they can be either in transmit mode or in receive mode, but not simultaneously.

The use of color flow Doppler, color Doppler imaging, or simply color Doppler allows the visualization of flow direction and velocity for blood in an artery or vein within a user defined area. A region of interest is defined, and the Doppler shifts of returning ultrasound waves are color-coded based on average velocity and direction. Sometimes these images are overlapped (co-imaged) with anatomy images in B-mode scan to present a more intuitive feel of flow relative to anatomy being viewed. Doppler imaging can also be PW Doppler so that the range and velocity of flow is determined, but maximum flow rate is dependent on pulse repetition frequency used, otherwise images are aliased making higher velocities look like lower velocities. Doppler shift can be measured from an ensemble of waves received to measure flow velocity using PW mode of Doppler imaging. CW Doppler is a continuous imaging technique where aliasing is avoided through continuous transmitting from one transducer element while receiving echoes from another transducer element. With this technique, the range is ambiguous. In a programmable instrument, both pulsed and continuous techniques can be implemented as discussed later. PW and Color Doppler may use a selected number of elements in an array. First, the elements are placed in a transmit mode and after echoes have returned, the elements are placed in a receive mode where the received signal is processed for Doppler signal imaging. For CW Doppler, at least two different elements are utilized, where each element is in transmit mode while the other element is in receive mode continuously.

The Doppler signal from a moving object contains not only information about flow, but also backscatter signals containing clutter that originates from surrounding tissue or slowly moving vessels. This clutter signal may be typically 40 to 80 dB stronger than the Doppler shift signal originating from blood. Thus, a clutter rejection is needed to estimate the flow accurately. Clutter suppression is a step in the processing of Doppler signal. A high pass filter (HPF) may be used to remove the clutter signal from the Doppler shift signal. A high pass filter is used to suppress signals from stationary or slow-moving tissue or any other organs. Signals from slow moving objects are of low-frequency, but they may have amplitudes much stronger than high frequency signals generated from the faster blood flow. Thus, for separating the signals from blood and tissue, a high pass filter with a sharp transition band is used. These filters can be developed digitally in the receiver. These filters, sometimes known as Wall filters, look at the difference in signals from different transmissions, with the signals aligned in phase. Any deviation caused by Doppler shift is the desired output. However, if low frequency clutter causes some of this deviation, the sensitivity of the flow detection algorithm becomes degraded. Effects from switched mode dc to dc converter-based power supplies may cause clock frequency and harmonics to show up in the power supply. Further, these frequencies can create other frequencies due to interaction of other switching phenomena, for example, pulse repetition rate of the Doppler sequence.

To the extent that these kinds of behavior or intermodulation behavior are caused by nonlinearities, spurious signals show up in the frequencies of interest for flow imaging and sensitivity of flow imaging is reduced. Another example of clutter is amplitude jitter of the pulses used in the transmit pulsar. One source of the clutter may be the power supply amplitudes varying from pulse to pulse, due to the power supply capacitors being drained of charge to deliver current during a pulse and not getting recharged to a same level for the next pulse.

In addition to use of digital Wall filters, low frequency content causing clutter can be minimized by using a high pass filter ahead of the digital filter. Filters can be in the analog domain and also in the digital domain. A part of these filters can also be performed right at the transducer interface, where real time control of high pass frequency is achieved by controlling the radio frequency ($R_f$) and carrier frequency ($C_{HF}$) network. Radio frequency ($R_f$) refers to the rate of oscillation of electromagnetic radio waves in the range of 3 kHz to 300 GHz, as well as the alternating currents carrying the radio signals. Carrier frequency ($C_{HF}$) is defined as the transmission of a fixed frequency that has been altered or otherwise modulated to carry data. This achieves a 20 dB/Dec high pass slope.

Additionally, beyond use of a low noise amplifier (LNA), other digitally controlled high pass filters (HPF) can be leveraged to simplify operations in the receiver to save power and processing time. By rejecting unneeded clutter before time gain compensation (TGC), an LNA increases the dynamic range of the signal presented to an analog to digital converter (ADC). The digitized bits can now be processed for further Doppler operations.

The acquisition of Doppler relies on repeated transmission of pulses to acquire data from a particular region of interest. Such acquisition is precise in its periodicity to ensure that the Doppler signal is uniformly sampled for further spectrogram processing. This can be a major constraint to ultrasound imaging systems when this Doppler signal acquisition is done in such modes as Duplex or Triplex imaging where B-mode or color flow signals are acquired concurrently. This constraint reduces the frame rates for other modes and hence limits the ability of the sonographer to follow events in real-time. Moreover, the rapid periodic transmission of ultrasound pulses to the same location can increase the average power per unit area beyond certain safety standards and therefore limitations on acoustic power generated drive close attention to keep this in the safe zone.

Doppler shift principles are used to calculate the blood flow velocity. Other types of velocity can be calculated, such as body fluids, industrial fluids, gases, etc. When the observer moves towards the source, the increased frequency, $f_r$, due to passing more wave cycles per seconds, is given by:

$$f_r = f_t \frac{c+v}{c}$$

In the above, $f_t$ is the transmitted frequency, c is the velocity of sound in tissue, and v is the velocity of the observer (for example, blood).

The velocity is replaced by the component of velocity in the wave direction, v cos ø, if the velocity of the observer is at an angle ø to the direction of the wave propagation.

$$f_{ry} = f_t \frac{c+v\cos\emptyset}{c}$$

If the observer is at rest and the source moves with the velocity in the direction of wave travel, the wavelengths are compressed. The resulting observed frequency is:

$$f_{ry} = f_t \frac{c}{c-v}$$

Taking the angle into account:

$$f_{ry} = f_t \frac{c}{c-v\cos\emptyset}$$

In application of ultrasound, an ultrasonic beam is backscattered from the moving blood cells and tissue. Both of the above effects combine to give the transmitted Doppler shift in frequency. The observed frequency is then given by:

$$f_{ry} = f_t \frac{c+v\cos\emptyset}{c} * \frac{c}{c-v\cos\emptyset} = f_t \frac{c+v\cos\emptyset}{c-v\cos\emptyset}$$

As mentioned, the Doppler shift frequency is the difference between incident frequency $f_t$ and reflected frequency $f_r$, and is therefore given by:

$$f_d = f_r - f_t$$

$$f_d = f_t \frac{c+v\cos\emptyset}{c-v\cos\emptyset} - f_t$$

Since c>>v $$f_d = \frac{2*ft*v}{c}\cos\emptyset$$

From the last relationship, the Doppler shift depends on the angle ø to the direction of the propagation and the transmitted frequency.

The best reflection takes place when measuring at 90 degrees to the electronically steered in the azimuth and elevation plane to achieve optimal Doppler signal detection. This elevation steering is controlled by a combination of elevation delay control along with any desired azimuth.

Figure 24:
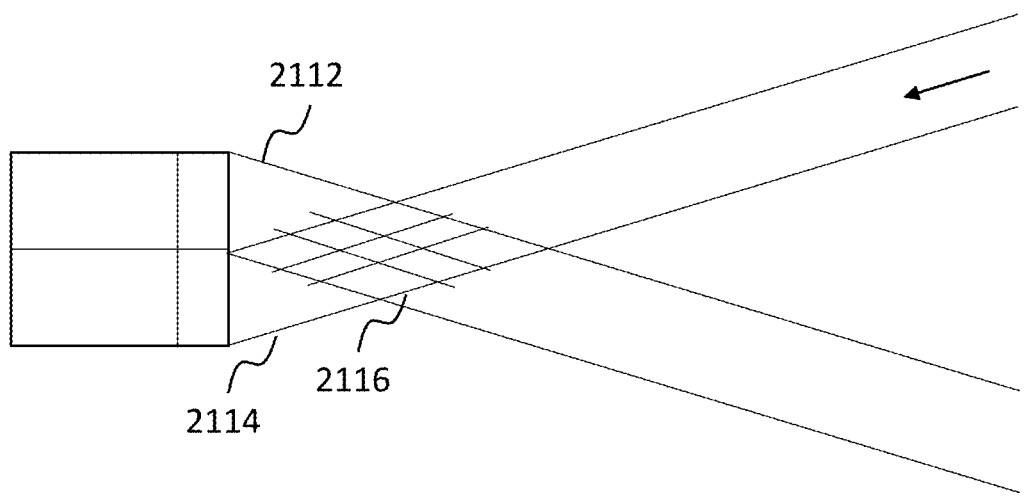
FIG. 24 illustrates a flow sensitive region in a Doppler sample volume.

A continuous wave Doppler system is a system that sends and receives a continuous ultrasound wave by using two separate transducer elements housed within the same probe. Because transmission and reception are continuous, the system has no depth resolution, except in the sense that signals originating from close to the transducer experience less attenuation than those from a distant target. The transmitted 2112 and received beams 2114 are shown in a Doppler sample volume in FIG. 24. The flow sensitive zone 2116 over which Doppler information can be acquired (sample volume) is the region of transmitting and receiving beam overlap as indicated by cross-hatched lines that occur at some distance from the transducer face.

It is possible to construct an element that includes two sub-elements for example, where one can be in transmit mode and the other in receive mode. By using embedded dual sub-elements instead of a single element in the transducer, the entire transducer area or portions selected thereof can be used for transmission and reception. Also, areas of intersection are increased by use of dual sub-elements.

Imaging devices such as ultrasound imagers used in medical imaging use piezoelectric (PZT) material or other piezo ceramic and polymer composites. To fabricate the bulk PZT elements for the transducers, a thick piezoelectric material slab can be cut into large rectangular shaped PZT elements. The rectangular-shaped PZT elements are expensive to build, since the manufacturing process involves precise cutting of the rectangular-shaped thick PZT or ceramic material and mounting it onto substrates with precise spacing. Furthermore, the impedance of the transducers is much higher than acoustic impedance of tissue, which requires use of impedance matching layers to allow for practical transmission and reception of signals.

Still further, such thick bulk PZT elements can require relatively high voltage pulses. For example, 100 volts (V) or more may be required to generate transmission signals. High drive voltage results in high power dissipation since the power dissipation in the transducers is proportional to the square of the drive voltage. The high power dissipation generates heat within the imaging device such that cooling arrangements are necessitated. The use of cooling systems increases the manufacturing costs and weights of imaging devices which makes the imaging devices more burdensome to operate. High voltages also increase the cost of electronics.

Even further, the transmit/receive electronics for the transducers may be located far away from the transducers themselves, thus requiring micro-coaxial cables between the transducers and transmit/receive electronics. In general, the cables have a precise length for delay and impedance matching, and, quite often, additional impedance matching networks are used for efficient connection of the transducers through the cables to the electronics.

Accordingly, the present specification describes the use of piezoelectric micromachined ultrasound transducers (pMUTs), which can be efficiently formed on a substrate leveraging various semiconductor wafer manufacturing operations. Semiconductor wafers may come in 6 inch, 8 inch, and 12 inch sizes and are capable of housing hundreds of transducer arrays. These semiconductor wafers start as a silicon substrate on which various processing steps are performed. An example of such an operation is the formation of SiO2 layers, also known as insulating oxides. Various other steps such as the addition of metal layers to serve as interconnects and bond pads or copper pillars may be used to allow connections of the pMUTs to other electronics. Also, use of etching techniques to create cavities in the silicon structure allows formation of membranes that can move under electrical control or due to external pressure inputs. Compared to the conventional transducers having bulky piezoelectric material, pMUTs built on semiconductor substrates are less bulky, are cheaper to manufacture, and have simpler and higher performance interconnection between electronics and transducers. As such, they provide flexibility in the operational frequency, and potential to generate higher quality images due to lower parasitics in the interconnection.

In one example, the imaging device is coupled to an application specific integrated circuit (ASIC) that includes transmit drivers, sensing circuitry for received echo signals, and control circuitry to control various operations. The ASIC can be formed on a separate semiconductor wafer and the pMUT on another wafer. Also, the ASIC can be placed in close proximity to pMUT elements to reduce parasitic losses. In one example, the ASIC may be 50 micrometers (µm) or less away from the transducer array. There may be less than a 100 µm separation between the 2 wafers or 2 die, where each wafer includes many dies and a die includes a transducer in the transducer wafer and an ASIC in the ASIC wafer. The ASIC may have matching dimensions relative to the pMUT to allow the devices to be stacked for wafer-to-wafer interconnection or transducer die on ASIC wafer or transducer die to ASIC die interconnection. Alternatively, the transducer can be developed on top of the ASIC wafer using low temperature piezo material sputtering and other low temperature processing compatible with ASIC processing.

While pMUTs have potential for advanced ultrasonic imaging, some limitations have impeded their utilization in high performance imaging implementation. As an example, pMUTs utilizing Aluminum Nitride exhibit low sensitivity related to transmit and receive operations making them candidates for less demanding applications. Other pMUTs utilizing PZT require relatively high voltages and exhibit relatively low bandwidth and low efficiency.

Accordingly, the present specification describes pMUTs that 1) have an enhanced sensitivity, 2) may operate at low voltages, 3) exhibit high bandwidth operation, and 4) exhibit good linearity. Specifically, the present specification describes pMUTs in close proximity to the associated control circuitry. This allows 2D and 3D imaging under control of a control circuitry in a small portable device.

Another type of transducer is a capacitive micromachine ultrasonic transducer (cMUT). However, cMUT sensors have difficulty with generating sufficient acoustic pressure at lower frequencies (where the bulk of deep medical imaging occurs) compared to PZT based devices and are inherently nonlinear. Furthermore, cMUTs require high voltage operation.

In general, an imaging device of the present specification includes a number of transmit channels and a number of receive channels. Transmit channels drive the piezoelectric elements with a voltage pulse at a frequency the elements are responsive to. This causes an ultrasonic waveform to be emitted from the piezoelectric elements which waveform is directed towards an object to be imaged. In some examples, the imaging device with the transducer array of piezoelectric elements makes mechanical contact with the body using a gel in between the imaging device and the body. The ultrasonic waveform travels towards the object, i.e., an organ, and a portion of the waveform is reflected back to the piezoelectric elements, where the received ultrasonic energy is converted to an electrical energy, which is then further processed by a number of receive channels and other circuitry to develop an image of the object.

These transmit and receive channels consume power and in instruments where there are many channels (to generate high quality images), the power may cause excessive heat buildup in the imaging device. If the temperature rises past a certain value, it may affect operation of the imaging device, could pose a danger to the operator, could pose a danger to a patient, and may be outside of regulatory specifications which restrict how high the temperature can rise. An ultrasound imaging device includes a transducer array, an ASIC, transmit and receive beamforming circuitry, and control electronics. Specifications restrict the maximum temperature that can be tolerated, which in turn, severely restricts which electronic circuits can be housed in the imaging device and also restricts how the imaging device is operated. Such restrictions can negatively affect the image quality achieved and the frame rate of images. Furthermore, imaging devices may be battery-powered which may drain quickly in instruments with many channels as each channel draws energy.

The imaging device of the present disclosure resolves these and other issues. Specifically, the imaging device controls power dissipation without exceeding temperature limits of the imaging device all while maintaining needed image quality. Specifically, the number of receive channels and/or transmit channels used to form an image are electronically adaptable to save power, for example, in cases where a lower number of channels is acceptable. As a specific example, each of the number of channels may be dynamically controlled to reduce power, or to be powered down entirely. Additionally, other characteristics of each channel are also configurable to reduce power. Such advanced control allows the imaging device to be operated within safe temperature thresholds, and may do so without materially sacrificing needed image quality. The lower power consumption also increases battery life.

Also, the imaging device includes a handheld casing where transducers and associated electronics are housed. The imaging device may also contain a battery to power the electronics. As described above, the amount of power consumed by the imaging device increases the temperature of the imaging device. To ensure satisfactory use of the imaging device and imaging device performance, the temperature of the body of the imaging device should remain below a threshold temperature. The imaging device of the present specification is electronically configured to reduce power and temperature notwithstanding the acquisition of high quality images which consumes a significant amount of power, reduces battery life, and increases temperature in the probe.

In one example, the present disclosure describes a high performance, low power, and low cost portable imaging device capable of 2D and 3D imaging using pMUTs in a 2D array built on a silicon wafer. Such an array coupled to an ASIC with electronic configuration of certain parameters enables a higher quality of image processing at a lower cost than has been previously possible. By controlling certain parameters, such as the number of channels used or the amount of power used per channel, power consumption can be altered and temperature can be changed.

The present disclosure describes an imaging device that relies on pMUT-based transducers connected to control electronics on a per pixel basis and housed in a portable housing. The imaging device allows system configurability and adaptability in real time to actively control power consumption and temperature in the imaging device. Flow imaging, in particular, can consume more power than anatomy imaging modes. Power is reduced by minimizing power dissipation within the imaging device by 1) altering the aperture size and/or 2) actively controlling power dissipation in those channels such that temperatures within the imaging device do not exceed specification limits. All this is done while achieving superior performance than would otherwise be possible. Further, acoustic power output can increase in Doppler modes compared to other anatomy modes. Electronic means are provided to control such power output levels.

The manufacturing cost of pMUTs described herein may be reduced by applying modern semiconductor and wafer processing techniques. For example, a thin film piezoelectric layer may be spun on or sputtered onto semiconductor wafers and later patterned to create piezoelectric sensors that each have two or more electrodes. In one example, each piezoelectric element may be designed to have the ability to emit or receive signals at a certain frequency, known as the center frequency, as well as the second and/or additional frequencies. Note that the term piezoelectric element, pMUT, transceiver, and pixel are used herein interchangeably.

In one example, an imaging device includes a transducer that has an array of piezoelectric elements that are formed on a substrate. Each of the piezoelectric elements include at least one membrane suspended from the substrate, at least one bottom electrode disposed on the membrane, at least one piezoelectric layer disposed on the bottom electrode, and at least one top electrode disposed on the at least one piezoelectric layer. Adjacent piezoelectric elements are configured to be isolated acoustically from each other.

In another example, an imaging device includes a transducer with a two-dimensional (2D) array of piezoelectric elements arranged in rows and columns on the transducer. Each piezoelectric element has at least two terminals and is physically isolated from each adjacent piezoelectric element to minimize cross talk. A first set of piezoelectric elements of the array includes that each piezoelectric element has a first top electrode connected to a respective receive amplifier and is electronically programmed as if connected together to form a first column. A second set of piezoelectric elements of the array includes that each piezoelectric element has a second top electrode connected to a respective transmit driver and is electronically programmed as if connected together to form a second column.

In another example, an imaging device includes a transducer and a 2D array of piezoelectric elements arranged in rows and columns on the transducer. Each piezoelectric element has at least two terminals. At least a first column of the piezoelectric elements includes that each piezoelectric element has a first top electrode connected to a respective receive amplifier or a transmit driver under programmed control. At least a second column of the piezoelectric elements includes that each piezoelectric element has a first top electrode connected to a respective receive amplifier or transmit driver under programmed control. The piezoelectric elements are programmed to transmit and then subsequently receive or to simultaneously transmit and receive.

Turning now to the figures, FIG. 1 illustrates a block diagram of an imaging device (100) with transmit (106) and receive channels (108), controlled by control circuitry (109), and having imaging computations performed on a computing device (110) according to principles described herein. FIG. 1 further includes a power supply (111) to energize the various components in the imaging device (100).

As described above, the imaging device (100) may be used to generate an image of internal tissue, bones, blood flow, or organs of human or animal bodies. Accordingly, the imaging device (100) transmits a signal into the body and receives a reflected signal from the body part being imaged. Such imaging devices (100) include piezoelectric transducers (102), which may be referred to as transceivers or imagers, which may be based on photo-acoustic or ultrasonic effects. The imaging device (100) can be used to image other objects as well. For example, the imaging device (100) can be used in medical imaging, flow measurements for fluids or gases in pipes, lithotripsy, and localized tissue heating for therapeutic and highly intensive focused ultrasound (HIFU) surgery.

In addition to use with human patients, the imaging device (100) may be used to get an image of internal organs of an animal as well. Moreover, in addition to imaging internal organs, the imaging device (100) may also be used to determine direction and velocity of blood flow in arteries and veins, as well as tissue stiffness, with Doppler mode imaging.

The imaging device (100) may be used to perform different types of imaging. For example, the imaging device (100) may be used to perform one dimensional imaging, also known as A-Scan, 2D imaging, also known as B scan (B-mode), three dimensional (3D) imaging, also known as C scan, and Doppler imaging. The imaging device (100) may be switched to different imaging modes and electronically configured under program control.

To facilitate such imaging, the imaging device (100) includes an array of piezoelectric transducers (102), each piezoelectric transducer (102) including an array of piezoelectric elements (104). A piezoelectric element (104) may also include two of more sub-elements, each of which may be configurable in a transmit or receive operation. The piezoelectric elements (104) operate to 1) generate the pressure waves that are passed through the body or other mass and 2) receive reflected waves off the object within the body, or other mass, to be imaged.

In some examples, the imaging device (100) may be configured to simultaneously transmit and receive ultrasonic waveforms. For example, certain piezoelectric elements (104) may send pressure waves toward the target object being imaged while other piezoelectric elements (104) receive the pressure waves reflected from the target object and develop electrical charges in response to the received waves.

In some examples, each piezoelectric element (104) may emit or receive signals at a certain frequency, known as a center frequency, as well as the second and/or additional frequencies. Such multi-frequency piezoelectric elements (104) may be referred to as multi-modal piezoelectric elements (104) and can expand the bandwidth of the imaging device (100).

The piezoelectric material that forms the piezoelectric elements (104) contracts and expands when different voltage values at a certain frequency are applied. Accordingly, as voltages alternate between different values applied, the piezoelectric elements (104) transform the electrical energy (i.e., voltages) into mechanical movements resulting in acoustic energy which is emitted as waves at the desired frequencies. These waves are reflected from a target being imaged and are received at the same piezoelectric elements (104) and converted into electrical signals that are then used to form an image of the target.

To generate the pressure waves, the imaging device (100) includes a number of transmit channels (106) and a number of receive channels (108). The transmit channels (106) include a number of components that drive the transducer (102), (i.e., the array of piezoelectric elements (104)), with a voltage pulse at a frequency that they are responsive to. This causes an ultrasonic waveform to be emitted from the piezoelectric elements (104) towards an object to be imaged. The ultrasonic waveform travels towards the object to be imaged and a portion of the waveform is reflected back to the transducer (102), where the receive channels (108) may collect the reflected waveform, convert it to an electrical energy, and process it, for example, at the computing device (110), to develop an image that can be displayed.

In some examples, while the number of transmit channels (106) and receive channels (108) in the imaging device (100) remain constant, the number of piezoelectric elements (104) that they are coupled to may vary. This coupling is controlled by the control circuitry (109). In some examples, a portion of the control circuitry (109) may be distributed in the transmit channels (106) and in the receive channels (108). For example, the piezoelectric elements (104) of a transducer (102) may be formed into a 2D array with N columns and M rows.

In one example, the 2D array of piezoelectric elements (104) have a number of columns and rows, such as 128 columns and 32 rows. The imaging device (100) may have up to 128 transmit channels (106) and up to 128 receive channels (108). Each transmit channel (106) and receive channel (108) is coupled to multiple or single piezoelectric elements or sub-elements (104). Depending on the imaging mode, each column of piezoelectric elements (104) may be coupled to a single transmit channel (106) and a single receive channel (108). The transmit channel (106) and receive channel (108) receive composite signals, which composite signals combine signals received at each piezoelectric element (104) within the respective column.

In another example, (i.e., during a different imaging mode), individual piezoelectric elements (104) are coupled to their own transmit channel (106) and their own receive channel (108).

In other examples, the computing device 110 or power supply and battery 111 are external.

Figure 2:
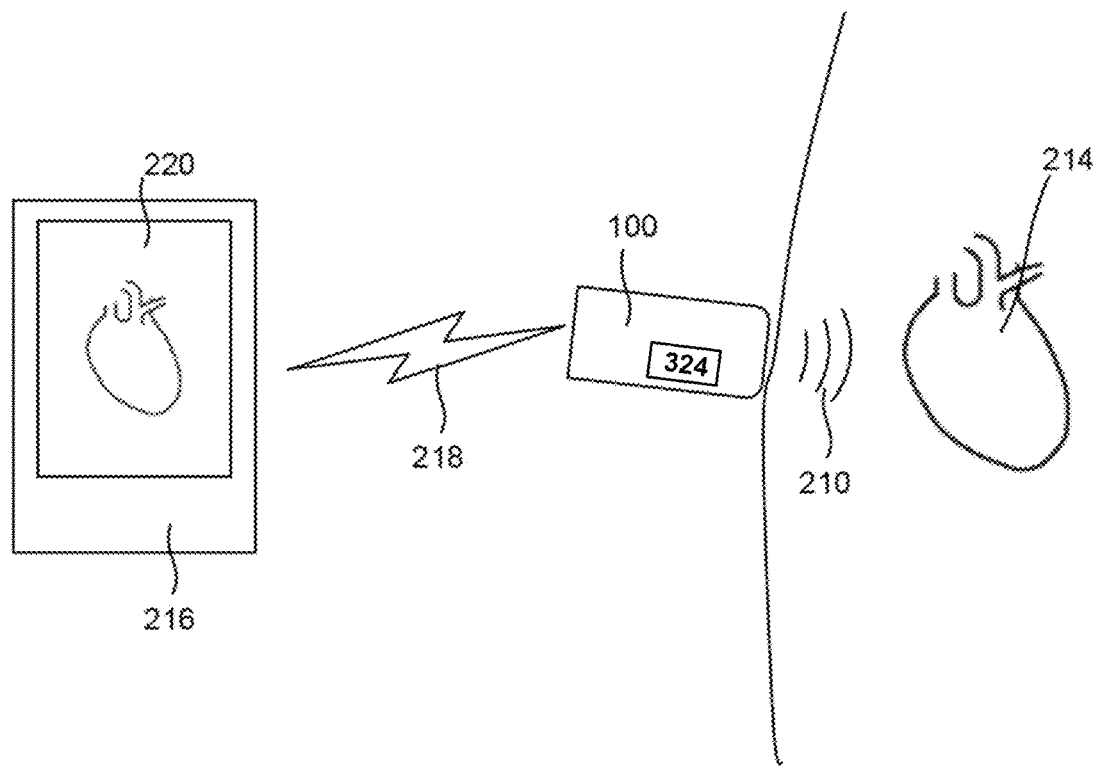
FIG. 2 illustrates a diagram of a portable imaging system for anatomy and flow imaging, according to an example of the principles described herein.

FIG. 2 is a diagram of an imaging system with flow imaging capability along with anatomy imaging capability, according to an example of the principles described herein. As depicted, the imaging system includes the imaging device (100) that generates and transmits, via the transmit channels (FIG. 1, 106) pressure waves (210) toward an internal organ, such as a heart (214), in a transmit mode/process. The internal organ, or other object to be imaged, may reflect a portion of the pressure waves (210) toward the imaging device (100) which captures, via the transducer (FIG. 1,102), receive channels (FIG. 1, 108), control circuitry (FIG. 1, 109), the computing device (FIG. 1,110), and the reflected pressure waves, and generates electrical signals in a receive mode/process. The system also includes another computing device (216) that communicates with the imaging device (100) through a communication channel (218). The imaging device (100) may communicate electrical signals to the computing device (216) which processes the received signals to complete formation of an image of the object. A display device (220) of the system can then display images of the organ or target including images that show blood flow related images in the targeted areas.

Figure 3:
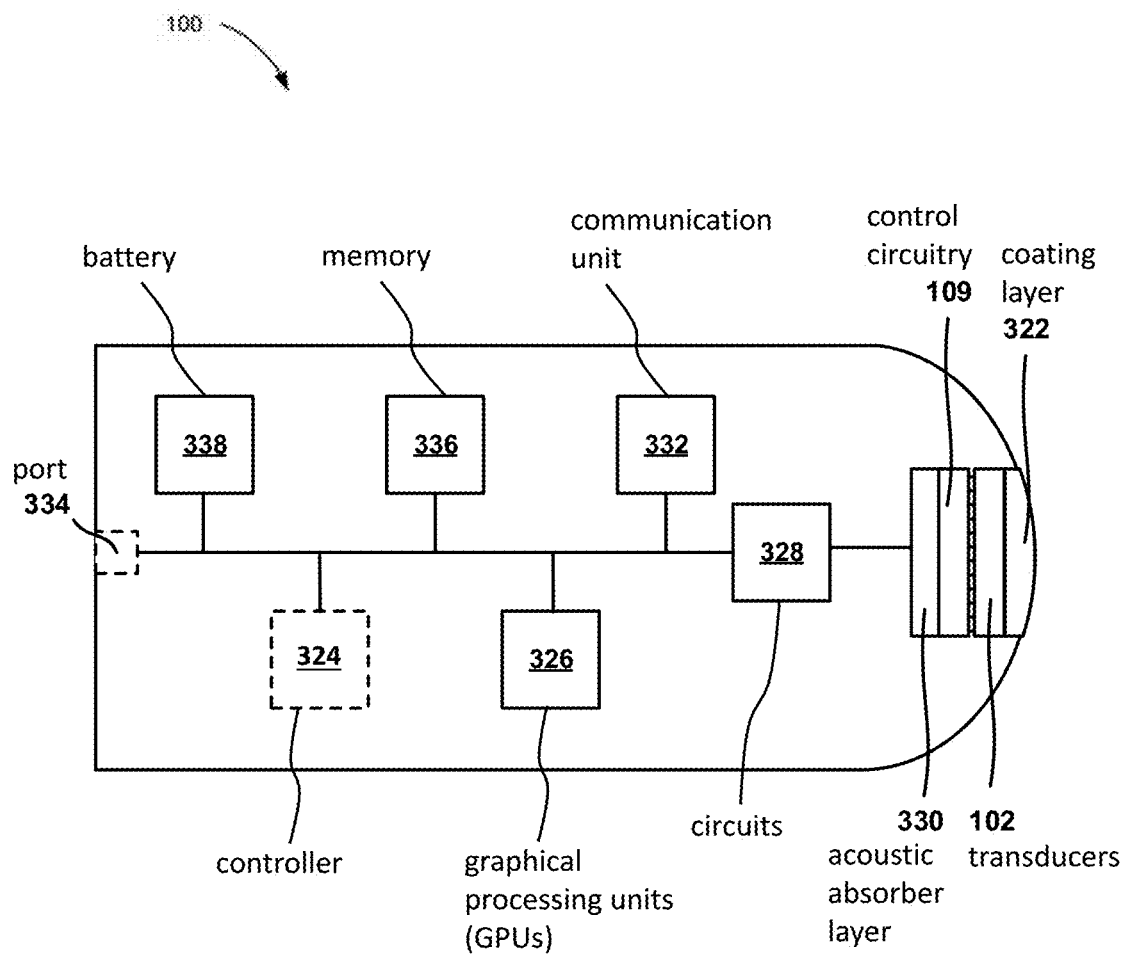
FIG. 3 illustrates a schematic diagram of an imaging device with imaging capability, according to an example of the principles described herein.

As depicted in FIG. 2, the imaging device (100) may be a portable, handheld device that communicates signals through the communication channel (218), either wirelessly (using a protocol, such as 802.11 protocol) or via a cable (such as universal serial bus 2 (USB2), USB 3, USB 3.1, and USB-C), with the computing device (216). In the case of a tethered connection, the imaging device (100) may include a port as depicted in FIG. 3 for receiving the cable that is to communicate with the computing device (216). In the case of a wireless connect, the imaging device (100) includes a wireless transmitter to communicate with the computing device (216).

The display device (220) and the computing device (216) may be separate from the imaging device (100) as shown. For example, the computing device (216) and display device (220) may be disposed within a separate device (e.g., a mobile device, such as cell phone or iPad, or a stationary computing device), which can display images to a user. In another example, the display device (220) and the computing device (220) are contained within the imaging device (100). That is, the imaging device (100), computing device (216), and display device (220) are disposed within a single housing.

FIG. 3 is a schematic diagram of an imaging device (100) with flow and anatomy measurement capability, according to an example of the principles described herein. As described above, the imaging device (100) may be an ultrasonic medical probe. FIG. 3 depicts the transducer(s) (102) of the imaging device (100). As described above, the transducer(s) (102) include an array of piezoelectric elements (FIG. 1, 104) that transmit and receive pressure waves (FIG. 2, 210). In some examples, the imaging device (100) includes a coating layer (322) that serves as an impedance matching interface between the transducers (102) and the human body, or other mass through which the pressure waves (FIG. 2, 210) are transmitted. In some cases, the coating layer (322) may serve as an impedance matching layer and also a lens when designed with a curvature consistent with a desired focal length. The coating layer (322) may consist of several layers of materials, some of which are used for impedance matching the transducer to tissue acoustic impedance and some of which are shaped into a mechanical lens to focus the acoustic signals in the elevation direction.

In embodiments, the user may apply gel on the skin of the human body before a direct contact with the coating layer (322) so that the impedance matching at the interface between the coating layer (322) and the human body may be improved. Impedance matching reduces the loss of the pressure waves (FIG. 2, 210) at the interface and the loss of the reflected wave traveling toward the imaging device (100) at the interface.

In some examples, the coating layer (322) may be a flat layer to maximize transmission of acoustic signals from the transducer(s) (102) to the body and vice versa. Certain parts of the coating layer (322) may be a quarter wavelength in thickness at a certain frequency of the pressure wave (FIG. 2, 210) generated or received by the transducer(s) (102).

The imaging device also includes control circuitry (109), such as an ASIC, for controlling the transducers (102). The control circuitry (109) may be housed in an ASIC along with other circuitry which is coupled to the transducers (102) by bumps that connect transducers (102) to the ASIC. As described above, the transmit channels (106) and receive channels (108) may be selectively alterable meaning that the quantity of transmit channels (106) and receive channels (108) that are active at a given time may be altered such that the power consumption characteristics of the transmit channels (106) and receive channels (108) and functionality may be altered. For example, if it is desired to alter the acoustic power during flow imaging modes, it is achieved by electronically controlling transmit channels with respect to the number of elements to be used on a line or the aperture to be used.

The transmit driving signal may be a multilevel signal, for example, 5V, 0V, and −5V. Other examples include 15V, 0V, and −15V. Other values are also possible. The signal can include many pulses or be continuous at a desired frequency. Drivers at the transmitter convert these multilevel signals, which are initially encoded into digital binary bits, to the final output level, such as say 15V. Using many such channels, ultrasonic transmit beams are created. By controlling delays in the channels, the beams can be steered in two-dimensional or three-dimensional domains. With the various beamforming operations described herein, 3D beamforming is possible. This is enabled using a 2D array that is addressable in the X and Y axis. Also possible is biplane imaging.

The imaging device (100) may further include Field Programmable Gate Arrays (FPGAs) or Graphical Processing Units (GPUs) (326) for controlling the components of the imaging device (100); circuit(s) (328), such as Analog Front End (AFE), for processing/conditioning signals and an acoustic absorber layer (330) for absorbing waves that are generated by the transducers (102) and propagated towards the circuits (328). For use with an acoustic absorber layer (330), the transducer(s) (102) may be mounted on a substrate and may be attached to an acoustic absorber layer (330). This layer absorbs any ultrasonic signals that are emitted in the reverse direction, which may otherwise be reflected and interfere with the quality of the image. While FIG. 3 depicts the acoustic absorber layer (330), this component may be omitted in cases where other components prevent a material transmission of ultrasound in the backwards direction, i.e., away from the transducers (102). The acoustic absorber may also be embedded between 102 and 109.

The imaging device (100) may include a communication unit (332) for communicating data with an external device, such as the computing and display device such as a smart phone or tablet (FIG. 2, 216). Communication may be through a port (334) or a wireless transmitter, for example. The imaging device (100) may include memory (336) for storing data. In some examples, the imaging device (100) includes a battery (338) for providing electrical power to the components of the imaging device (100). Electronic control of the channels and associated circuitry may have a particularly relevant impact when the imaging device (100) includes a battery (338). For example, as the receive channels (FIG. 1, 108) and transmit channels (FIG. 1, 106) include components that draw power, the battery depletes over time. The consumption of power by these components in some examples may be rather large such that the battery (338) would drain in a short amount of time. This is particularly relevant when obtaining high quality images which consume significant amounts of power. The battery (338) may also include battery charging circuits which may be wireless or wired charging circuits. The imaging device (100) may include a gauge that indicates a battery charge consumed and is used to configure the imaging device (100) to optimize power management for improved battery life.

By reducing the power consumption, or in some examples, powering down completely the different channels (FIG. 1, 106, 108), the battery (338) life is extended which enhances the ease of use of the imaging device (100). This is particularly applicable for imagers that support flow imaging, where power consumption is further increased.

Figure 4:
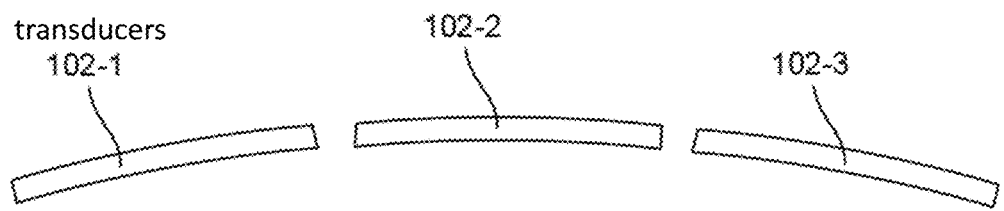
FIG. 4 illustrates a side view of a curved transducer array, according to an example of the principles described herein.
Figure 5:
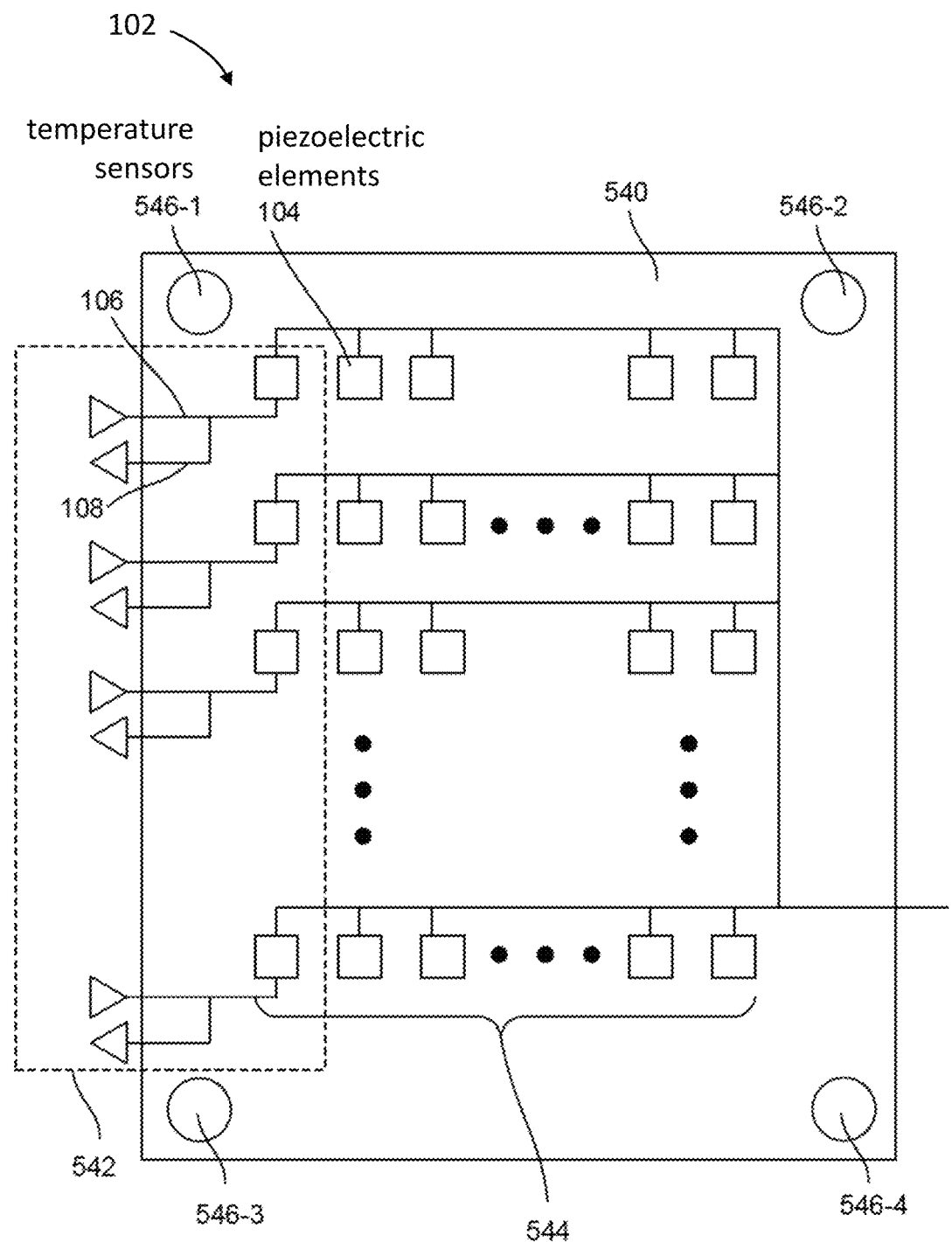
FIG. 5 illustrates a top view of a transducer, according to an example of the principles described herein.

FIG. 4 is a side view of a transducer (102) array, according to an example of the principles described herein. As described above, the imaging device (FIG. 1, 100) may include an array of transducers (102-1, 102-2, 102-3), each with their own array of piezoelectric elements (FIG. 1, 104). In some examples, the transducers (102) may be curved so as to provide a wider angle of the object (FIG. 2, 214) to be imaged. In other examples, the transducer (102) and arrays are disposed on a flat surface. FIG. 5 depicts a top view of a transducer (102) array. As depicted in FIG. 5, the transducer (102) may include a transceiver substrate (540) and one or more piezoelectric elements (104) arranged thereon. Unlike the conventional systems that use bulk piezoelectric elements, the piezoelectric element (104) may be formed on a wafer. The wafer may be diced to form multiple transducer (102) arrays to be used to build imaging devices. This process may reduce the manufacturing cost since multiple transducer (102) arrays in dice form may be fabricated in high volume and at low cost.

In some examples, the diameter of the wafer may range between 6~12 inches and many transducer (102) arrays may be batch manufactured thereon. Furthermore, in some examples, the control circuitry (FIG. 1, 109) for controlling the piezoelectric elements (104) may be formed such that each piezoelectric element (104) is connected to the matching integrated circuits, (e.g., receive channels (FIG. 1, 108) and transmit channels (FIG. 1, 106)) in close proximity, preferably within 25 µm-100 µm. For example, the transducer (102) may have 1,024 piezoelectric elements (104) and be connected to matching control circuitry (FIG. 1, 109)

that has the appropriate number of transmit and receive circuits for the 1,024 piezoelectric elements (104).

Each piezoelectric element (104) may have any suitable shape such as square, rectangle, and circle. As depicted in FIG. 5, in some examples, the piezoelectric elements (104) may be arranged in a two-dimensional array arranged in orthogonal directions. That is, the piezoelectric element (104) array may be an M×N array with N columns (542) and M rows (544).

To create a line element, a column (542) of N piezoelectric elements (104) may be effectively connected electronically. Then, this line element may provide transmission and reception of ultrasonic signals similar to those achieved by a single bulk piezoelectric element, where each of both electrodes for each piezoelectric element (104) are electronically connected to realize a column that is N times larger than each piezoelectric element (104). This line element may be called a column or line or line element interchangeably. An example of a column of piezoelectric elements (104) is shown in FIG. 5 by the reference number (542). Piezoelectric elements (104) are arranged in a column (542) in this example and have associated transmit driver circuits (part of transmit channel) and low noise amplifiers (LNAs) which are part of the receive channel circuitry. Although not explicitly shown, the transmit and receive circuitry include multiplexing and address control circuitry to enable specific elements and sets of elements to be used. It is understood that transducers (102) may be arranged in other shapes such as circles, or other shapes. In some examples, piezoelectric elements (104) may be spaced 250 μm apart from each other, from center to center. It should be noted that since the piezoelectric elements (104) are connected under programmed control, the number of piezoelectric elements (104) connected in a column, for example, is programmable.

For the transducer (102), a line element may be designed using a plurality of identical piezoelectric elements (104), where each piezoelectric element (104) may have its characteristic center frequency. When a plurality of the piezoelectric elements (104) are connected together, the composite structure (i.e. the line element) may act as a line element with a center frequency that consists of the center frequencies of all the element pixels. Using modern semiconductor processes used to match transistors, these center frequencies match well to each other and have a very small deviation from the center frequency of the line element. It is also possible to mix several pixels of somewhat different center frequencies to create a wide bandwidth line compared to lines using only one central frequency.

In some examples, the ASIC that is connected to transducers (102) may include one or more temperature sensors (546-1, 546-2, 546-3, 546-4) to measure the temperature in that region of the ASIC and transducer. While FIG. 5 depicts temperature sensors (546) disposed at particular locations, the temperature sensors (546) may be disposed at other locations and additional sensors may be disposed at other locations on the imaging device (FIG. 1, 100).

The temperature sensors (546) may be a trigger to the selective adjustment of channels (FIG. 1, 106, 108). That is, as described above, temperatures within a handheld portable imaging device (FIG. 1, 100) may rise above a predetermined temperature. The transducers (102) may be coated with a material to act as an interface between the transducer and the patient contact surface. In an example, the material serves as a backing layer disposed on a surface of the transducer facing the ASIC. The material may be a polydimethylsiloxane (PDMS), or other similar material, having an acoustic impedance that is in between the transducer and the tissue acoustic impedance levels for the frequencies of interest. The temperature sensors (546) detect a temperature of the device at a surface of the imager contacting the patient due to proximity to that area. If the temperature sensors (546) detect a temperature greater than a threshold amount, for example, a user-established temperature or a temperature set by a regulatory authority, a signal may be passed by the controller (FIG. 3, 324) to power down all or some of the transmit channels (FIG. 1, 106) and/or receive channels (FIG. 1, 108) or to set all or some of the transmit channels (FIG. 1, 106) and/or receive channels (FIG. 1, 108) in a low power state.

FIG. 5 also depicts the terminals of the piezoelectric elements (104). Particularly, each piezoelectric element (104) has two terminals. A first terminal is a common terminal shared by all piezoelectric elements (104) in the array. The second terminal connects the piezoelectric elements (104) to the transmit channels (FIG. 1, 106) and receive channels (FIG. 1, 108), where the transmit and receive channels may be on a different substrate. The second terminal is the terminal that is driven and sensed for every piezoelectric element (104) as shown symbolically for those piezoelectric elements (104) in the first column. For simplicity the transmit channels (106) and the receive channels (FIG. 1, 108) appear to be connected together. However, in some examples, they may be separately controlled to be active in transmit mode, in receive mode, or both operations, with wiring being more complex than shown here for simplicity. Also, for simplicity, the second terminal is only indicated for those piezoelectric elements (104) in the first column. However, similar terminals with the associated transmit channels (106) and receive channels (108) populate the other piezoelectric elements (104) in the array. The control circuitry (FIG. 1, 109), using control signals, may select a column (542) of piezoelectric elements (104) by turning on respective transmit channels (FIG. 1, 106) and receive channels (FIG. 1, 108) and turning off the channels (FIG. 1, 106, 108) in other columns (542). In a similar manner, it is also possible to turn off particular rows (54), or even individual piezoelectric elements (104).

Figure 6A:
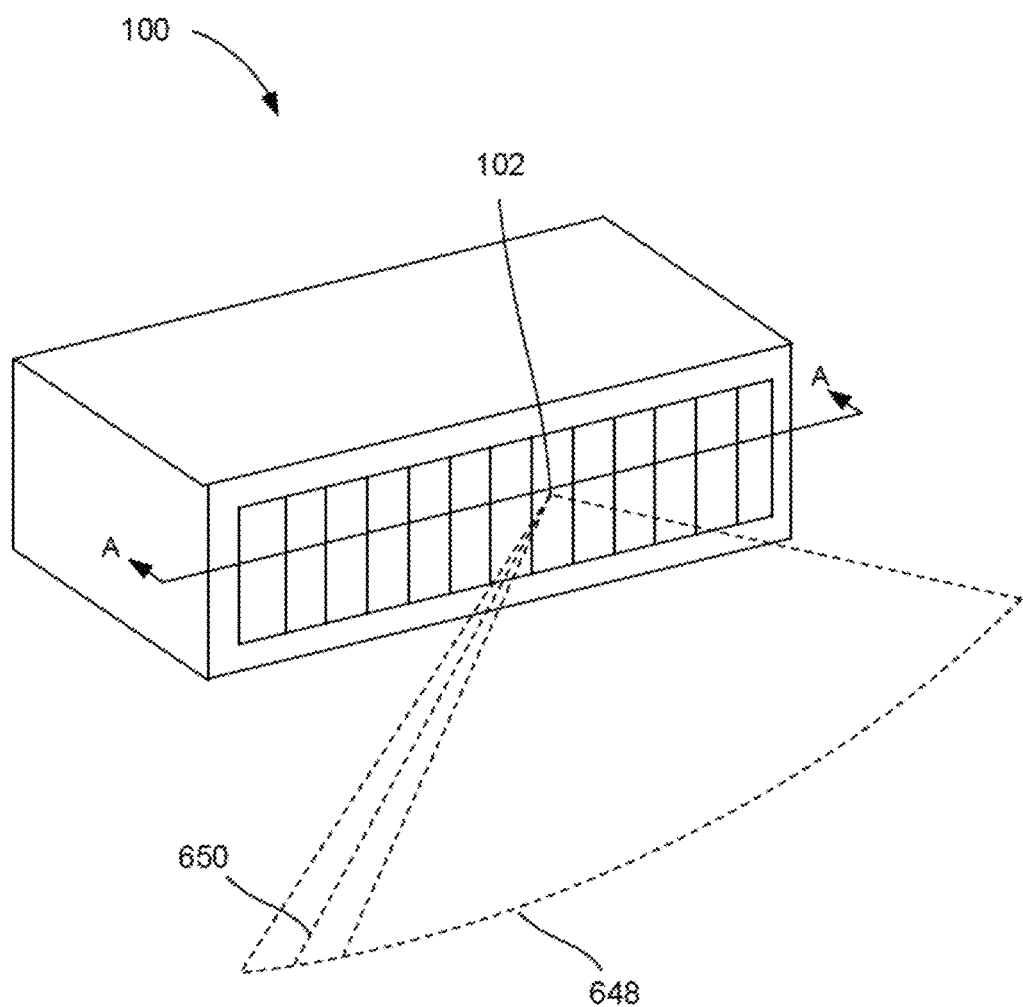
FIG. 6A illustrates an isometric view of an imaging device and scan lines of a frame, according to an example of the principles described herein.

FIG. 6A is an isometric view of an imaging device (100) and scan lines (650) of a frame (648), according to an example of the principles described herein. A frame (648) refers to a single still image of an organ, or other object to be imaged. The frame (648) may be a cross-sectional line through the object. A frame (648) is made up of individual scan lines (650). That is, a frame (648) may be viewed as an image, and a scan line (650) represents a portion of the frame (648) representing that image. Depending on the resolution, a particular frame (648) may include different numbers of scan lines (650) ranging from less than a hundred to many hundreds.

To form a frame (648), a transducer (102), using beam forming circuitry, transmits and focuses pressure waves from different piezoelectric elements (FIG. 1, 104), for example, those in a particular column or columns (FIG. 5, 542) to a particular focal point. The reflected signals collected by these piezoelectric elements (FIG. 1, 104) are received, delayed, weighted, and summed to form a scan line (650). The focal point of interest is then changed to a different part of the frame, and the process is repeated until an entire frame (648), consisting of, for example 100-200 scan lines (650), is generated.

While particular reference is made to a particular transmission technique, many different transmit techniques may be employed, including achieving multiple focus with a single transmission from multiple channels. Moreover, the operations described in the present specification are also applicable to these multi-focal transmit signaling techniques. Simultaneous multi-zone focusing can be achieved, for example, using chirp signaling and can help achieve better resolution as a function of depth. As a specific example, chirp signaling sends a coded signal during transmit where many cycles of frequency or phased modulated coded signals are transmitted. The received echo is then processed with a matched filter to compress the received signal. This method has the advantage of coupling larger energy into the target compared with situations when only 1 or 2 pulses are transmitted. While axial resolution may become worse when transmitting multiple signals, with chirp signaling, because of the matched filter in the receiver, axial resolution is largely restored.

An issue with chirp signaling is that it uses many cycles of transmit pulses which can increase power output for transmit pulses of similar amplitude for all signaling cases. However, by electronically adjusting the aperture in elevation, power output can be adjusted to allow various types of signaling used in B-mode and Doppler imaging, where many more pulses are used.

Figure 6B:
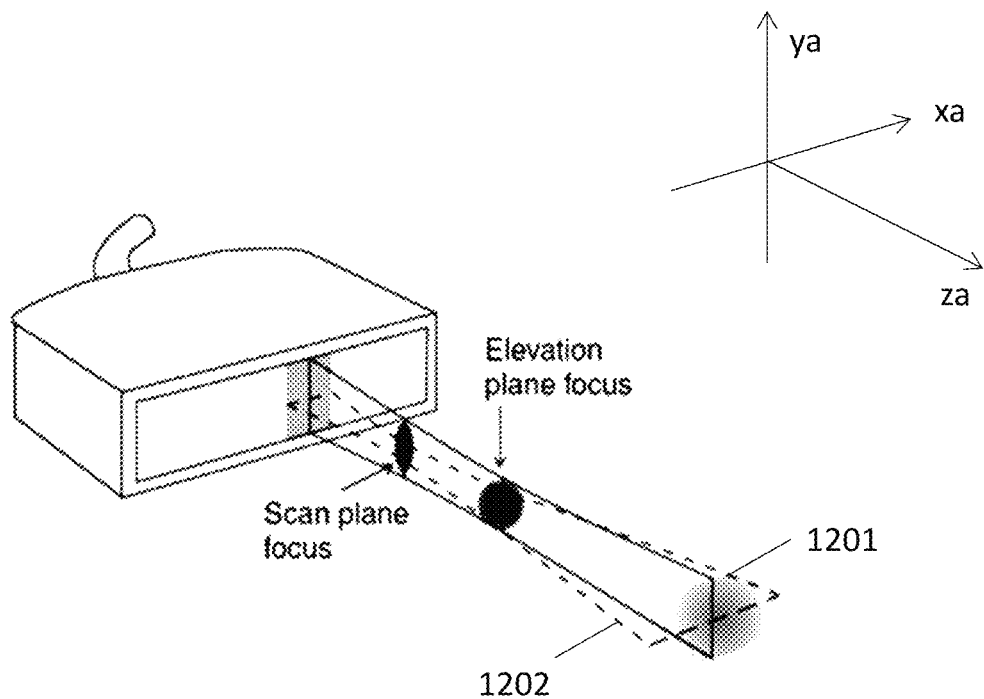
FIG. 6B illustrates azimuth (xa), elevation (ya) and axial/depth (za) directions.

FIG. 6B illustrates the azimuth axis, noted as direction xa. This is the same as direction A-A in FIG. 6A, with lines (650) in FIG. 6A being in the axial direction as shown in FIG. 6B and noted as za or depth in FIG. 6B. FIG. 6B also notes the elevation direction ya. The elevation direction may be particularly pertinent for 2D imaging. The ultrasonic beam as shown is focused in an elevation plane (1201) to concentrate the beam in a narrow direction and increase pressure in that plane at a specific point in the axial direction. The beam is also focused in the azimuth plane (1202) in the in the azimuth direction.

If the azimuth focal point and the elevation focal point are relatively at the same location, as shown in FIG. 6B, pressure at the target focal point increases. The ability to electronically control both elevation and azimuth focal points provides an operator to target any point in the elevation and axial dimension to create 3D focusing with increased pressure at that point. Increases in pressure increase signal availability to the transducer and also improves sensitivity. Further, if not focused in the elevation direction, the transmitted waveform can hit other objects away from the elevation plane (1201) and reflected signals from these unwanted targets would create clutter in the received image. Note that FIG. 6B shows the acoustic beam travelling in depth in the axial direction.

Figure 6C:
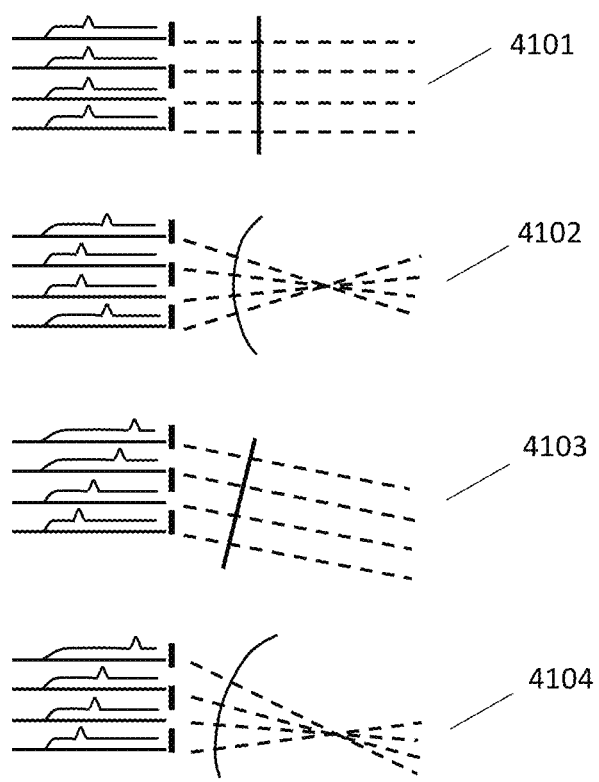
FIG. 6C illustrates beam focus and steering with changes in delay for elements on a column.

FIG. 6C illustrates various types of beam-reflecting elements arranged on a column with different delays applied to each element on the column. For example, a first beam (4101) has equal delays to all elements that cause waveforms to be delayed equally, resulting in a plane wave referred to as a synchronous beam. Other examples include different delays applied to elements on a column to focus a beam at a point. For a beam focused at a point in the elevation plane, this is referred to as steering the beam or focusing and steering the beam. A second beam (4102) illustrates a focused beam. A third beam (4103) illustrates a beam with beam steering and a fourth beam (4104) illustrates a beam with steering and focusing.

Figure 6D:
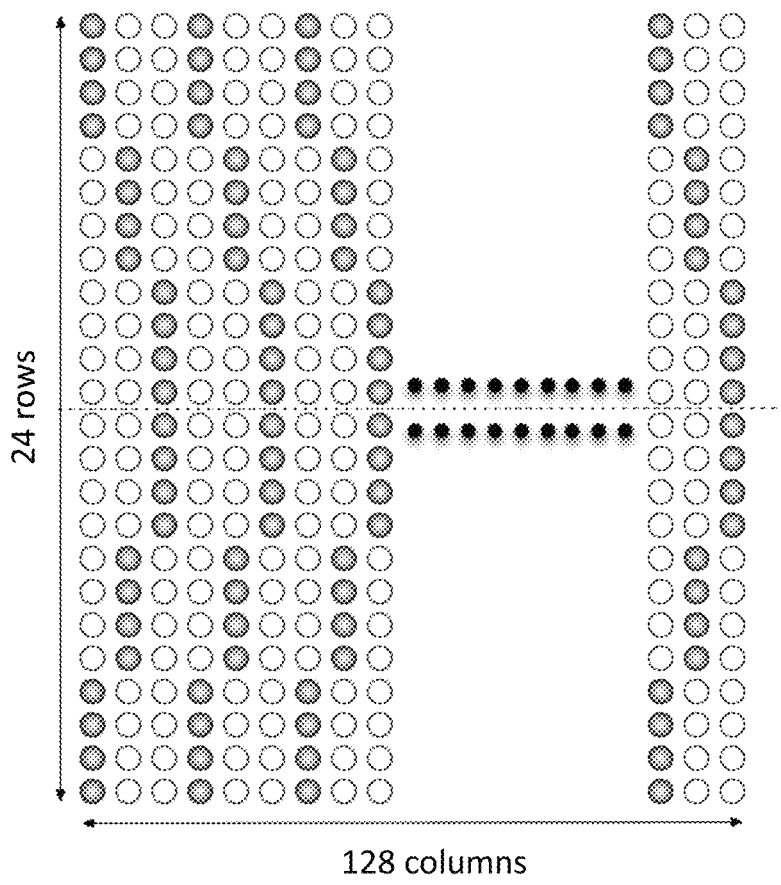
FIG. 6D illustrates a two-dimensional matrix of elements, where relative delays on columns are changed.

FIG. 6D illustrates an example of a transducer with 24 rows and 128 columns, where each column includes 24 elements. Elements indicated by circles in the columns share the same delay and are shaded, whereas other elements have different delays and are not shaded. Each column may have the same relative delay as elements of the other columns or each column may have different relative delays. The actual delay on any element is the summation of delay in the azimuth axis and in the elevation axis. Controls are implemented in an ASIC which creates pulse drives to the elements with the appropriate delay in transmit mode and in receive mode.

In one example, the imaging device includes transmit elevation focus that is achieved electronically. For example, electronic focus is achieved by changing relative delays of the beam transmitted by an element on a column by an ASIC. Digital registers in the ASIC are controlled by an external controller, wherein a desired transmit elevation focal depth is sent to the ASIC. A desired azimuth focal depth is sent to the ASIC by an external controller wherein the ASIC sets relative delay of elements. A desired azimuth focal depth is adjusted for curvature in a transducer, ASIC, or board. Elevation focus is adjusted electronically to include delay adjustments to compensate for curvature in the transducer. In another example, elevation focus is transmit elevation focus. Elevation focus also includes adjusting a receive elevation focus. A mechanical lens may be included that provides a fixed transmit and elevation focus, and wherein electronic elevation focus allows further electronic change in the elevation focus. Unit specific electronic adjustments of focal length of transducers may be used to enhance Doppler imaging sensitivity. Electronic adjustments may include adjustment for unit to unit variations in curvature in transducers.

Figure 7:
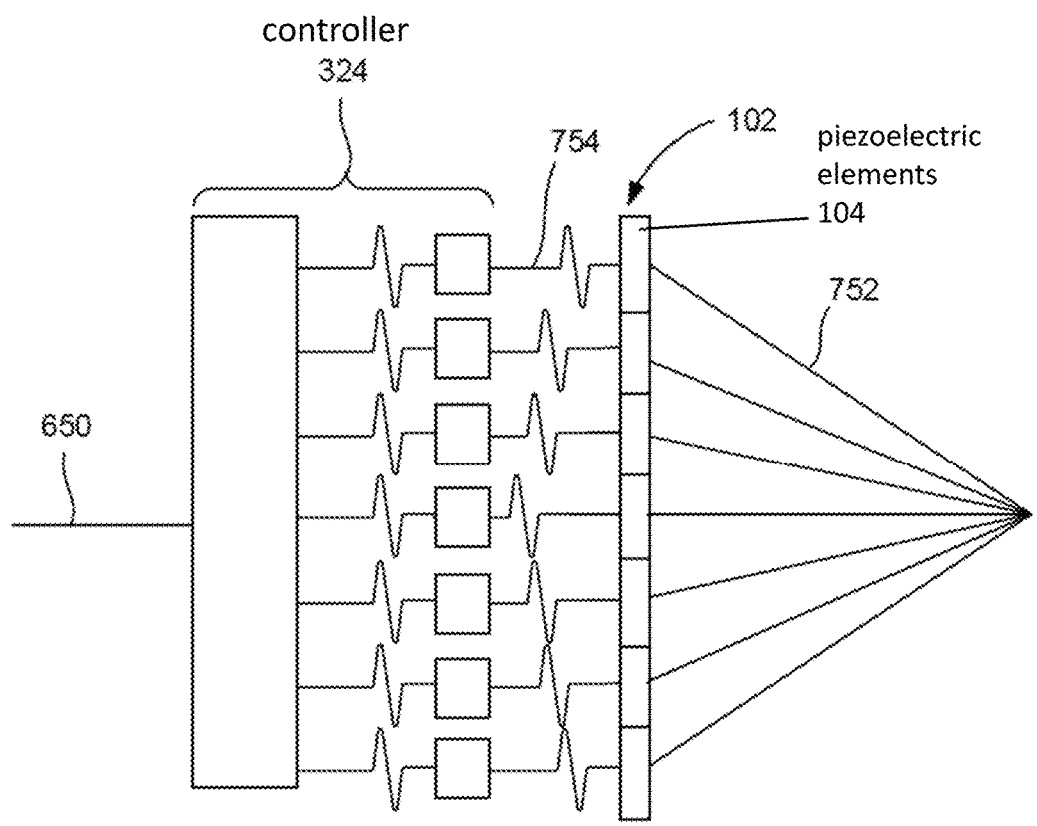
FIG. 7 illustrates the formation of a scan line, according to an example of the principles described herein.

FIG. 7 illustrates the formation of a scan line (650), according to an example of the principles described herein. A cross-sectional view of one transducer (102) is taken along the line A-A from FIG. 6A and includes the piezoelectric elements (104) that make up the transducer (102). In FIG. 7, just one piezoelectric element (104) of the transducer (102) is indicated with a reference number for simplicity. Moreover, note that the piezoelectric elements (104) depicted in FIG. 7 may represent a top piezoelectric element (104) of a column (FIG. 5, 542) with other piezoelectric elements (104) extending into the page. FIG. 7 also depicts circuitry that may be found in the controller (324) to form a scan line (650).

For simplicity, FIG. 7 only depicts seven piezoelectric elements (104), and seven respective columns (FIG. 5, 542). However, as described above, a transducer (102) may include any number of piezoelectric elements (104), for example, 128 columns (FIG. 5, 542), with each column (FIG. 5, 542) having 32 piezoelectric elements (104) disposed therein.

To form a scan line (650), signals (752) are received from a number of piezoelectric elements (104), such as from each piezoelectric element (104) in a column (FIG. 5, 542). In some examples, signals for piezoelectric elements (104) in a column (FIG. 5, 542) may be combined into a composite signal (754) which is passed to the controller (324). As each composite signal (754) is received at a different time due to different transmission lengths, the controller (324) delays each composite signal (754) such that they are in phase. The controller (324) then combines the adjusted signals to form a scan line (650). Additional detail regarding the processing of received signals (754) by the controller (324) are presented in later figures.

As described above, a frame (FIG. 6A, 648) of an image is formed of many scan lines (650), often 128 or more. These scan lines (650) cover the area to be imaged. The time to collect and combine the scan lines (650) into a frame (FIG. 6A, 648) defines the quality of the video, in terms of the frame rate, of an object to be imaged. For example, assuming the example of scanning a heart, and assuming the heart is 20 cm below the transducer (102) surface, an ultrasound waveform takes approximately 130 microseconds (us) to travel to the heart, assuming sound travels at 1540 m/s in tissue. The signal is then reflected from the heart and takes another 130 microseconds to reach the transducers (102) for a total transit time of 260 microseconds. Using N receive channels (FIG. 1, 108), one scan line (650) is formed by transmitting from N transmit channels (FIG. 1, 108) driving N columns (FIG. 5, 544) of piezoelectric elements (FIG. 1, 104) and receiving from all N columns (FIG. 5, 544) and processing the signals as indicated in FIG. 7. In an example, using 128 channels, one scan line is formed by transmitting from 128 channels, driving 128 columns of piezoelectric elements and receiving from all 128 columns and processing the signals. Assuming 128 scan lines (650) per frame (FIG. 6A, 648), the maximum frame rate is around 30 frames per second (fps).

In some examples, 30 fps may be sufficient, for example, with livers and kidneys. However, to image moving organs, such as a heart, a higher frame rate may be desired. Accordingly, the imaging device (FIG. 1, 100) may implement parallel beamforming where multiple scan lines (650) can be formed at the same time. As multiple scan lies (650) can be formed at a time, the effective frame rate may be increased. For example, if four scan lines (650) could be formed at the same time, then the effective frame rate may go up to 120 fps. Parallel beamforming may be implemented in a field programmable gate array (FPGA) or graphical processing unit (GPU) (FIG. 3, 326) of the imaging device (FIG. 1, 100).

In some examples, parallel beam forming is used to initially increase the frame rate, even if the rate is higher than needed. For example, with parallel beam forming, a frame rate of 120 fps may be achievable. However, if 30 fps is adequate, hardware such as transmit and receive channels can be enabled for a portion of time, such as one fourth of the time, cutting down power consumption by a factor of 4 or less. The time saving takes into account some requirements that are not amenable to being completely shut down, but that can be placed into a materially lower power state. For example, after a set of four scan lines are simultaneously collected, the transmit (FIG. 1,106), receive channels (FIG. 1, 108) and portions of the control circuitry (FIG. 1, 109) may be turned off for a period of time, and then turned on again to collect another four scan lines simultaneously.

Such techniques can reduce power consumption by larger factors, such as approximately 3.3 times less than a starting power consumption value for the example cited. In other words, parallel beam forming is employed to increase the frame rate. This is followed by a selective shutdown of circuitry involved in creation of scan lines to reduce power, with the shutdown times such that targeted frame rates are still achieved. This technique enables a reduction of power consumption compared with parallel beam formation not employing the circuitry. Such an operation does not affect the image quality as imaging artifacts can be digitally corrected with operations that are not power intensive and can be executed in a display processor that is not located in the probe. Particularly, data from the imaging device (FIG. 1, 100) in the form of scan lines (650) can be transported to the computing device (FIG. 2, 216) unit using a USB interface and image processing can be done outside of the imaging device (FIG. 1, 100) where there are less restrictions on temperature rise. The amount of scaling is dependent upon the number of parallel beams that are transmitted and received. For example, the scaling may be smaller when using two parallel beams or larger when using eight parallel beams.

Figure 8:
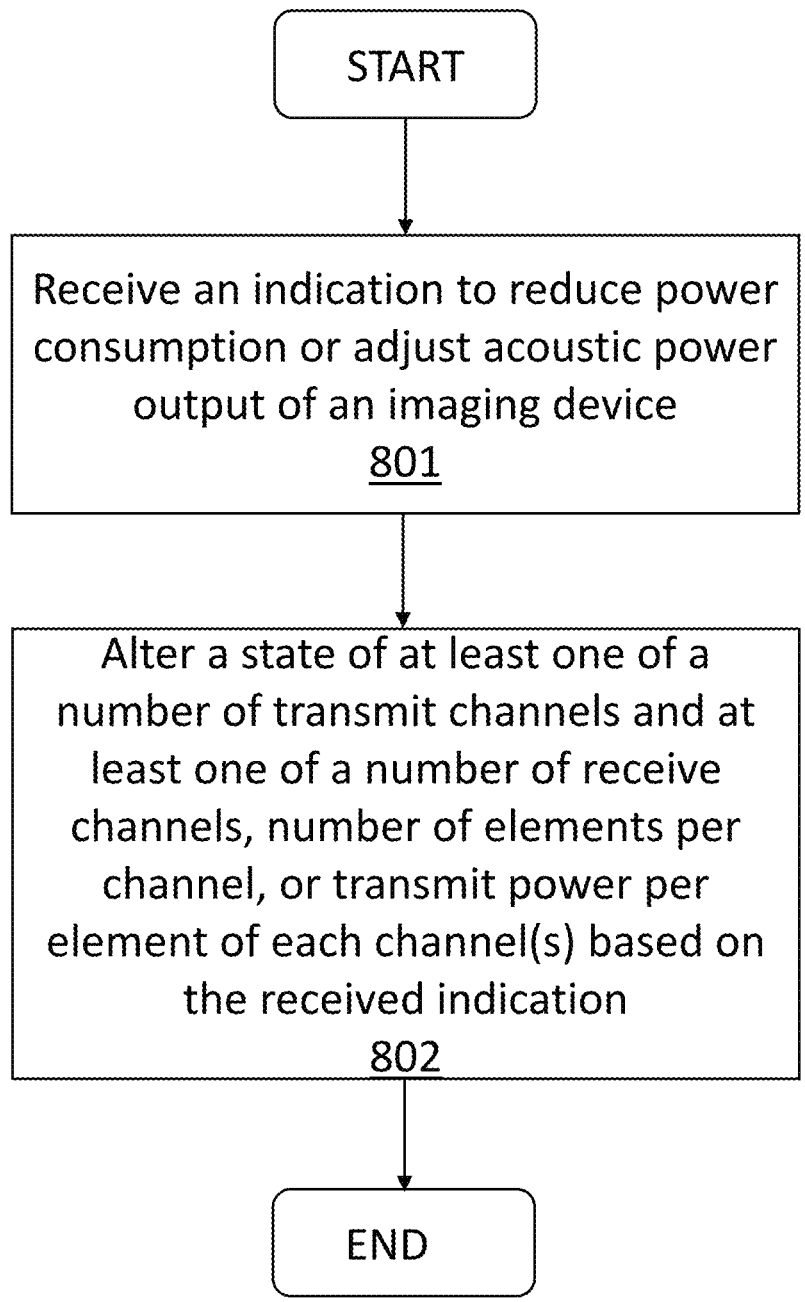
FIG. 8 illustrates a flowchart of a method for selectively altering a number of channels of an imaging device, according to an example of the principles described herein.

FIG. 8 is a flowchart of a method (800) for selectively altering a number of channels or number of elements per channel (FIG. 1, 106, 108) of an imaging device (FIG. 1, 100), according to an example of the principles described herein. According to the method (800), an indication is received (block 801) that power consumption or acoustic power output should be adjusted within the imaging device (FIG. 1, 100). The indication may come in a variety of forms. For example, if power consumption is to be reduced because temperature sensors indicate that temperature is too high, an indication to reduce power may be sent to the control circuitry. In another example, if the acoustic power output is to be altered, an indication may be received by the control circuitry to alter the number of elements transmitting or power per element. Accordingly, a state of at least one of a number of transmit channels and at least one of a number of receive channels, number of elements per channel, or transmit power per element of each channel(s) is altered (block 802) based on the received indication.

In an example, the imaging device (FIG. 1, 100) is first used to guide the operator to obtain a medically relevant image by helping to orient the imaging device (FIG. 1, 100) correctly. This may be accomplished by using artificial intelligence techniques that leverage machine learning with algorithms to guide the user to orient the image in the proper orientation for the desired view of the organ (FIG. 2, 214) being imaged. After the proper orientation is obtained, then the actual imaging session can start at a relevant resolution. However, during the orientation and guidance session, high resolution is not required and therefore the imaging device (FIG. 1, 100) can be set to a lower power and lower resolution mode, saving power for the overall imaging session.

Figure 9:
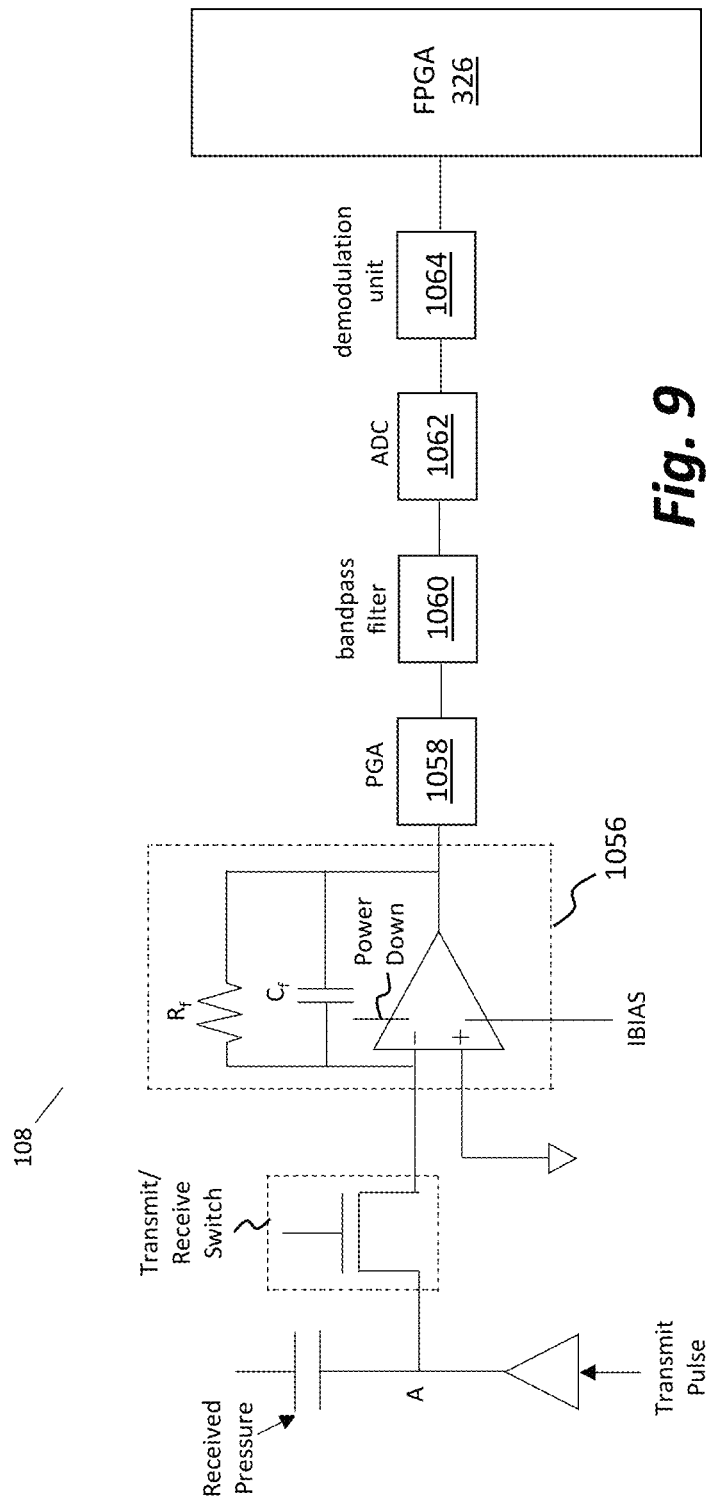
FIG. 9 illustrates a receive channel, according to an example of the principles described herein.

FIG. 9 depicts a receive channel (108), according to an example of the principles described herein. The receive channel (108) is coupled to a piezoelectric element (FIG. 1, 104) to receive the reflected pressure wave (FIG. 2, 210). FIG. 9 also depicts the connection between the piezoelectric element (FIG. 1, 104) and the transmit channel (FIG. 1, 106). During a transmit operation, the transmit/receive switch is off, isolating the LNA (1056) from the drive signal on node A. In one example, after transmission is complete, the transmit channel (FIG. 1, 106) pulse driver is set to a high impedance state to allow a pressure signal to be received by the transducer during a receive operation at the node (A in FIG. 9) where the received pressure signal is connected to the LNA by a transmit/receive switch which is now turned on. During transmit operations, the transmit pulse driver delivers a transmit signal, also at node A, which the transducer converts to an ultrasonic pressure wave and transmits to the target being imaged.

In other words, the receive channel (108) receives a reflected pressure waveform from the target to be imaged and the receive channel (108) converts the pressure to electrical voltage. Specifically, the reflected pressure wave is converted to an electrical charge in the transducer which is converted to a voltage by an LNA. The LNA is a charge amplifier, where charge is converted to an output voltage. In some examples, the LNA has programmable gain, where the gain can be changed in real time and controlled by $C_f$ and $R_f$, where $C_f$ and $R_f$ are a bank of programmable components as shown in FIG. 11. An example of an LNA (1056) with programmable gain is depicted in FIG. 10.

The LNA (1056) converts charge in the transducer to a voltage output and also amplifies the received echo signal. A transmit/receive switch connects the LNA (1056) to the transducer in the receive mode of operation.

The output of the LNA (1056) is then connected to other components to condition the signal. For example, a programmable gain amplifier (PGA) (1058) further adjusts the magnitude of the voltage and provides a way to change the gain as a function of time and may be known as a time gain amplifier. As the signal travels deeper into the tissue, it is attenuated. Accordingly, a larger gain is used to compensate, which larger gain is implemented by the TGC (time gain compensation). The bandpass filter (1060) operates to filter out noise from band signals. An analog-to-digital converter (ADC) (1062) digitizes the analog signal to convert the signal to the digital domain such that further processing can be done digitally. Data from the ADC (1062) is then digitally processed at a demodulation unit (1064) and passed to the FPGA (326) to generate the scan line (FIG. 6A, 650) as depicted in FIG. 7. In some implementations, the demodulation unit (1064) can be implemented elsewhere, for example in the FPGA (326). The demodulation unit (1064) frequency-shifts the carrier signal to baseband with two components in quadrature (I and Q), for further digital processing. In some examples, the ADC (1062) may implement a successive-approximation-register (SAR) architecture to reduce latency of the ADC (1062). That is, as the ADC (1062) is turned off and on repeatedly, it needs to have little to no latency so as to not delay signal processing following turning on.

Figure 10:
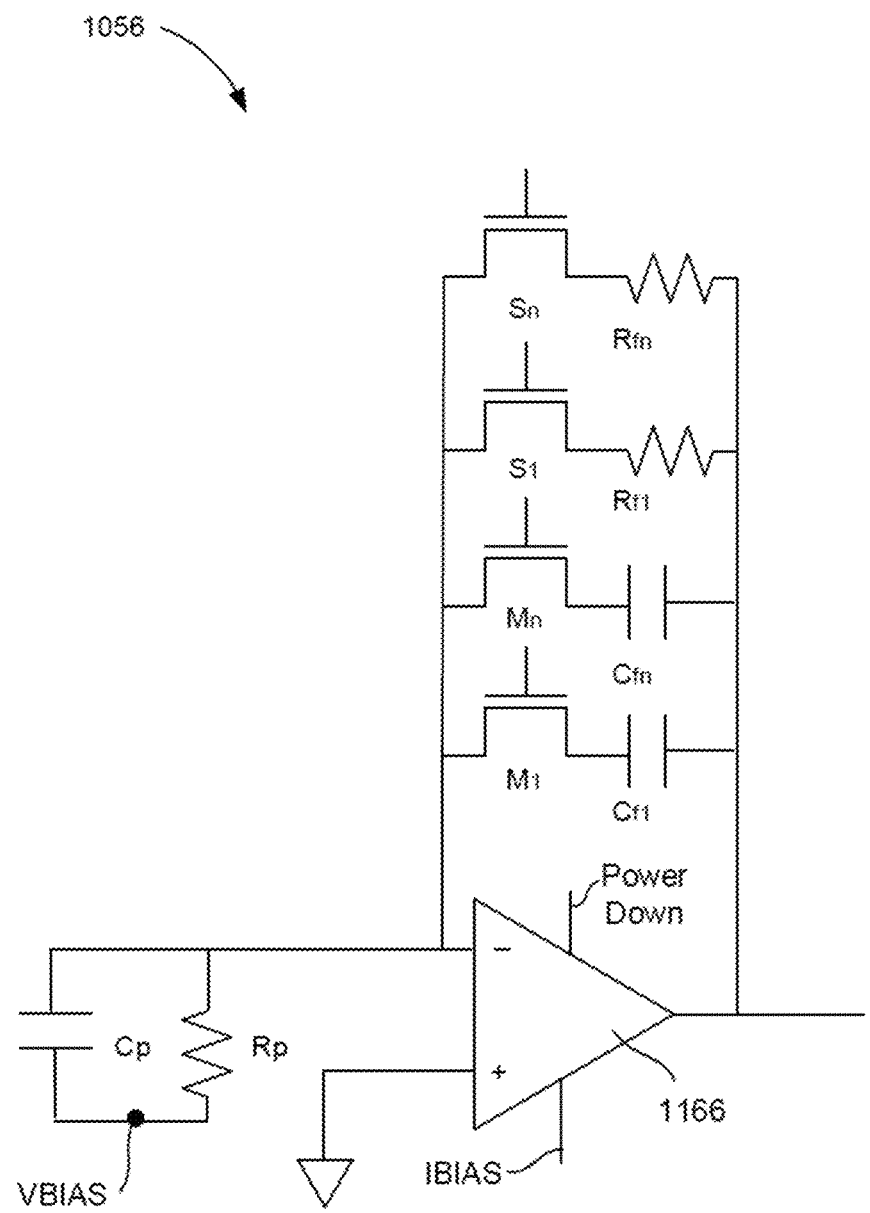
FIG. 10 illustrates a simplified schematic of a low-noise amplifier (LNA) of a receive channel, according to an example of the principles described herein.
Figure 11:
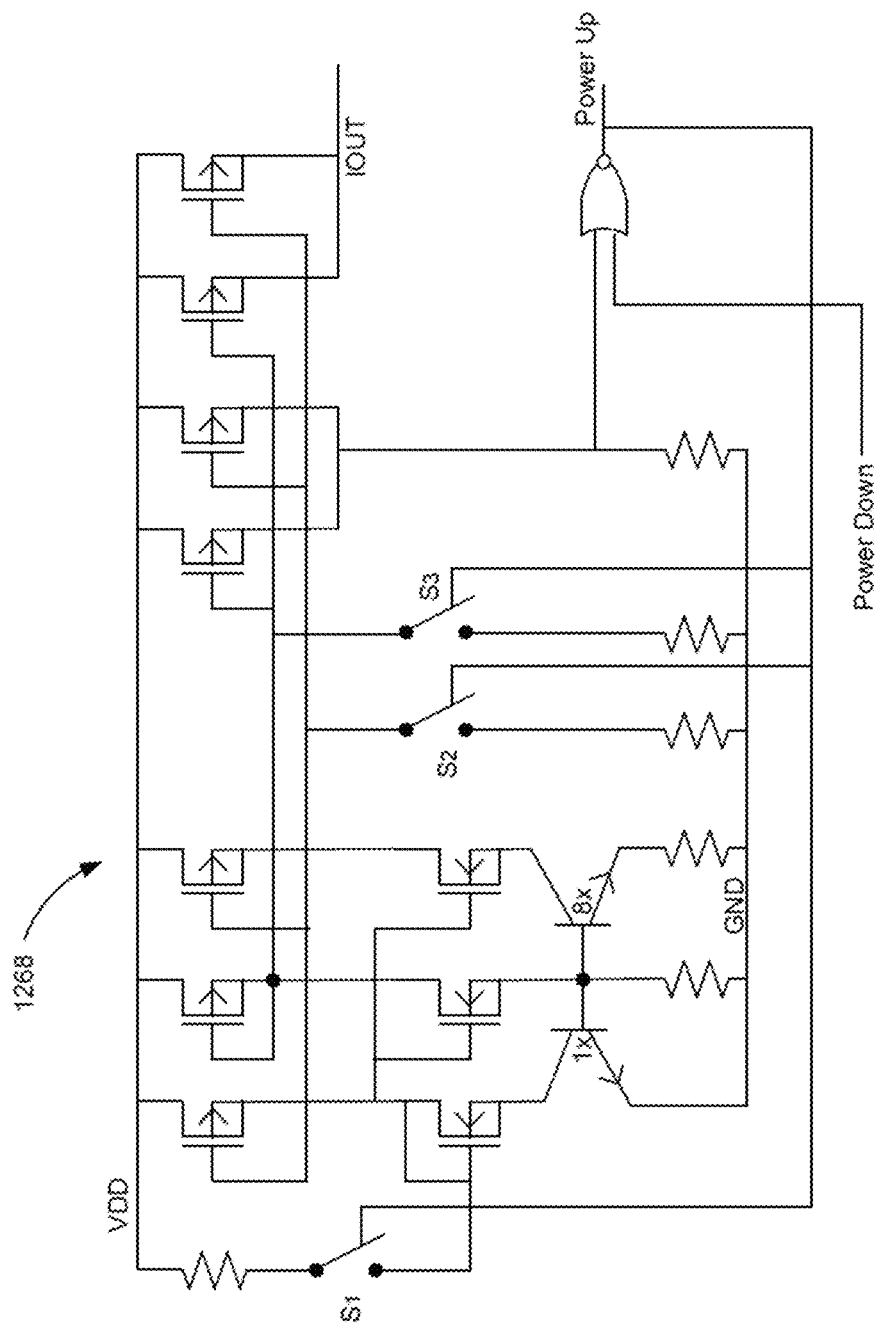
FIG. 11 illustrates a circuit diagram of a fast power-up biasing circuit, according to an example of the principles described herein.

FIG. 10 depicts a low-noise amplifier (LNA) (1056) of a receive channel (FIG. 1, 108), according to an example of the principles described herein. A bank of capacitors $C_{f1}$-$C_{fn}$ are electronically selected by turning on switches $M_1$-$M_n$ and are connected across an operational amplifier (1166). $R_{f1}$-$R_{fN}$ are a bank of resistors that are also electronically selected by turning on switches $S_1$-$S_N$. The signal gain is a ratio of the transducer capacitance $C_p$ divided by feedback capacitance $C_f$, where appropriate switches are turned on to connect $C_f$ and $R_f$ values from the bank as desired. A bias voltage (VBIAS) is used to provide a bias voltage such that the polarity of the field across the transducer does not change as a signal swings in a positive or negative manner on the opposite electrode of the transducer.

FIG. 10 also depicts a bias current input (IBIAS). IBIAS may be generated by the circuit depicted in FIG. 11. IBIAS is used to change the transconductance of the LNA (1056), where a higher current level reduces noise level. Additionally, a digital input indicating power down is used to shut down the LNA (1056). To achieve fast power up, IBIAS needs to be established quickly with an example implementation shown in FIG. 11.

FIG. 11 illustrates a circuit diagram of a fast power-up biasing circuit (1268), according to an example of the principles described herein. As described above, when the receive channel (FIG. 1, 108) is powered on and off multiple times during operation, components can be rapidly turned on and off in order to ensure proper dissipation of heat and proper operation of the imaging device (FIG. 1, 100). In this example, the IOUT terminal is coupled to the IBIAS of the LNA (FIG. 10, 1056) so as to ensure that the LNA (FIG. 10, 1056) is quickly powered up. In order to implement the imaging device (FIG. 1, 100) effectively, the components in the signal path such as the LNA (FIG. 10, 1056) and the ADC (FIG. 10, 1064) in each receive channel (FIG. 1, 108) are able to shut down in around hundreds of nanoseconds and also be powered up in around 1 us. The fast power-up biasing circuit (1268) depicted in FIG. 11 is one example of providing such a quick power-up and shutdown. The biasing circuit (1268) depicted in FIG. 11 exhibits fast turn on and turn off times. If the Power Down signal is high, then Power Up bootstrap is low, turning off switches $S_1$-$S_3$, so that they do not conduct current and reducing the value of IOUT so as to effectively turn it off. When Power Down goes to low, (i.e., it is desired to power up the LNA (1056)), both inputs of the NOR gate are at low and this creates a high logic signal at Power Up bootstrap. This turns on the switches $S_1$-$S_3$ and restores current to IOUT rapidly. IOUT provides a current output whose value is copied in other circuits such as the LNA (FIG. 10, 1056) to power these circuits. The value of IOUT is close to zero during power down and has a higher value, typically in the tens or hundreds of μA, during power up.

Figure 12:
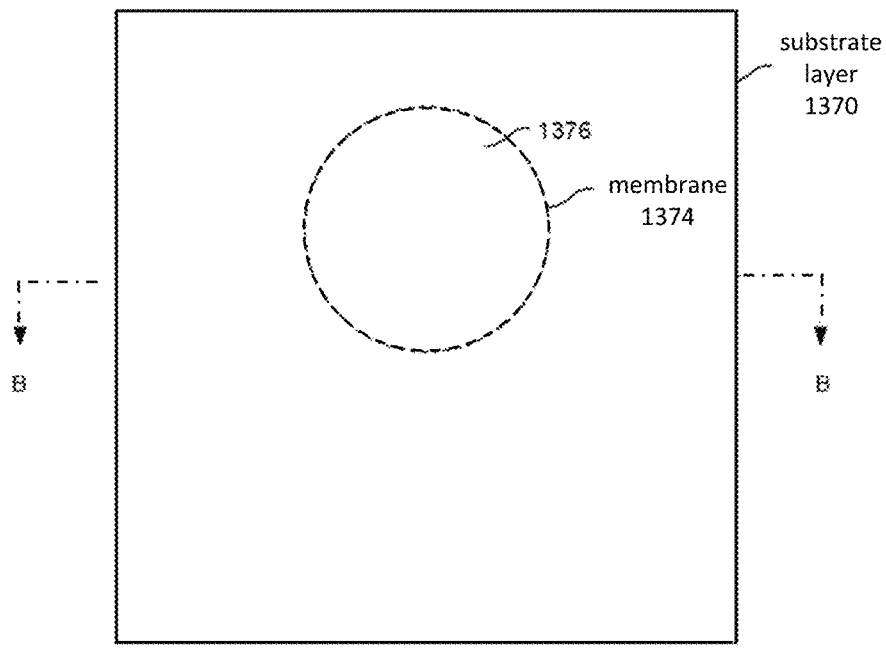
FIG. 12 illustrates the fabrication of a piezoelectric element, according to an example of the principles described herein.
Figure 13:
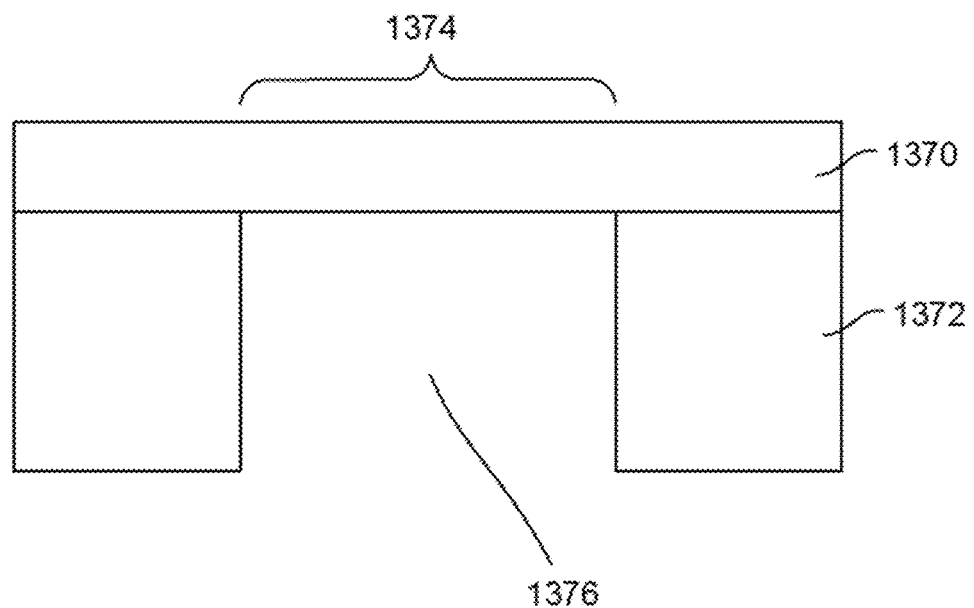
FIG. 13 illustrates the fabrication of a piezoelectric element, according to an example of the principles described herein.

FIGS. 12-16 illustrate the fabrication of a piezoelectric element (FIG. 1, 104), according to an example of the principles described herein. FIG. 12 shows a top view of a membrane (1374) disposed on substrate layers (1370) and (1372). FIG. 13 shows a cross-sectional view of the membrane (1374) and substrate (1372), taken along the line B-B in FIG. 12.

Figure 14:
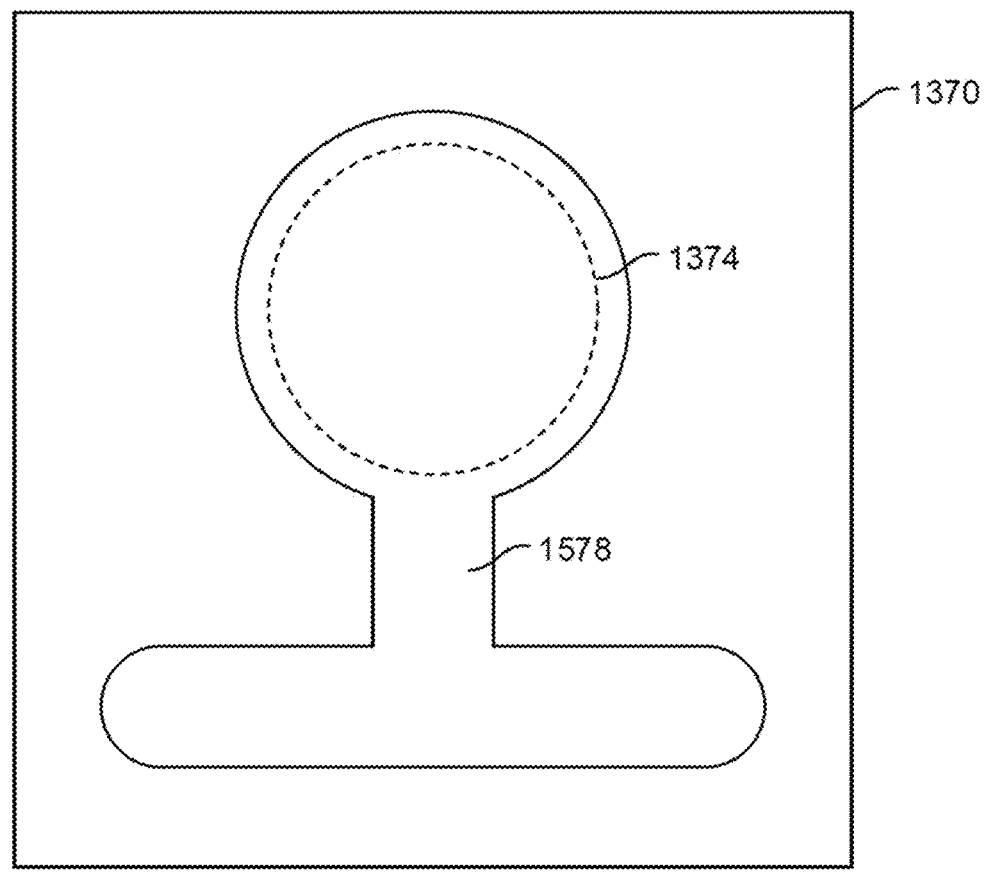
FIG. 14 illustrates the fabrication of a piezoelectric element, according to an example of the principles described herein.
Figure 15:
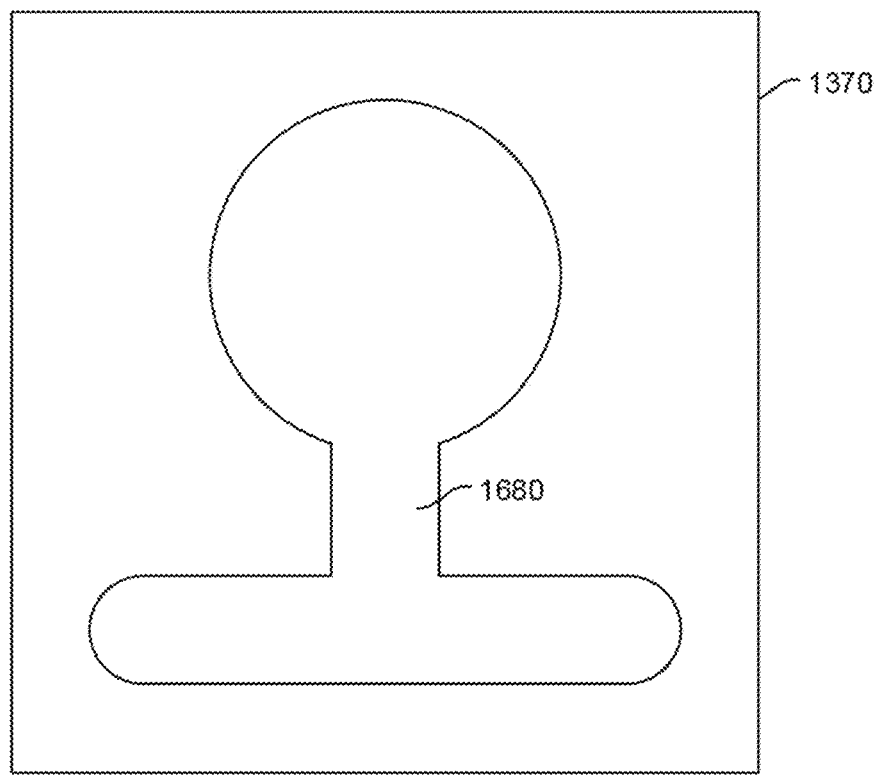
FIG. 15 illustrates the fabrication of a piezoelectric element, according to an example of the principles described herein.

FIG. 14 illustrates a top view of a bottom electrode (1578) disposed on a substrate layer (1370) and arranged over the membrane (1374) according to an example of the principles described herein. FIG. 15 shows a top view of a piezoelectric layer (1680) disposed on the bottom electrode (FIG. 14, 1578) according to an example of the principles described herein. In some examples, the piezoelectric layer (1680) may have a similar projection area as the bottom electrode (1578) so that the piezoelectric layer (1680) may cover the entire portion of the bottom electrode (1578).

Figure 16:
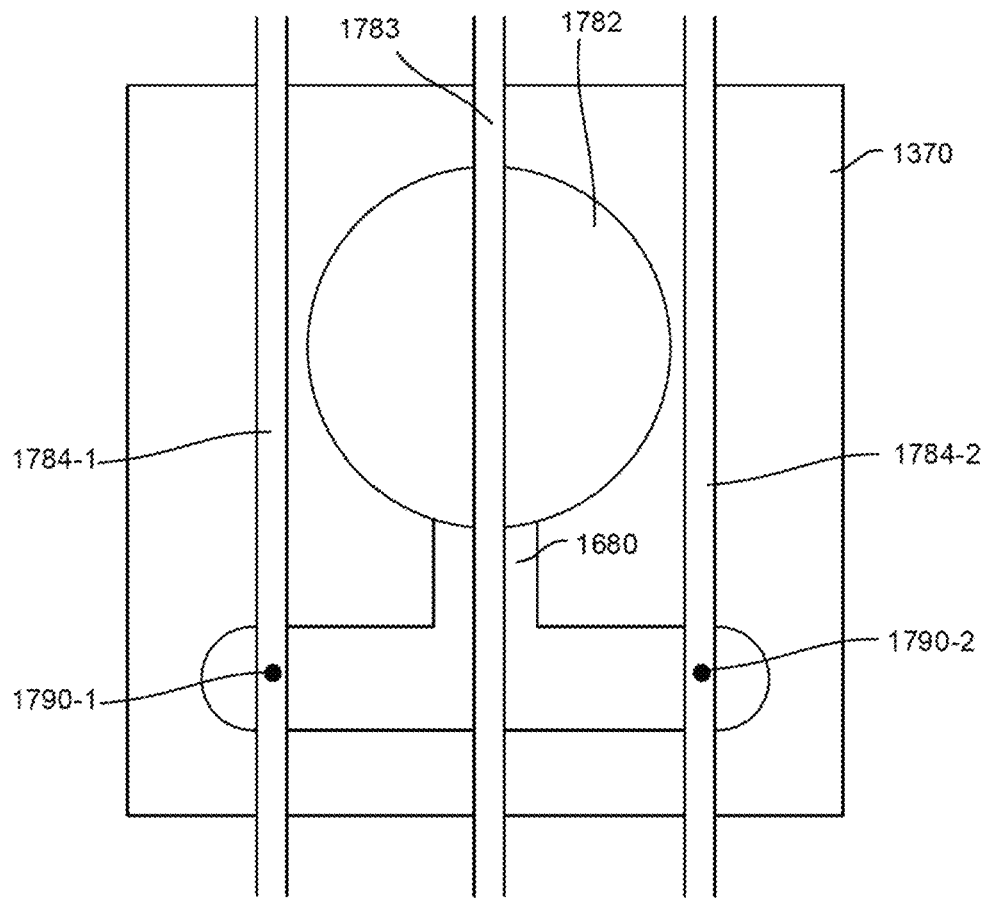
FIG. 16 illustrates the fabrication of a piezoelectric element, according to an example of the principles described herein.

FIG. 16 illustrates a top view of a piezoelectric element according to an example of the principles described herein. As depicted, a top electrode (1782) is disposed on the piezoelectric layer (1680) and arranged over the membrane (FIG. 13, 1374). In some examples, a top electrode conductor (1783) may be disposed on and electrically coupled to the top electrode (1782), while bottom electrode conductors (1784-1) and (1784-2) may reach the bottom electrode (1578) through one or more vias (1790-1, 1790-2). In this example, the top electrode (1782), the piezoelectric layer (1680) and the bottom electrode (1578) form a two terminal piezoelectric element and the membrane (1374) vibrates when an electrical voltage is applied across the top and bottom electrodes (1782, 1578). The electrical charge may be developed across the top and bottom electrodes (1782, 1578) when the membrane (1374) is deformed by a pressure wave (FIG. 2, 210) during a receive mode/process.

Figure 17A:
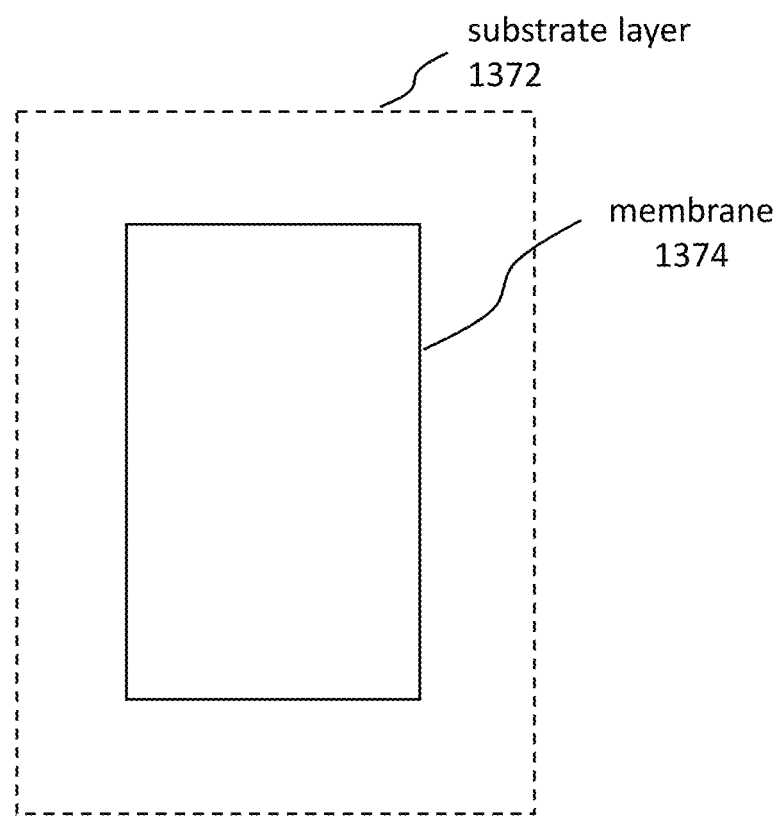
FIG. 17A illustrates element construction for isolation to reduce cross talk between neighboring elements.
Figure 17B:
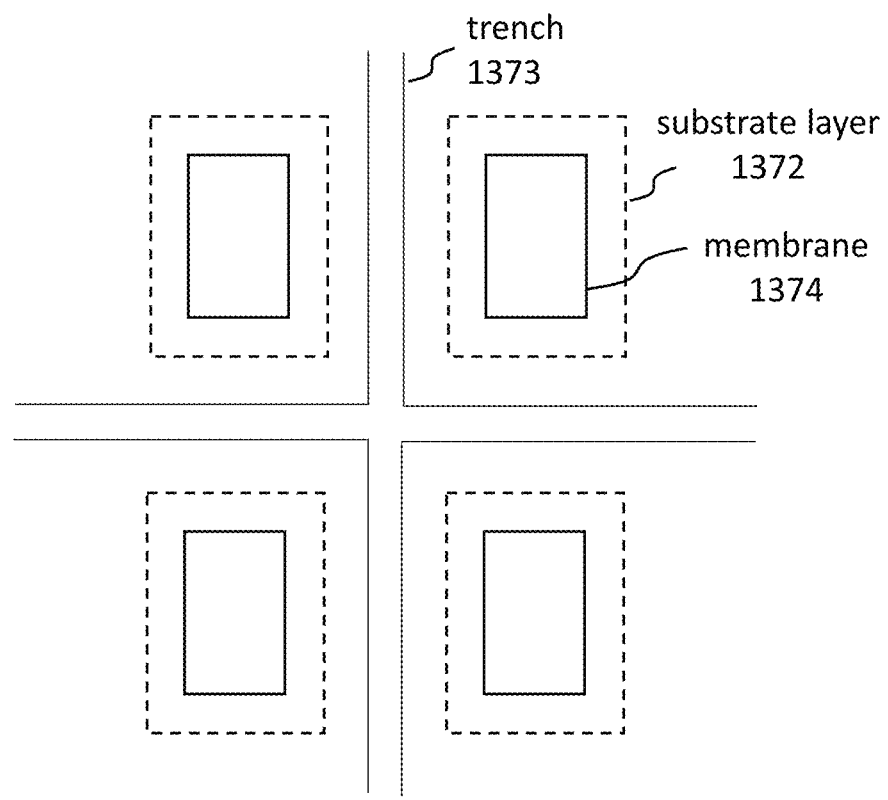
FIG. 17B illustrates element construction for isolation to reduce cross talk between neighboring elements.

The substrate (1372) may be thinned to obstruct cross talk between adjacent piezoelectric elements, where the thinner material does not support travel of the ultrasound waves in the substrate (1372) between activated elements or sub-elements. FIGS. 17A-17B illustrate element construction to achieve isolation and reduce cross talk between neighboring elements. The substrate (1372) may correspond to the transceiver substrate (540) in FIG. 5. As depicted, a membrane (1374) may be formed on the substrate (1372) with a cavity (1376) (see FIG. 13) formed by removing a portion of the substrate (1372), to thereby form the membrane (1374) that may vibrate relative to the substrate (1372) in the vertical direction. The cavity (1376) may be formed by wafer processing techniques, such as etching, for example, deep reactive ion etching (DRIE). The substrate (1372) may be formed of the same material as the membrane (1374). In another example, the substrate (1372) may be formed of a different material from the membrane (1374). The cavity (1376) (see FIG. 13) may be formed after the other components of the piezoelectric element (FIG. 1, 104), are formed. While FIG. 13 and others herein depict the membrane (1374) as having a circular projection area, the membrane (1374) may have other suitable geometrical shapes.

In particular, FIG. 17A illustrates the membrane (1374) formed on substrate (1372), where a cavity (1376) resides below the membrane (1374). The membrane (1374) is surrounded by substrate (1372) material on all sides. FIG. 17B illustrates four membranes (1374) with substrate (1372) separating them. It may be desirable to isolate the piezoelectric elements (FIG. 1, 104) from each other to minimize cross talk. Cross talk is the influence that a piezoelectric element (FIG. 1, 104) can have on another piezoelectric element (FIG. 1, 104) through acoustic or mechanical or electrical coupling. Such coupling is generally undesirable, as it makes each membrane (1374) less independent. In some examples, piezoelectric elements (FIG. 1, 104) are separated by a groove or trench (1373) cut in the substrate (1372) and that attenuates signals travelling towards its neighbors as shown in FIG. 17B. The trench (1373) can be filled by air or be a vacuum. This presents a discontinuity in impedance between adjacent areas and attenuates energy flowing from a piezoelectric element (FIG. 1, 104) towards its neighboring piezoelectric element (FIG. 1, 104). It is understood that even if some diagrams do not show this trench, it is incorporated by reference per this explanation.

Figure 17C:
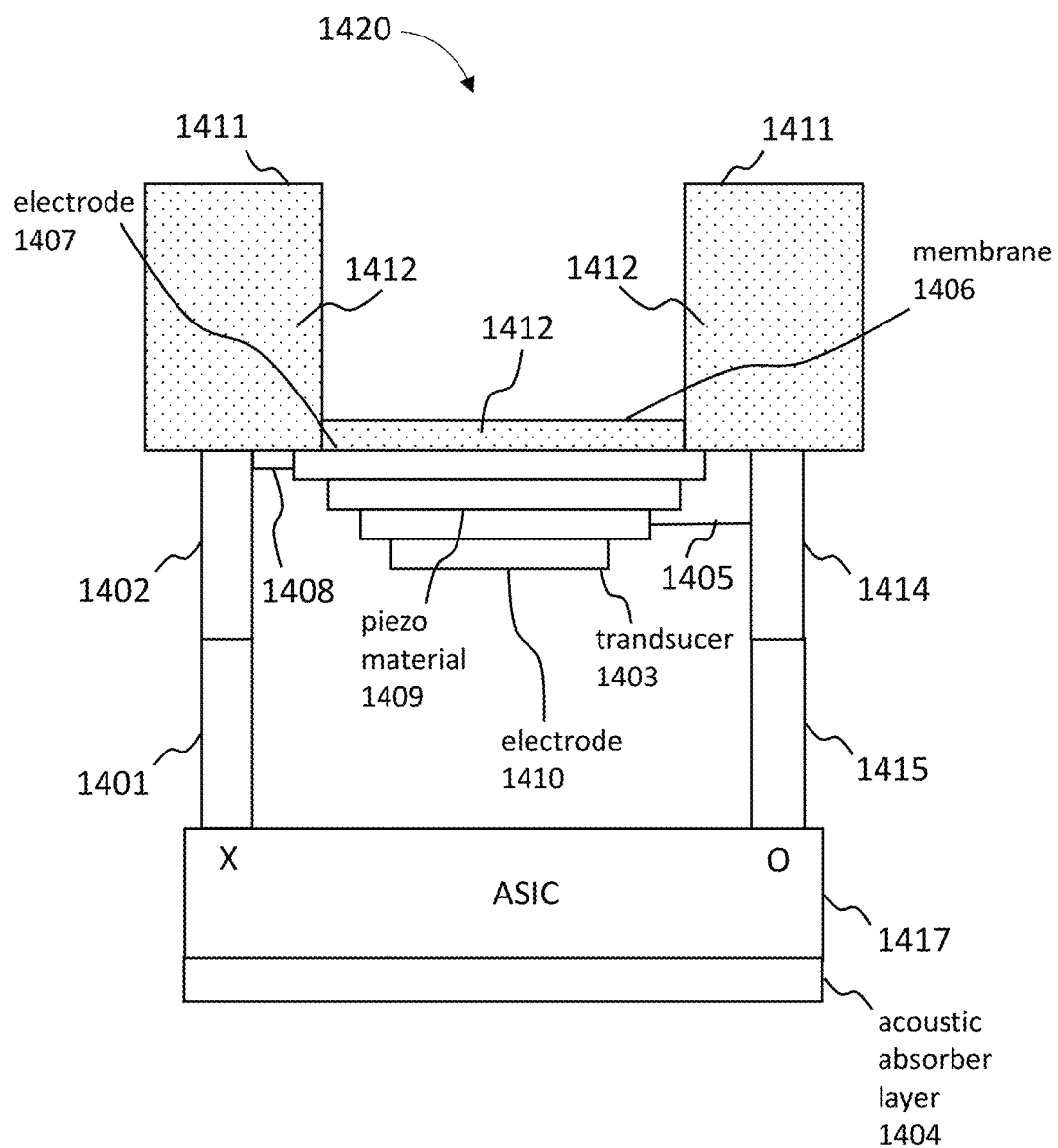
FIG. 17C illustrates a cross-sectional view of a transducer element connected to a corresponding application-specific integrated circuit (ASIC) with at least transmit drivers and receive amplifier electronics in the ASIC.

FIG. 17C depicts transducer elements connected to electronics using two connection points labeled X and O. Transducer (1420) includes substrates (1411), membrane (1406), piezo material (1409), another material or coating attached to transducer surface (1403), and electrodes (1407) and (1410). A first electrode (1407) is connected with wire (1408) to pillar (1402). Piezo material (1409) is disposed on electrode (1407). A second electrode (1410) is disposed on top of piezo material (1409) and connected with a wire (1405) to pillar (1414). An ASIC (1417) is shown below the transducer (1420) and connected to the transducer (1420) by two pillars (1401) and (1415) for every element of the transducer (1420). Pillars (1401) and (1402) are connected to a common terminal of elements known as X node, which is connected to a DC bias voltage. The transmit or receive terminal of the element is known as O node. Pillars (1414) and (1415) are attached to connect the transducer (1420) to the ASIC O node. Pillars (1401) and (1402) are connected together to integrate an element of transducer (1420) to related electronics in an ASIC (1417).

Similarly, pillars (1414) and (1415) are connected together to integrate an element of the transducer (1420) to related electronics in the ASIC (1417). The space between the transducer (1420) and the ASIC (1417) may be air-filled or a vacuum. The surface of transducer (1420) facing the ASIC (1417) may have a layer of coating (1403) to absorb or attenuate acoustic energy travelling in the direction of the ASIC (1417) from the transducer (1420). Additionally, an acoustic absorber layer (1404) can be attached below the ASIC (1417) as shown to absorb acoustic energy travelling from the transducer (1420) through the ASIC (1417). The region covering the substrate (1411) and membrane (1406) (i.e., in the cavity area and entire surface of the substrate 1411) is filled with impedance matching material (1412) making up the interface between the transducer (1420) and the target to be imaged. In some cases, the material under the membrane (1406) is made with a different acoustic impedance compared to material in the remaining part of the substrate (1411). This mismatch in impedance can also disrupt the possible acoustic coupling between neighboring elements or sub-elements as acoustic energy travels through the impedance matching layer.

In some examples, the piezoelectric elements (FIG. 1, 104) have a suspended membrane associated with them that vibrates at a center frequency and several other frequencies when exposed to stimulus at that frequency and as such behave like resonators. There is a selectivity associated with these resonators, known as a Q factor. For ultrasound imaging devices (FIG. 1, 102), Q may be usually designed to be low (close to one) and achieved by a combination of design of the pixels and loading applied to the pixels in actual use. The loading may be provided by application of a layer of RTV or other material to the surface of the piezoelectric elements (FIG. 1, 104), where the loading may also facilitate closer impedance matching between the transducer surface emitting and receiving the pressure waves and the human body part being imaged. The low Q and the well-matched center frequency may allow the line element to essentially act like a line imaging element with substantially one center frequency. Loading may also include a matching layer below the transducers, where the emitted waveform is absorbed by an acoustic absorber.

Figure 18:
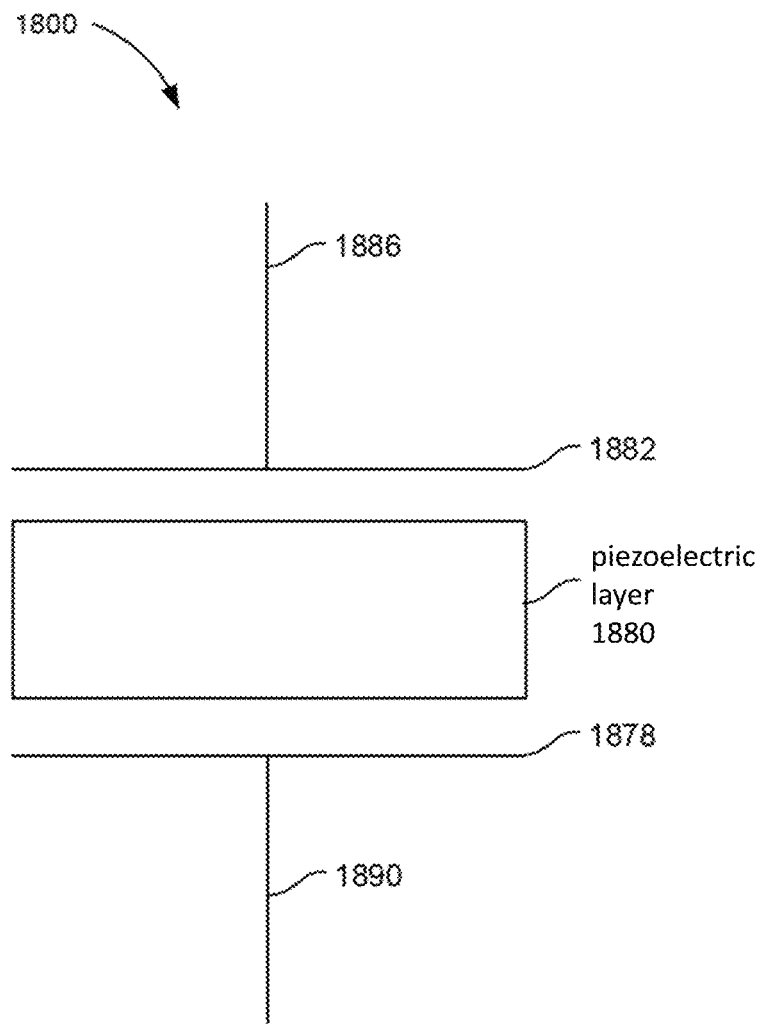
FIG. 18 illustrates a top view of a bottom electrode disposed on a substrate layer and arranged over a membrane, according to an example of the principles described herein.

FIG. 18 illustrates a schematic diagram of a piezoelectric element (1800), according to an example of the principles described herein. A piezoelectric layer (1880) is disposed between a first electrode (1882) and a second electrode (1878). The first electrode (1882) may be connected to a ground or a DC bias via a first conductor (1886) and the second electrode (1878) may be connected to an electrical circuit (not shown in FIG. 18) through a second conductor (1890).

In the conventional piezoelectric elements, the piezoelectric layer is thick, approaching around 100 μm and typically an AC voltage of +100 to −100 V across the piezoelectric layer is required to create an ultrasonic pressure wave of sufficient strength to enable medical imaging. The frequency of the AC drive signal is typically around the resonating frequency of the piezoelectric structure, and typically above 1 MHz for medical imaging applications. In conventional systems, the power dissipated in driving the piezoelectric element is proportional to $f*C*V^2$, where C is capacitance of the piezoelectric element, V is the maximum voltage across the piezoelectric layer, and f is frequency with which drive is being done. Typically, when transmitting pressure waves, multiple piezoelectric lines are driven together with somewhat different phase delays to focus the pressure waves or to steer a propagation direction of the pressure waves.

In the piezoelectric element (1800) of the present specification, the piezoelectric layer (1880) may be much thinner, for example 1-5 μm thick. This large reduction in thickness enables the use of lower voltage drive signals for the piezoelectric element (1800), where the voltage is lowered approximately by the amount by which the thickness of the piezoelectric layer (1880) is lowered to maintain the similar electric field strength. For example, the voltage potential across the two electrodes (1882) and (1878) may range from around 1.8 V to 40 V peak to peak. The capacitance of the piezoelectric element (1800) may increase due to the reduction in thickness of the piezoelectric layer (1880) for similar piezoelectric material. For instance, when the drive voltage is decreased by a factor of 10 while the thickness of the piezoelectric layer (1880) is also decreased by a factor of 10, the capacitance increases by a factor of 10 and the power dissipation decreases by a factor of 10. This reduction in power dissipation also reduces heat generation and temperature rise in the piezoelectric element (1800). Thus, using lower drive voltages and thinner piezoelectric layers, compared to the conventional piezoelectric elements, power consumption is lowered and this also lowers temperature of the piezoelectric element (1800) in operation.

Figure 19A:
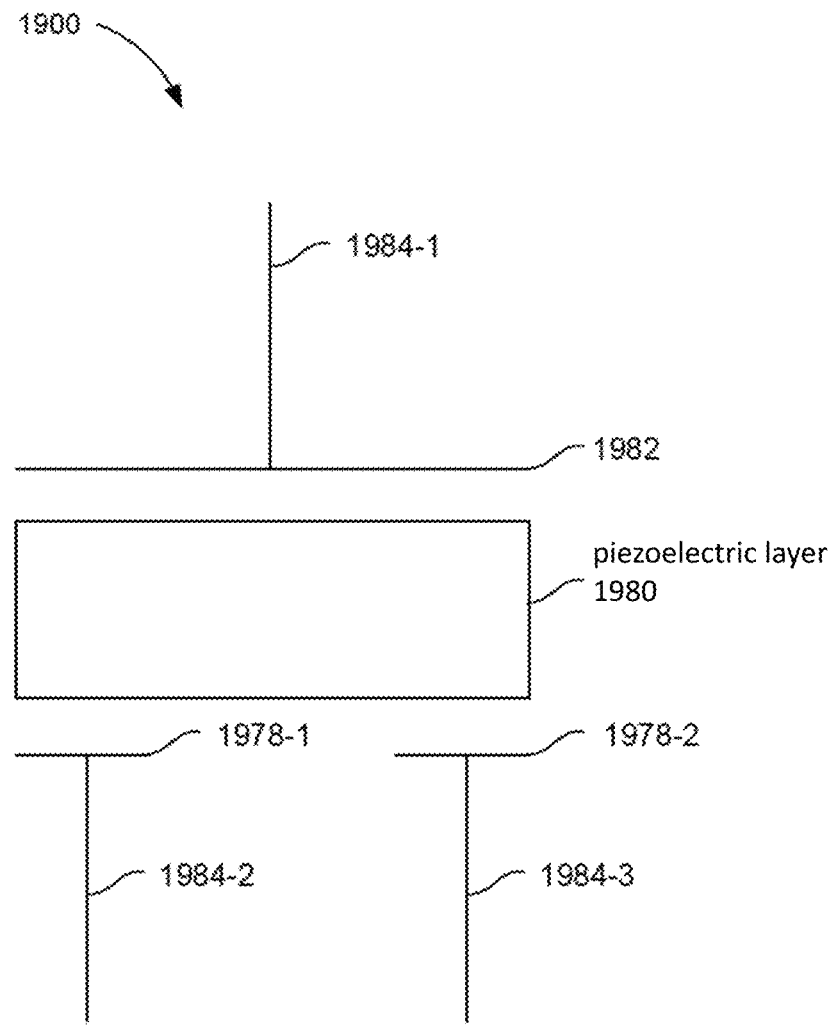
FIG. 19A illustrates a schematic diagram of a piezoelectric element, according to another example of the principles described herein.
Figure 19B:
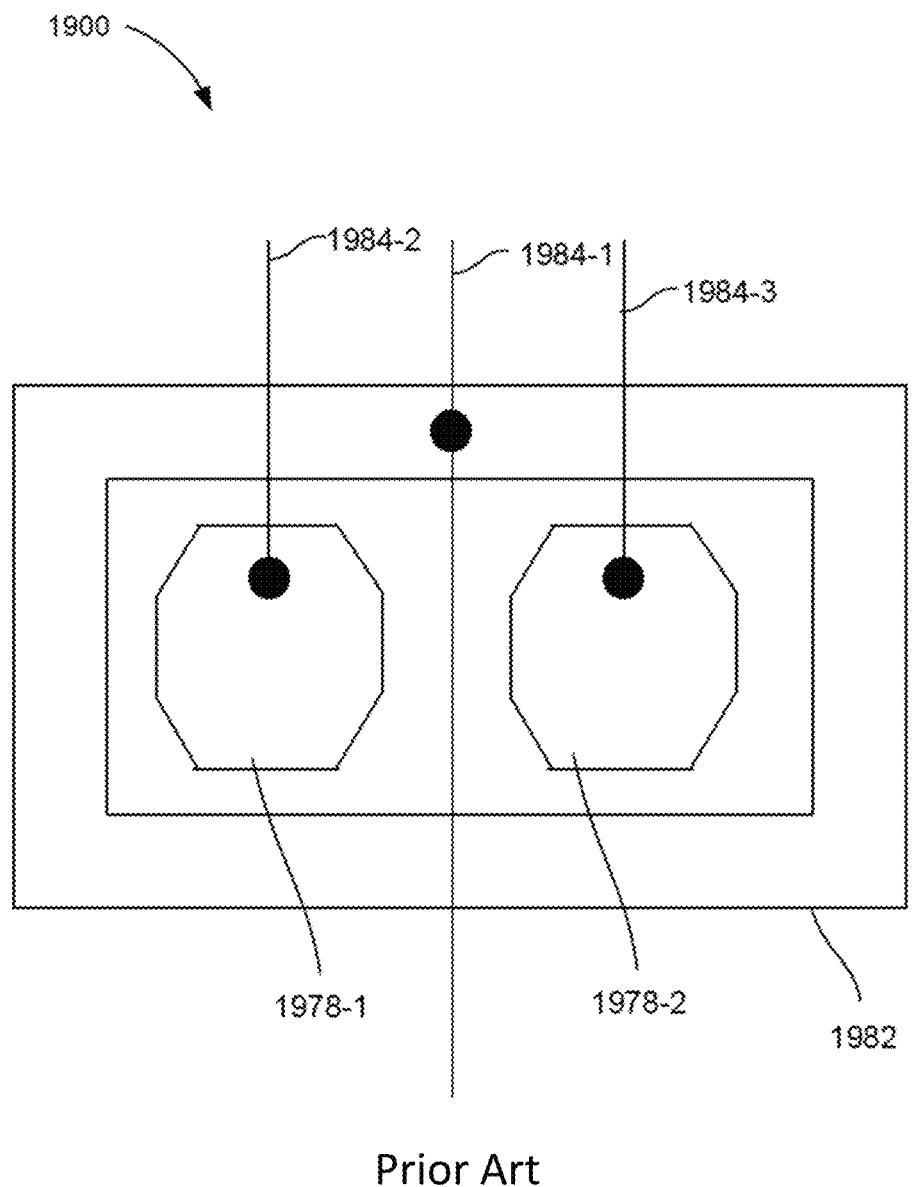
FIG. 19B illustrates a symbolic representation of the piezoelectric element of FIG. 19A, according to an example of the principles described herein.

FIG. 19A is a schematic diagram of a piezoelectric element (1900), according to another example of the principles described herein. FIG. 19B shows a symbolic representation of the piezoelectric element (1900) in FIG. 19A. As depicted, the piezoelectric element (1900) is similar to the piezoelectric element (1800), with the difference that the piezoelectric element (1900) has more than two electrodes. More specifically, the piezoelectric element (1900) includes: a top electrode (1982), a first bottom electrode (1978-1); a second bottom electrode (1978-2); a piezoelectric layer (1980) disposed between the top and bottom electrodes; and three conductors (1984-1), (1984-2), (1984-3) that are electrically coupled to the top and bottom electrodes (1982), (1978-1), (1978-2), respectively. Hereinafter, the terms top and bottom merely refer to two opposite sides of the piezoelectric layer, i.e., the top electrode is not necessarily disposed over the bottom electrode.

The piezoelectric element (1900) depicted in FIG. 19A is particularly helpful to increase sensitivity of transmit and receive operations. For example, when a piezo material is manufactured, the dipoles in the piezo material are not aligned and for optimal piezo performance, a poling process is implemented where a strong electric field is applied across the piezo film at high temperature (such as 175° C.). This establishes the direction of the electric field for later operations. However, if a piezo sub-element used for basic transmit and receive operation has poling done in orthogonal directions, its sensitivity can be enhanced. For a receive pressure wave, the piezo sub-element forms more charge signal on receive operations and for a given transmit voltage drive, more pressure is created.

The piezoelectric element (1900) in FIG. 19A includes 3 leads, where a first lead (1984-1) can be grounded during a poling operation, a second lead (1984-2) can be at a high voltage, say positive 15V, and a third lead (1984-3) can be at −15V. Accordingly, an orthogonal electric field is established in the sub-elements of piezoelectric element (1900) during this poling operation. During actual use, the second lead (1984-2) and third lead (1984-3) can be tied to DC bias voltages and act as a virtual ground while the first lead (1984-1) is used for transmit and receive operations.

While a unimorph piezoelectric element is shown in FIG. 19A purely for the purpose of illustration, in embodiments, a multilayer piezoelectric element composed of a plurality of piezoelectric sublayers and electrodes can be utilized. In embodiments, the piezoelectric layer (1980) may include at least one of PZT, PZT-N, PMN-Pt, AlN, Sc—AlN, ZnO, PVDF, and LiNiO3.

FIG. 19B illustrates a symbolic representation of the piezoelectric element of FIG. 19A, according to an example of the principles described herein.

Figure 19C:
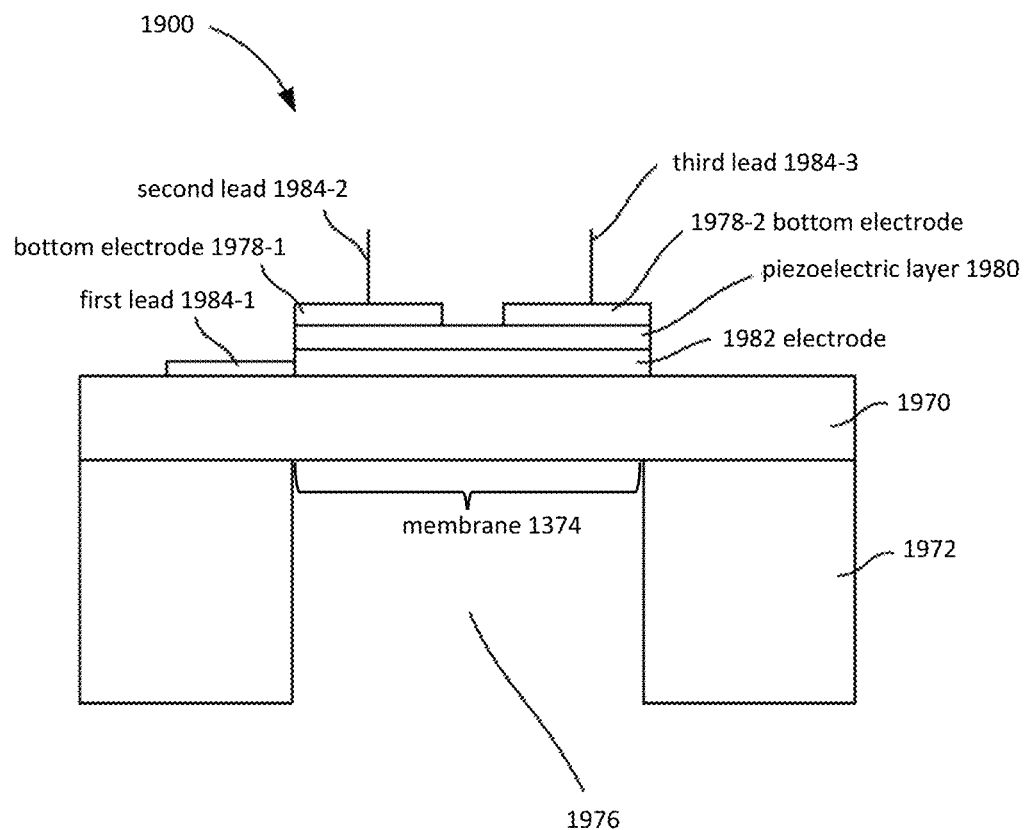
FIG. 19C illustrates a cross-sectional view of a piezoelectric element, according to an example of the principles described herein.

FIG. 19C illustrates a schematic cross-sectional view of a piezoelectric element (1900), according to an example of the principles described herein. The piezoelectric element (1900) may be disposed on a substrate layer (1970). Substrate layer (1972) along with substrate layer (1970) constitutes a substrate. A cavity (1976) may be formed in the substrate layer (1972) to define a membrane (1374). The membrane (1374) is the portion of the substrate layer (1970) that overlaps with the cavity (1976) with a shape similar to the cavity (1976). The substrate layers (1972) and (1970) may be made from the same material and moreover may be formed from a single continuous material.

The piezoelectric element (1900) may include a piezoelectric layer (1980) and a first electrode (1982) that is electrically connected to a top electrode conductor (1984-1). The top electrode conductor (1984-1) may be formed by depositing TiO₂ and metal layers on the membrane (1374).

A first bottom electrode (1978-1) may be grown above the piezoelectric layer (1980) and electrically connected to a first bottom conductor (1984-2). A second bottom electrode (1978-2) may also be grown above the piezoelectric layer (1980) and disposed adjacent to the second bottom conductor (1984-3) but be electrically isolated from the first bottom conductor (1984-2). The second bottom electrode (1978-2) and second bottom conductor (1984-3) may be formed by depositing one metal layer on the piezoelectric layer (1980) and patterning the metal layer. In some examples, the projection areas of the electrodes (1984) may have any suitable shape, such as square, rectangle, circle, ellipse, etc.

The first electrode (1982) may be electrically connected to the conductor (1984-1) using a metal, a via and interlayer dielectrics. In some examples, the first electrode (1982) may be in direct contact with the piezoelectric layer (1980). The second bottom conductor (1978-2) may be deposited or grown on the other side of the piezoelectric layer (1980) with respect to the first electrode (1982).

Figure 19D:
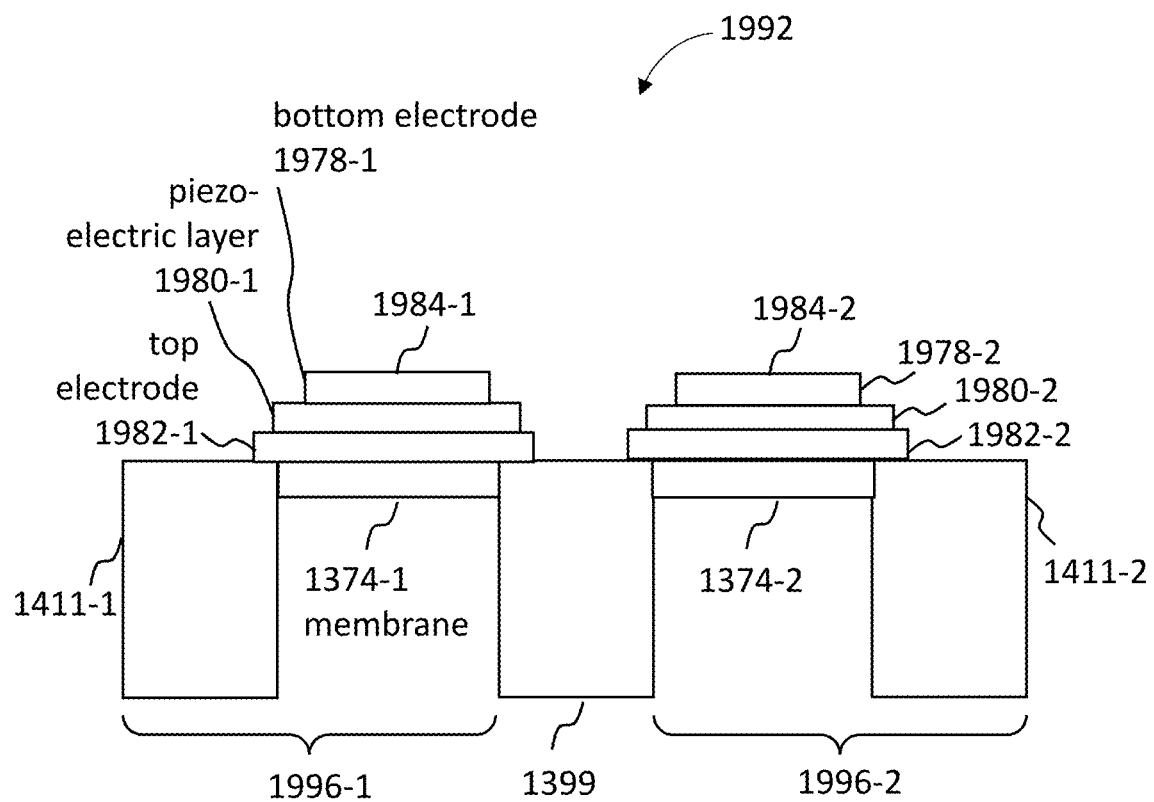
FIG. 19D illustrates a cross-sectional view of two sub-elements disposed on a substrate, according to an example of the principles described herein.

FIG. 19D illustrates a schematic diagram of a piezoelectric element (1992), according to another example of the principles described herein. As depicted, the piezoelectric element (1992) includes two sub piezoelectric elements (also referred to as sub-elements) (1996-1) and (1996-2). Sub-elements (1996-1) and (1996-2) are contiguous, making the space efficient.

Each sub-element (1996-1) and (1996-2) may include a two terminal device. For example, sub-element (1996-1) as shown includes one top electrode (1982-1), one bottom electrode (1978-1), one membrane (1374-1), and one piezoelectric layer (1980-1) The designation of top or bottom does not physically designate that one is above another, but is used to indicate that electrodes are at different vertical locations and top and bottom is used interchangeably. The other sub-element (1996-2) has one top electrode (1982-2), one bottom electrode (1978-2), and one piezoelectric layer (1980-2) (see Id.). Each sub-element (1996-1) and (1996-2) may be disposed on a respective separate membrane (1374-1) and (1374-2). Membranes (1374-1) and (1374-2) are separated by a solid area (1399) made of solid matter such as silicon dioxide. When sub-elements (1996-1) and (1996-2) are active, they can influence the behavior of each other or a neighboring sub-element. This can happen by transfer of energy from one sub-element to another sub-element or one element to another element. Such transfer can take place, for example, by ultrasonic waves travelling from sub-element (1996-1) to sub-element (1996-2) through the solid area (1399) or vice versa. It is beneficial to minimize such an interaction to minimize cross talk.

Figure 19E:
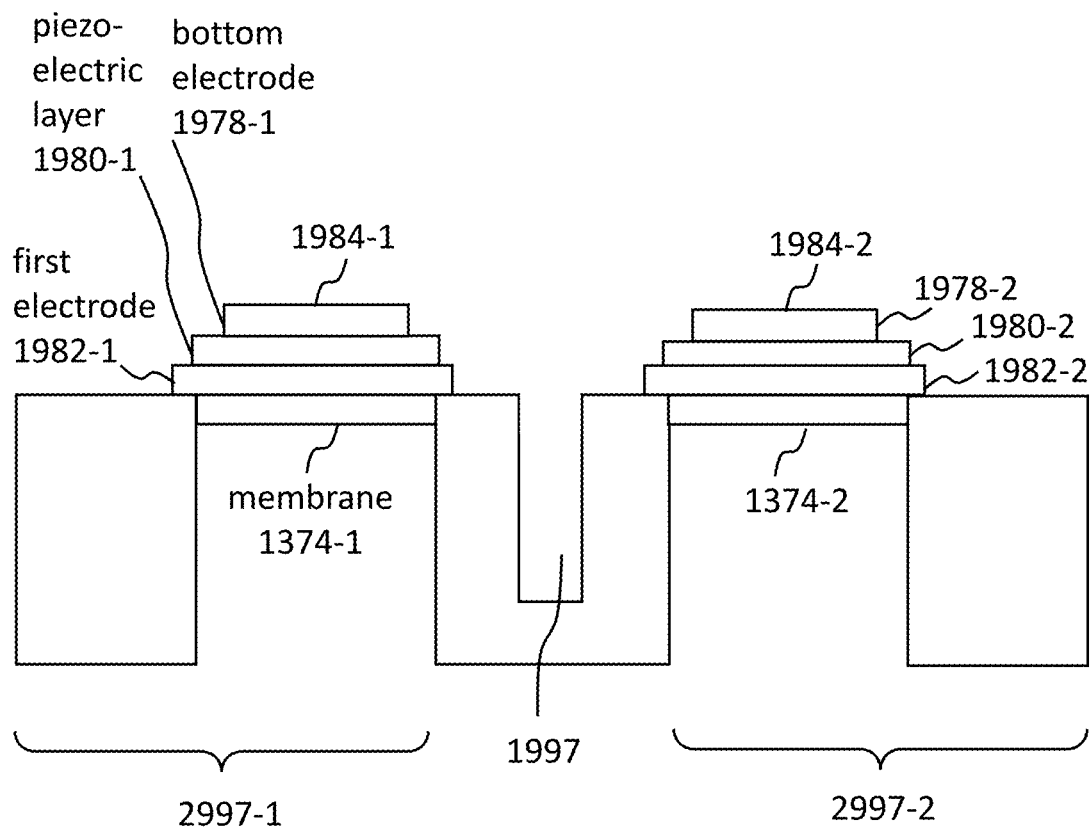
FIG. 19E illustrates a cross-sectional view of two adjacent elements showing details of piezo layers, conductors and means of isolation, according to an example of the principles described herein.

One example of reducing cross talk is via trenches such as trench (1997) shown in FIG. 19E. The trench (1997) can be air-filled or a vacuum (e.g, by incorporating a cover over the trench)). A trench may be used for sub-elements (1996-1) and (1996-2) in FIG. 19D to reflect cross talk causing wavefronts to return. Further cross talk minimizing techniques may also be implemented. For example, an impedance matching layer (not shown) may be applied over the transducer surface and the solid area (1399) to cause them to have a different acoustic impedance compared to material over membrane areas 1374. This disrupts acoustic waves travelling from one sub-element to another through the acoustic medium in the impedance matching layers.

Ultrasonic waveforms traveling in solids may reflect back from the trenched areas and prevent or reduce forward propagation of the waveform in the trench areas. It should be apparent to those of ordinary skill in the art that the conductors (like 1984-1, 1984-2, and 1984-3) may be connected to respective electrodes (1978-1) and (1978-2), using metals via interlayer dielectrics (ILD), and so on, in a similar manner as the piezoelectric element illustrated in FIGS. 12-16. For simplicity, all conductor connections are not shown.

Sub-elements (1996-1) and (1996-2) may further be employed for CW Doppler, where a transmit element continuously transmits while another element continuously receives. A continuous transmit and receive operation helps the imaging technique not suffer from aliasing issues that accompany sampled Doppler methods, such as PW or color Doppler. Aliasing limits the maximum velocity of flow that can be reliably measured, to half of the pulse repetition frequency. Different regions of the transducer are typically used for continuous transmit and continuous receive so that the elements are widely separated, minimizing cross talk.

In some examples, the sub-elements (1996-1) and (1996-2) as shown in FIG. 19D may have different center frequencies and when operated together as a single composite element, exhibit wider bandwidth. The sub-elements (1996-1) and (1996-2) still operate as a two-terminal device when the top terminal and bottom terminals of sub-elements (1996-1) and (1996-2) are connected together. This wide bandwidth performance can also be achieved using the structure shown in FIG. 19C. Sensitivity in this structure can be further increased using dual polarization techniques.

FIG. 19E illustrates a representative example of an imaging device where one sub-element (2997-1) is configured to be continuously in transmit mode and another sub-element (2997-2) is configured to be continuously in receive mode. The imaging device includes a first top electrode (1982-1) and second top electrode (1982-2), first bottom electrode (1978-1) and second bottom electrode (1978-2); piezoelectric layer (1980-1) disposed between top electrode (1982-1) and bottom electrode (1978-1); piezoelectric layer (1980-2) disposed between top electrode (1982-2) and bottom electrode (1978-2); and two conductors (1984-1) and (1984-2) that are electrically coupled to respective top and bottom electrodes (1982-1),(1978-1) and (1982-2),(1978-2). Hereinafter, the terms top and bottom merely refer to two opposite sides of the piezoelectric layer.

A trench (1998) is provided between the membrane (1374-1) of sub-element (2997-1) and membrane (1374-2) of sub-element (2997-2) to minimize cross talk between sub-elements (2997-1) and (2997-2). In one example, CW Doppler imaging can be performed using one of the sub-elements (2997-1) for transmit and another of the sub-elements (2997-2) for receive. This allows efficient utilization of the aperture size (FIG. 21, 3412), where transmitting and receiving elements can be adjacent. When CW Doppler imaging is performed by programming an element to be in transmit mode of operation continuously while another element in a different portion of the imager is programmed to be continuously in receive mode, cross talk from the two elements are relatively small compared to other types of noise, since they are spatially separated by relatively large distances in relation to the dimensions of the transducer. For PW operations, the same sub-element can be used for transmit and then switched to receive mode.

Figure 19F:
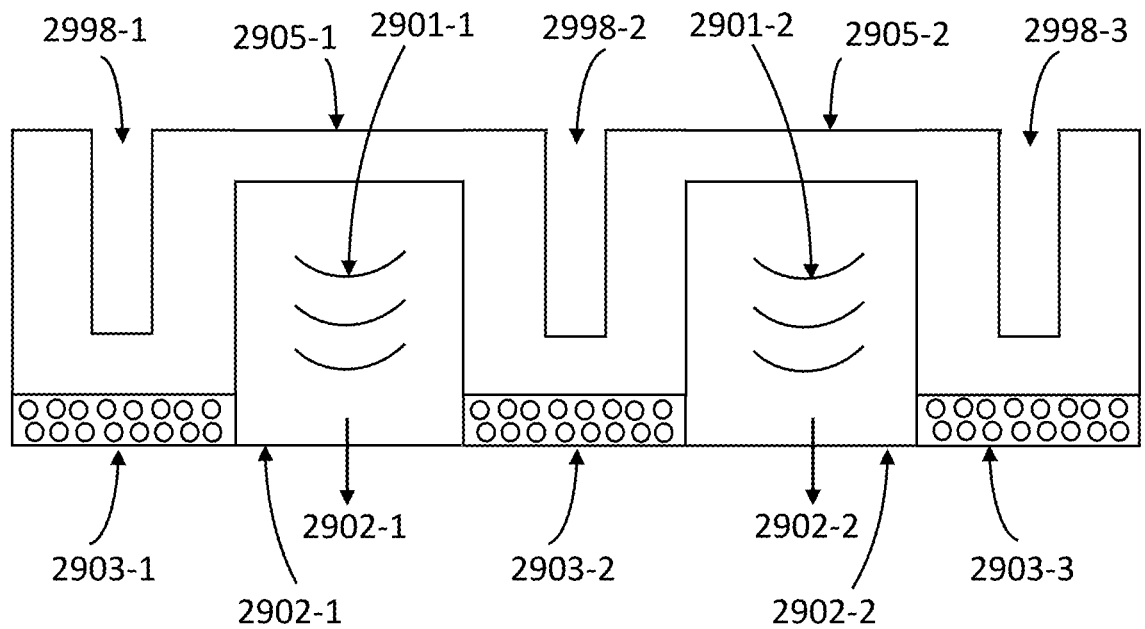
FIG. 19F illustrates a cross-sectional view of two adjacent elements, showing isolation details to minimize cross talk, according to an example of the principles described herein.

FIG. 19F shows an example of reducing cross talk between neighboring elements. In this example, membranes 2905-1, -2 are electrically simulated by electrodes (FIG. 19E, 1982-1, -2 and 1978-1, -2), which causes an ultrasonic waveform to be transmitted in the direction of area 2902-1 and 2902-2. Wavefronts 2901-1, -2 traveling sideways are reflected and attenuated by trenches 2998-1, -2, -3. Areas 2903-1, -2, -3 represent materials intended to match impedance of transducers to tissue. Areas 2903-1, -2, -3 have a different impedance than areas 2902-1, -2. Therefore, wavefronts 2901-1, -2 traveling sideways are reflected by the mismatch and become attenuated, which reduces cross talk. Materials may be mismatched, for example, by applying an acoustic lensing layer over the bottom surface of one or more areas 2903-1, -2, -3 and 2902-1, -2. In some embodiments, materials in one or more areas 2903-1, -2, -3 and areas 2902-1, -2 are kept the same.

Figure 19G:
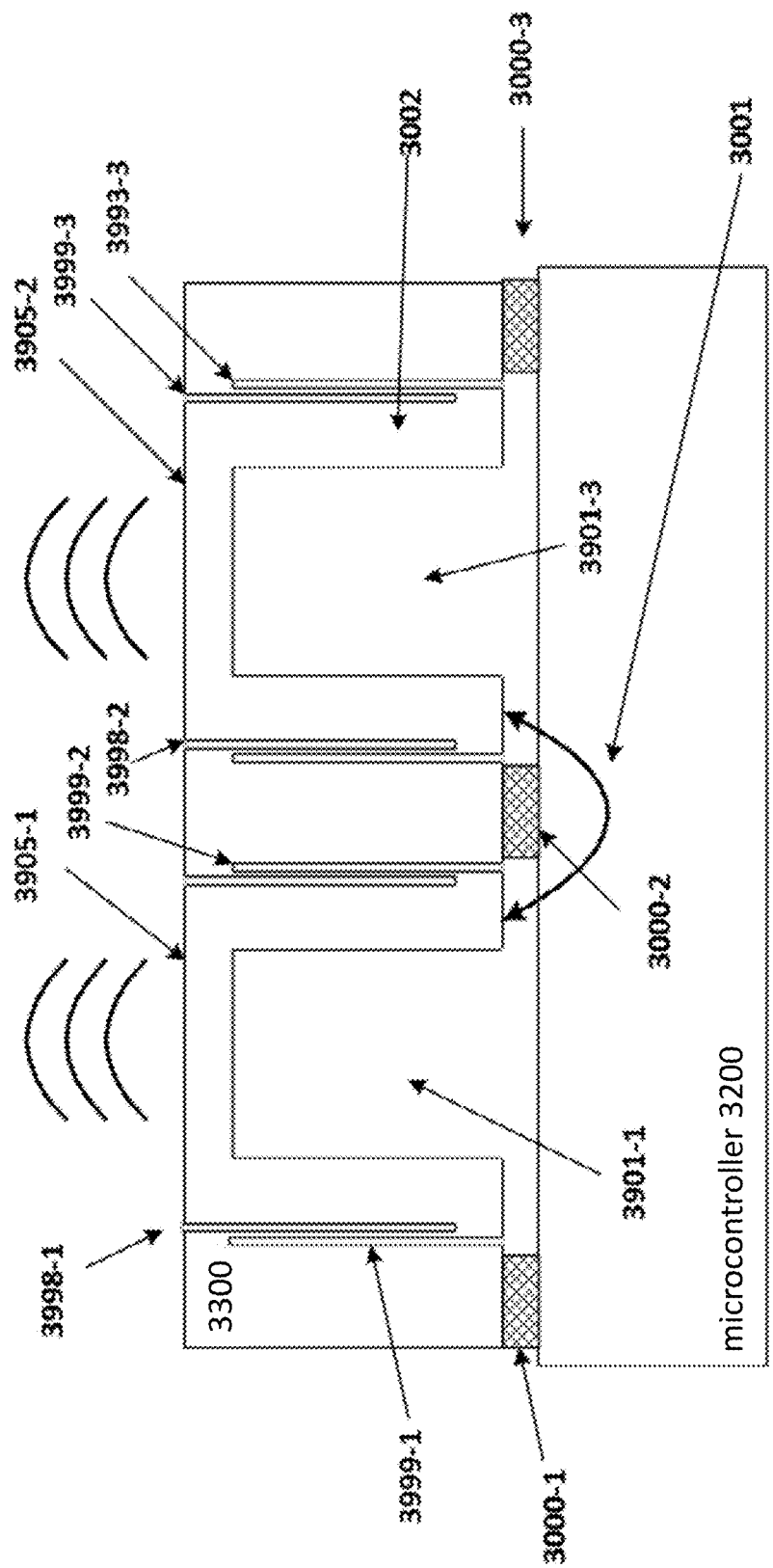
FIG. 19G illustrates a cross-sectional view of two adjacent elements, with isolation details to minimize cross talk, according to an example of the principles described herein.

FIG. 19G shows an example of reducing cross talk between neighboring elements. In this example, multiple trenches 3998-1, -2, -3, and 3999-1, -2, -3 are utilized to isolate coupling between adjacent elements or sub-elements and thereby provide crosstalk isolation. Trenches 3998-1, -2, -3 start from opposite sides of trenches 3999-1, -2, -3 on the substrate 3002. A first trench (3998-1) starts from a top surface, while a second trench (3999-1) starts from a bottom surface. Similarly, other trenches (3998-2, 3999-3) start from the top surfaces and still more trenches (3999-2,3993-3) start from the bottom surface. Connections (3000-1, 3000-2, 3000-3) establish an electrical connection between a controller (3200) such as an ASIC and the structure (3300) containing the vibrating membrane, which structure may be a micro-electro-mechanical system (MEMS) structure. The double trench arrangement isolates any vibration energy transmitted from the controller (3200) via the connections (3000-1, 3000-2, 3000-3) and then transferred to an adjacent element, as shown by (3001), indicating reduced vibration coupling for elements with cavities (3901-1, 3901-3). In general, two trenches provide improved isolation, compared to one trench. Such a topology may be referred to as front firing, where the cavities (3901-1, 3901-3) are facing the ASIC controller (3200). In some examples a connection (3000-2) supports membrane (3905-2). Note that the diagram is not drawn to scale and is intended to illustrate the principle of operation.

In one example, an ASIC is attached to the substrate and connected electrically to enable anatomy and doppler flow imaging, where each piezoelectric element exhibits a plurality of modes of vibration. Imaging may be performed by the transducer at low frequencies such as for abdominal or cardiac imaging or at higher frequencies for musculoskeletal (MSK) or vascular imaging.

In one example, the membrane is connected to the ASIC in a back firing orientation in which the cavity faces the imaging target. In another example, the membrane is connected to the ASIC in a front firing orientation, where the cavity faces the ASIC and the membrane emits and receives from the front face.

In another example, the imaging device includes MEMS-based elements that have wide bandwidth. The imaging performed by the transducer may be for low frequency imaging, such abdominal or cardiac imaging, or high frequency imaging, such as musculoskeletal (MSK) or vascular imaging.

In another example, the imaging device further includes MEMS-based elements that have wide bandwidth. The imaging may be performed by the transducer for low frequency imaging for abdominal or cardiac imaging or high frequency imaging (MSK) or vascular imaging.

Figure 19H:
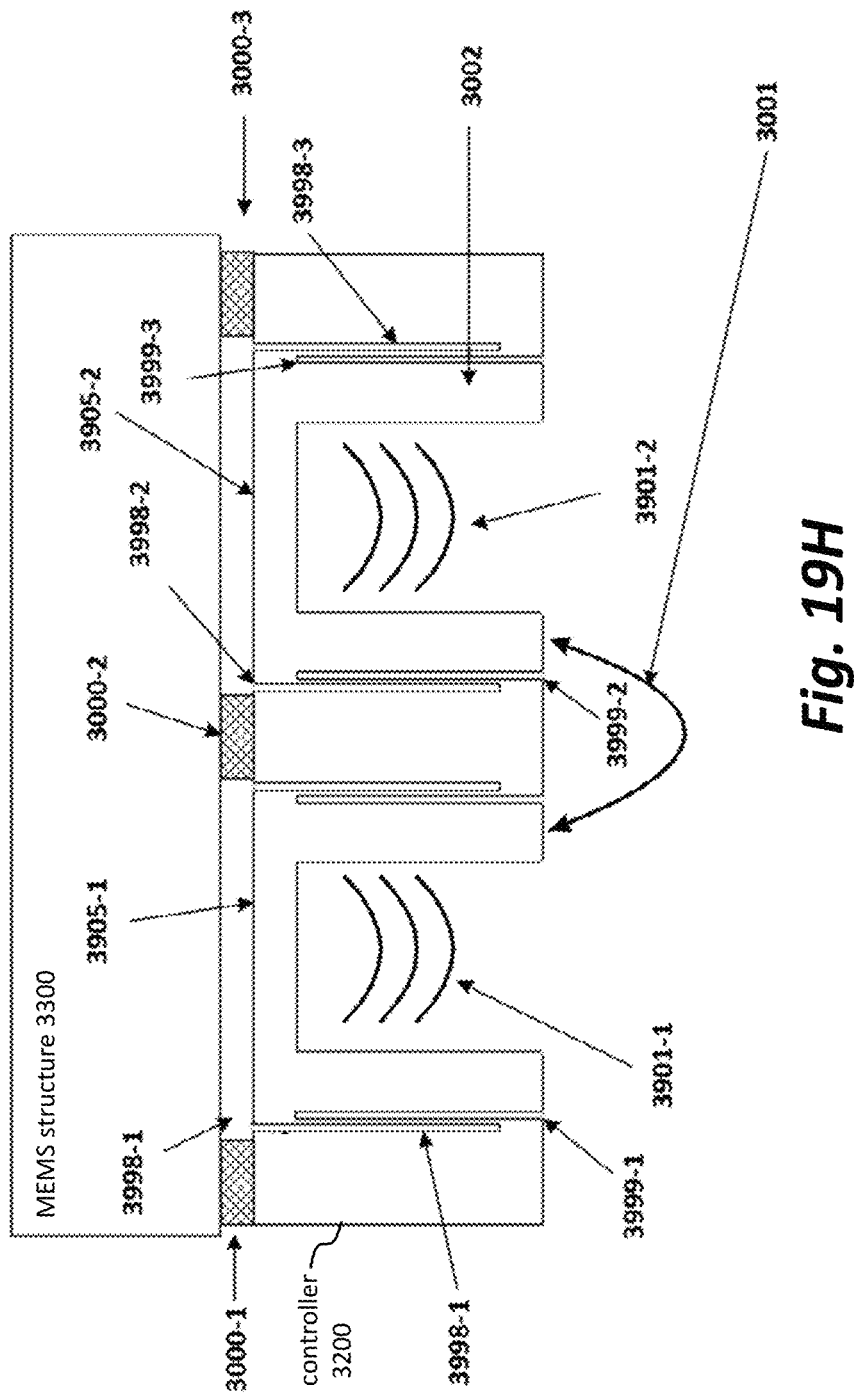
FIG. 19H illustrates a cross-sectional view of two adjacent elements, with isolation details to minimize cross talk, according to an example of the principles described herein.

FIG. 19H shows an example of reducing cross talk between neighboring elements. Compared to FIG. 19G, the orientation of the vibrating membrane is flipped. The orientation of FIG. 19G is referred to as front firing, whereas the orientation of FIG. 19H is referred to as backfiring. In this example, the cavities (3901-1, 3901-2) faces away from the ASIC controller (3200) and instead face the target to be imaged. In this example, the connections (3000-1, 3000-2, and 3000-3) that connect to the ASIC controller (3200) can be made without using TSV (through silicon via) because metallization and connection on the MEMS structure (3300) are within a few micrometers away from each other and metal vias and other connections that do not require TSVs. TSVs are difficult to manufacture and introduce increased cost and complexities in the manufacturing process. In the backfiring topology depicted in FIG. 19H, the trenches (3999-1, 3999-2, and 3999-3) start from the bottom surface of the MEMS structure 93300), while other trenches (3998-1, 3998-2, and 3998-3) start from the top surface to the connections (3000-1, 3000-2, and 3000-3). As described above, the use of two trenches (3998-2 and 3999-2) and similar structures on the other side of the connection (3000-2) helps provide additional isolation between the membranes (3905-1 and 3905-2) as indicated by coupling (3001). The coupling (3001) is shown from the side facing the target to be imaged. However, coupling from the ASIC controller (3200) side as shown in FIG. 19G also applies for FIG. 19H, since the double trenches help isolate coupling between adjacent membranes from the front face or the back face of the MEMS structure (3300).

Although two trenches (3998-2 and 3999-2) are shown, a single trench may be used. For example, a trench associated with the top surface, such as trench (3998-2) may be used alone or a trench associated with the bottom surface like trench (3999-2). A single trench either from the top or from the bottom may also be sufficient to provide isolation for other applications described herein.

Figure 19I:
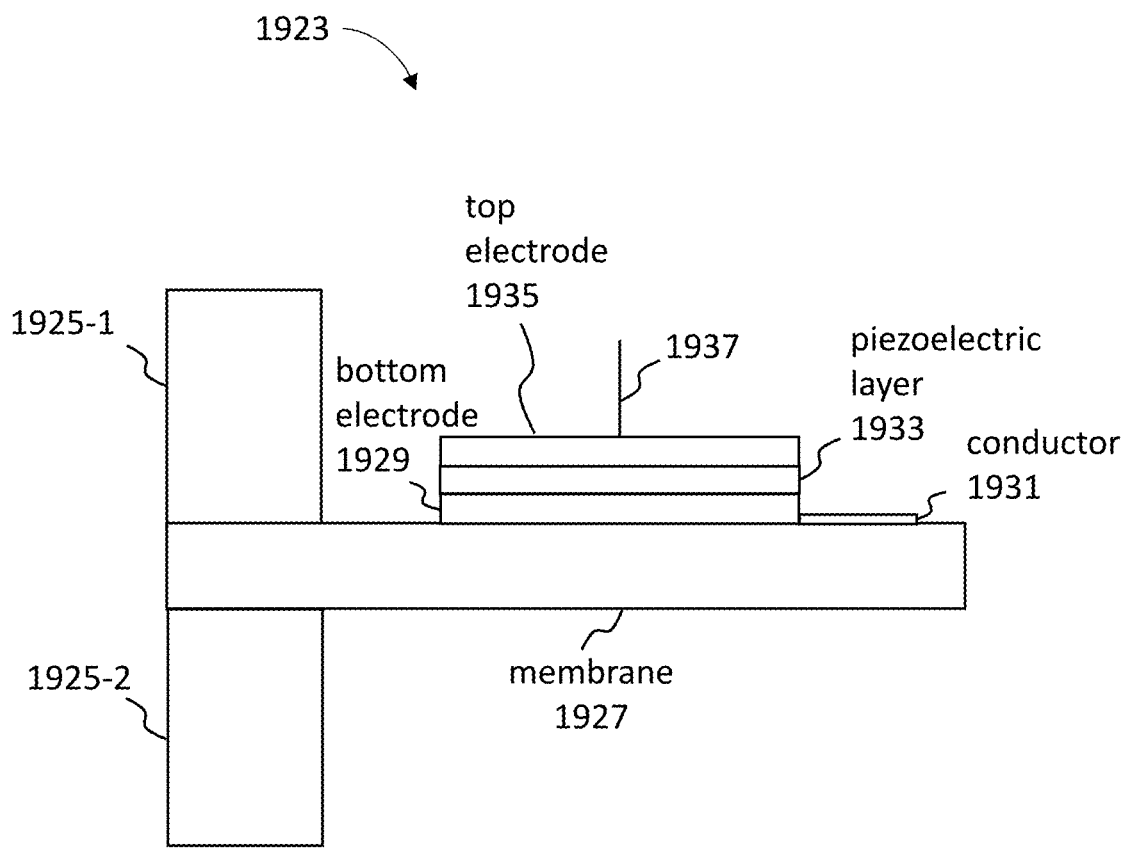
FIG. 19I illustrates a piezoelectric element using flexural mode of operation, according to an example of the principles described herein.

FIG. 19I illustrates a cross-sectional view of a piezoelectric element (1923) according to an example of the principles described herein. As depicted, the piezoelectric element (1923) may utilize a transverse mode of operation and include substrates (1925-1, -2), a membrane (1927) secured to the substrate at one end, a bottom electrode (1929) that is electrically coupled to a conductor (1931), a piezoelectric layer (1933), and a top electrode (1935) that is electrically coupled to a conductor (1937). The membrane (1927) may be secured to the substrates (1925-1, -2) at one end so as to vibrate in the transverse mode. The membrane (1927) can be supported on both sides with the substrates (1925-1, -2). It is to be noted that all previous examples of piezo elements can be operated in the transverse mode of operation and all sides of the membrane (1927) can be supported on the substrate. Transverse mode of operation and its principles apply to all examples discussed herein.

It is noted that the piezoelectric element (1923) may have any suitable number of top electrodes. Also, it is noted that more than one piezoelectric element may be installed on the membrane (1927). It is further noted that the substrates (1925-1, -2) and membrane (1927) may be formed of one monolithic body and the membrane (1927) may be formed by etching the substrates (1925-1, -2).

Figure 20A:
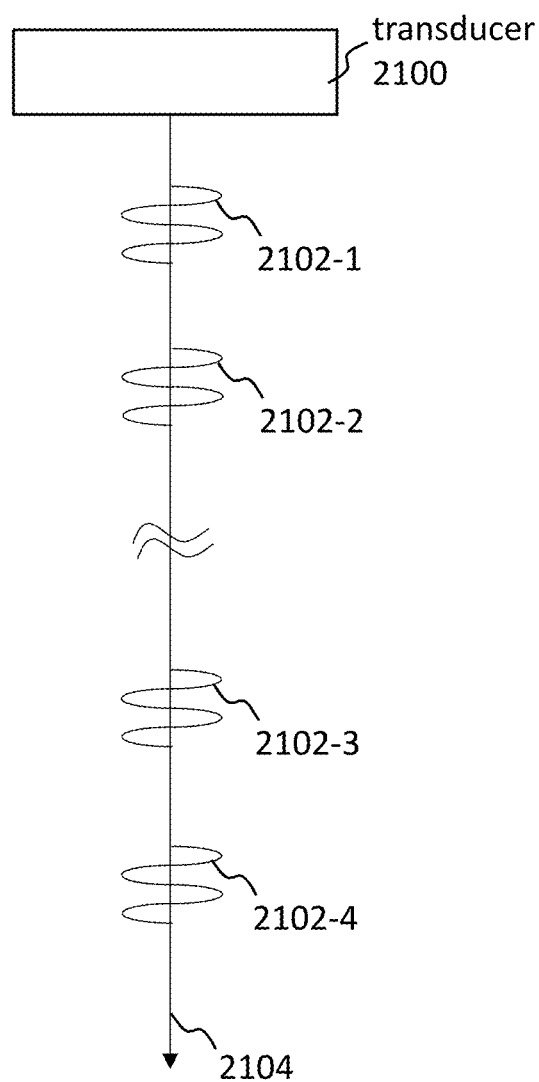
FIG. 20A illustrates a scan line showing an ensemble of pulses, according to an example of the principles described herein.

Color Doppler flow mapping uses multi-gated sampling of many scan lines using bursts of several cycles of waveforms at a carrier frequency that the transducer is responsive to. FIG. 20A illustrates several pulses 2102-1, 2102-2, 2102-3, and 2102-4 that make up an ensemble. Each pulse consists of at least one or multiple cycles at a carrier frequency typically between 2-10 MHz.

Figure 20B:
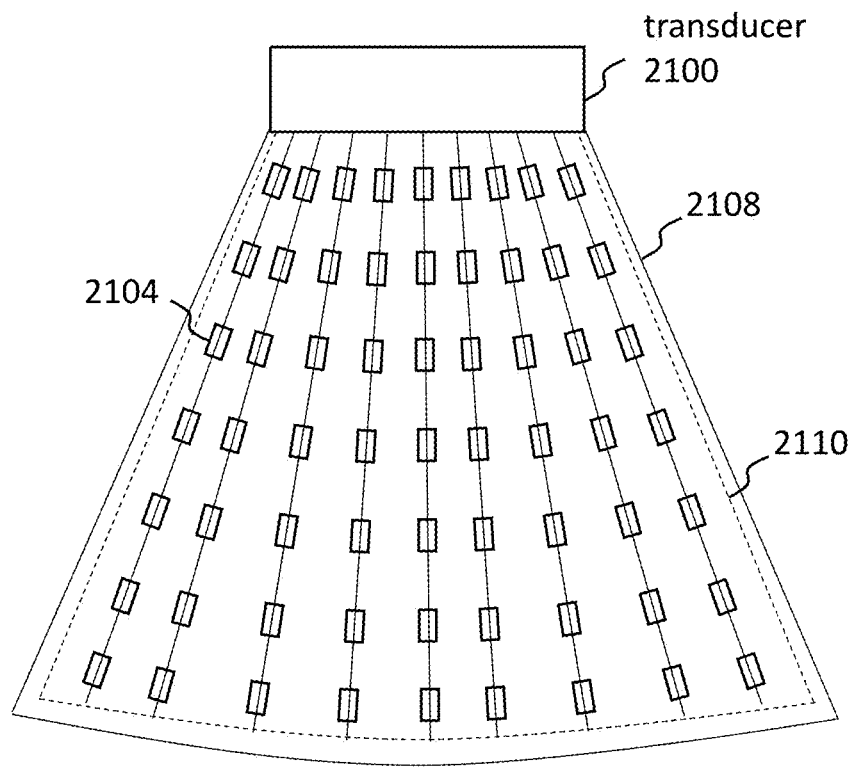
FIG. 20B illustrates an imaging frame with multiple scan lines with each line showing multiple samples, according to an example of the principles described herein.

FIG. 20B shows a color window (2110) inside a frame (2108) of a transducer 2100. Several scan lines (2104) are shown, each with multi-gated pulses. Consecutive sampling of the signals along the scan line (2104) is timed according to the depth of the sampling location. Each returning echo is referenced to its range gate, which identifies it with the spatial location of its origin and is electronically processed with suitable delays. After all the echoes from the first pulse are received, a second pulse is launched in phase with the $1^{st}$ pulse on a same scan line (2104). Appropriate timing of the pulse repetition frequency is important in that a pulse must return before another pulse goes out, otherwise range ambiguity is created. Once sampling of a scan line is completed, the next scan line is done in the same manner and a color flow map is completed by multiple scan lines sweeping across the color window used.

To determine a mean Doppler shift, each echo from each pulse from a particular range gate is compared to its previously sampled pulse from the same range gate. An auto correlation technique is used to obtain the mean Doppler phase shift. Auto correlation is achieved delaying echo samples appropriately with respect to previous similar echoes from the same line, multiplying and integrating results. Auto correlators measure phase difference from two consecutive echoes. Static portions of the target (i.e., not flow related) do not show phase differences, but phase from items that are moving, like blood, will show a difference.

Doppler imaging is sensitive to noise. Gain control can be used for signal amplification. Separate controls can be designed for pulse echo imaging and for color Doppler function. Larger gains in color Doppler make the imaging more sensitive. However, an increase in gain also increases noise from physical components in the imager. A key component of this noise comes from the LNA of the receiver and so it may be desirable to achieve a very low noise floor for these LNAs. Because low noise floor causes high power consumption and thermal heating in the transducer, LNAs in the imager may be designed to be active only in a color flow window activated, with other LNAs in the imagers placed in a low power state. Further, the active LNAs may be electronically adjustable to optimize according to power vs noise level performance needed.

A high pass filter may be used to eliminate high amplitude low frequency Doppler shift signals generated by movements of vascular walls, moving tissue, and heart movements. These signals have high power content that can corrupt lower level signals from, for example, blood flow. A high pass filter blocks low frequency information from these spurious moving structures. However, it can also block low velocity blood flow signals present in certain target types but not in others. Therefore, any hardware-based filter also needs to be programmable with respect to cutoff frequency. This minimum level of filtering is then augmented with wall filters that are implemented in software. The wall filters have adjustable levels of thresholds in the high pass function and sophisticated ability to discriminate between low velocity blood flow and wall motion. They are also responsive to different applications, frequency used, and pulse repetition rates. In an exemplary embodiment, a programmable high pass function is built in to the imaging head around the LNA. This allows a high pass filter functionality with remaining high pass functions to be implemented in a wall filter later in the signal chain.

Doppler shifts are sensitive to the angle of insonation of the flow axis and the ultra sound beam (see equations above). The signal can also completely disappear if the angle is zero (see equations above). The angle can be improved by moving the probe physically when possible. However, in an exemplary embodiment, the scan lines can be also be electronically steered in 2D or 3D, when a 2D matrix of elements are used, with each element having independent control on Tx and Rx functions, including time delay. Thus, the desired angle can be electronically achieved by steering the beam to the desired location. In such an arrangement, each element can be selected electronically independent of neighboring, or adjacent elements and independently placed in Tx or Rx modes and appropriate timing delays can be applied to elements whether in Tx or Rx mode.

As noted, Doppler imaging is sensitive to noise and signal-to-noise ratio. It is therefore desirable to increase the signal in instances described herein. Traditionally, 2D imagers used a mechanical lens with a curvature in the elevation direction to focus energy in the elevation plane. This resulted in pressure in the elevation focal point and enhanced sensitivity. However, such a configuration results in a fixed focal length that cannot be adjusted. In an example of the present disclosure, electronic focusing is implemented for 2D imaging using a 2D array of elements. Additionally, a mechanical lens is retained. The electronic capability using a 2D array allows electronic changes in the focal point and also allows focusing in three-dimensional space. The steering capability depicted above in FIG. 6C allows the beam to be steered to further improve Doppler sensitivity as noted earlier. Electronic focus in the elevation plane can also be implemented by applying different relative delays for elements on a column. For example, in FIG. 5, elements 104 are arranged in rows and columns, where reference number 542 indicates a column. Delays in the transmit drive signal to each of these elements relative to each other creates focus patterns or beam steering as shown in FIG. 6C.

Furthermore, transducer elements may be on a curved plane as shown in FIG. 4. This curvature may be intentionally created or may be inadvertently created due to stresses in the board on which the transducer and ASIC are mounted or due to stresses in the transducer integration with the ASIC. This can vary from unit to unit. A predetermined focal point that is same for all devices would create errors in actual focal point achieved due to the curvature. However, it is possible to measure the curvature of each unit on a production line. This information is then used to apply relative delays to the elements that compensate for these delays. An external controller sends the desired delay information to the ASIC. The ASIC applies the compensated delay to each element and restores high signal pressure output that was degraded by uncompensated curvature in the transducer elements.

In one example, the transducer may be a wide bandwidth multimodal device, where the membranes can vibrate at a number of different frequencies simultaneously spread over a wide band, thus creating a wide bandwidth transducer. This operation is valid in both the transmit mode and the receive mode. This allows B-mode anatomy as well as flow based on Doppler imaging to be possible over a wide bandwidth, and allows many applications (typically requiring separate imagers that cover a limited bandwidth range) using the same imager.

While a piezoelectric element can exhibit multiple modes of vibration, in some examples, just one mode of vibration is triggered when input stimulus is bandlimited to be less than frequencies of adjacent modes. Further, frequencies generated from a first mode of vibration can be designed to overlap those from the second mode of vibration. Still further, in some examples, multiple modes of vibration occur simultaneously when driven by a wide band frequency input that includes center frequencies.

In summary, an imaging device is described utilizing an array of PMUT-based transducers connected to control electronics on a per element basis and housed in a portable housing. The imaging device allows system configurability and adaptability in real time to actively control power consumption, temperature and acoustic power in the imaging device. Beam steering in 3D space is also achieved. Elements can be programmed to be in receive or transmit mode. Electronics to enable B-mode anatomy imaging and Doppler mode flow imaging are enabled over a large bandwidth, typically relying on multiple transducers using conventional bulk piezo imaging.

Another exemplary imaging device includes at least one piezoelectric transducer. A transducer imaging device includes at least one piezoelectric element. A two-dimensional (2D) array of piezoelectric elements is arranged in rows and columns on the piezoelectric transducer. Each piezoelectric element includes at least two terminals. Each piezoelectric element may be physically isolated from each adjacent piezoelectric element to reduce cross talk. A first column of the piezoelectric elements includes each respective piezoelectric element having a first top electrode programmed to be connected to a respective receive amplifier. A second column of the piezoelectric elements includes each respective piezoelectric element programmed to be connected to a respective transmit driver. Each of the respective piezoelectric elements in the first column can be electronically programmed to be as if connected together to form a column. Each of the respective piezoelectric elements in the second set can be electronically programmed to be as if connected together to form a column. Furthermore, any number of adjacent columns may be programmed to operate in receive mode while a different number of columns located elsewhere maybe programmed to be in transmit mode. In some examples, multiple modes of vibration may be exhibited in each piezoelectric element. A single receive amplifier may be used, where at least one piezoelectric element in the first column is connected to the receive amplifier. Also, a single transmit driver may be present where at least one of the piezoelectric elements in the second column is connected to the transmit driver. The electronically programmed connections of the piezoelectric elements may enable connection of an arbitrary number of piezoelectric elements in a column.

In some examples, at least one sub-aperture may include at least one column of piezoelectric elements and each piezoelectric element may include two sub-elements. Each sub-element may be selected to operate with a programmable transmit and receive function such that a first sub-element can simultaneously transmit while a second sub-element is receiving, and each sub-element can switch between a transmit mode and a receive mode. At least one piezoelectric element may comprise two sub-elements and two terminals, each sub-element having a different center frequency and bandwidth such that when they are used in parallel, the piezoelectric element exhibits a wider bandwidth than any one sub-element by itself. In one example, at least one piezoelectric element is used for B-mode and Doppler flow measurements. In an example, each piezoelectric element comprises two sub-elements used for CW Doppler imaging, and at least a first piezoelectric element is placed in transmit mode while a second piezoelectric element is simultaneously placed in receive mode.

Connections of the piezoelectric elements in at least one of the columns and rows are electronically programmable to enable connection of an arbitrary number of piezoelectric elements in the column and row.

A first piezoelectric element of an array may be continuously in transmit mode while a second piezoelectric element of the array is continuously in receive mode to enable continuous wave (CW) Doppler imaging. A set of columns can transmit continuously while a set of columns can be programmed to be in receive mode which also enables CW Doppler imaging. Regions may be separate to minimize cross talk between the transmit and receive portions of the transducer array. The height of the columns, and specifically, the number of piezoelectric elements that make up a column, is electronically adjusted to adjust acoustic power output, among other things. Thus, acoustic output power is adjusted by electronically adjusting the number of elements participating in the transmission. The power supply can be identical for Doppler based flow imaging and anatomy imaging. However, Doppler imaging involves many more pulses than say B-mode imaging. Therefore, more acoustic power output is developed during flow imaging under similar conditions compared to B-mode, that may exceed regulatory limits. By electronically adjusting the number of elements that contribute to acoustic power, the acoustic power output for flow imaging can be optimized. Additionally, the pulse amplitude developed at each element can be electronically selected, while using same power supplies for all imaging modes. This allows acoustic power adjustment as needed as well as a low cost, low size power management circuit to power circuits for flow and anatomy imaging. This is helpful for low cost portable imagers. In an example, a same number of power supplies are used for Doppler modes and B-mode by electronically adjusting acoustic power transmitted from at least a portion of the array of piezoelectric elements. In an example, power from each piezoelectric element is adjusted by using appropriate levels of a multilevel transmit pulsar output. In an example, the B-modes and Doppler modes maintain a specific power level, such as an acoustic power level, and a specific mechanical index while using same power supplies for imaging modes.

In each of the examples, each piezoelectric element is used as if it were connected to a transmit and receive channel to perform actions described in the specification. The channels may be in a constant state where they remain as a transmitting, receiving, or both transmitting and receiving channel. Alternatively, there may be a changing state where the channels change between one of the types of states of transmitting, receiving, and both transmitting and receiving.

In addition, each piezoelectric element within the separate independent array may exhibit one or more modes of vibration. In an example, a membrane supports multiple modes of vibration, enabling a larger bandwidth for the imaging device. An example includes that at least one piezoelectric element comprises two sub-elements and two terminals. Each sub-element has a different center frequency and bandwidth such that when used in parallel exhibits a wider bandwidth than any one sub-element by itself. Anatomy and Doppler imaging is performed over a large bandwidth with electronic steering and focus control of the elevation plane to improve sensitivity.

An example further includes that each piezoelectric element exhibits multiple modes of vibration, thus enabling Anatomy and Doppler imaging over a large bandwidth with electronic steering and focus control of elevation plane. imaging may be performed by the transducer for low frequency imaging for abdominal or cardiac imaging. Also, imaging may be performed by the transducer for high frequency imaging for musculoskeletal (MSK) or vascular imaging.

As described earlier, transducers may have a large imaging surface, or aperture, and it may be desirable to operate on the entire aperture. An entire aperture relies on the entire array of elements or sub-elements. Under electronic control, the aperture size can be changed to include a smaller number of elements or sub-elements, and possibly down to a single sub-element. A smaller aperture is a smaller imaging surface, or subaperture, and includes a subset of piezoelectric elements in the piezoelectric layer.

Figure 21:
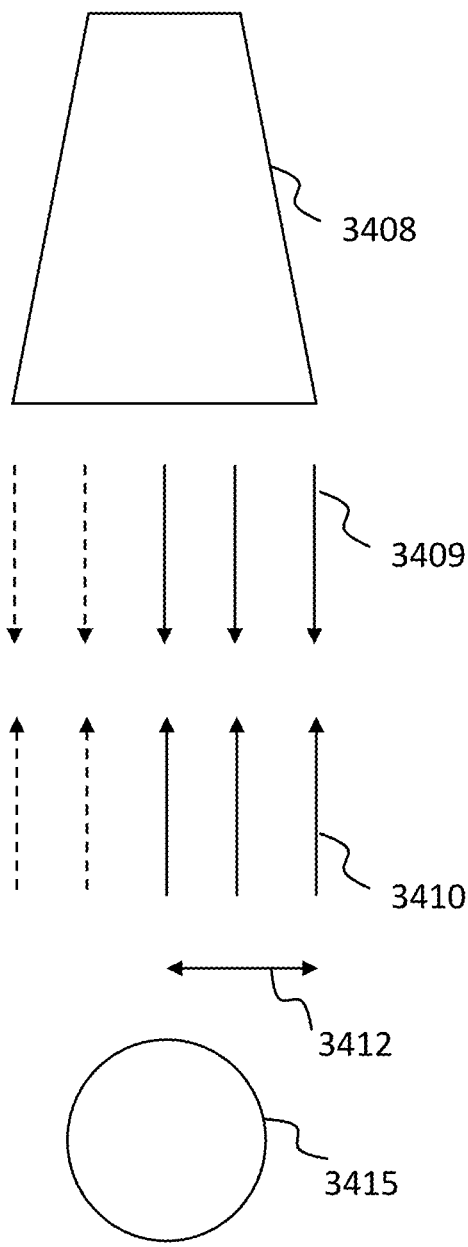
FIG. 21 illustrates a transmit and receive operation using sub-elements and subsets to obtain an image, according to an example of the principles described herein.

Turning to FIG. 21, an imaging device (3408) is shown with a transmit operation (3409) and a receive operation (3410) as indicated by arrows. The solid arrows in the transmit operation (3409) and receive operation (3410) indicate sub-elements and subsets of piezoelectric elements (FIG. 1, 104) being used in the operations in the area of the arrows. The dotted arrows indicate which sub-elements and subsets of piezoelectric elements (FIG. 1, 104) are not being used. The aperture size (3412) indicates the portion of the imaging object (3415) that will be imaged as a result of the sub-elements and subsets being used. The selection and configuration of sub-elements and subsets may be altered electronically to define the aperture size (3412).

Note that certain sub-elements may be used for one operation (e.g., transmit, receive) while other sub-elements may be used for another operation (e.g., transmit, receive). There may be some overlap in the sub-elements used for each operation. The sub-elements may be the same for each operation. The sub-elements may further have simultaneous transmit and receive capability.

Two sub-elements can also be used to further broaden bandwidth, where center frequency of the sub-elements are different and when used together simultaneously, broaden bandwidth when used in transmit or receive operations. The imaging device may be implemented with multiple sub-elements such that a bandwidth of the multiple sub-elements combined is larger than each sub-element.

Various types of imaging can be performed using the array of piezoelectric elements (FIG. 1, 104). For example, A scan, B scan, C scan, and Doppler mode may be performed. Further types of imaging that can be performed include pulsed Doppler and color Doppler. Additionally, Doppler processing can be performed in which some clutter rejection filtering, such as programmable high pass filtering, occurs prior to digitizing, thus increasing a dynamic range of the Doppler signals with high levels of clutter. In an example, Doppler processing is performed on a Doppler signal received from at least one piezoelectric element and a low noise amplifier performs programmable high pass filtering on the received Doppler signal prior to digitization, and pay perform further digital signal processing, and beam forming.

Figure 22:
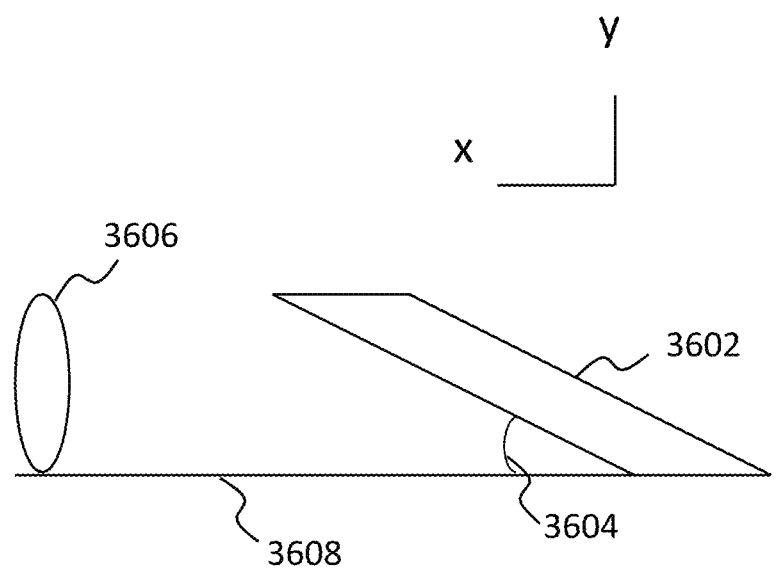
FIG. 22 illustrates an elevation plane being tilted and focused, according to an example of the principles described herein.

In some examples, an elevation plane may be tilted and focused electronically to get closer to an optimal Doppler angle for better signal visualization. FIG. 22 depicts an elevation angle (3604) defined by elevation plane (3602) between a horizontal plane (3608) and a line of sight measured in a vertical plane. The imaging object (3606) can have better visualization depending on the elevation angle (3604) that may be modified to obtain a desired visualization.

High quality Doppler imaging may have a high signal to noise ratio (SNR). The SNR is a function of the elevation angle (3604) shown in FIG. 22. In an example, the elevation angle (3604) can be electronically adjusted for flow imaging. The elevation focus can be steered in the elevation plane (3602) by adjusting delays on elements on a column. Note that focusing beams in the axial direction is controlled by adjusting delays on elements in the azimuth direction. With independent delay control in elevation and azimuth, 3D beam steering is possible to improving Doppler signal amplitude. In an example, a steering structure is used for beam steering capability in 3D space. In another example, a steering structure is used for beam steering in 3D space electronically to get closer to an optimal Doppler angle for better signal visualization. In another example, an azimuth focus, elevation focus, and an aperture size of the imaging device are to be altered electronically.

Figure 23:
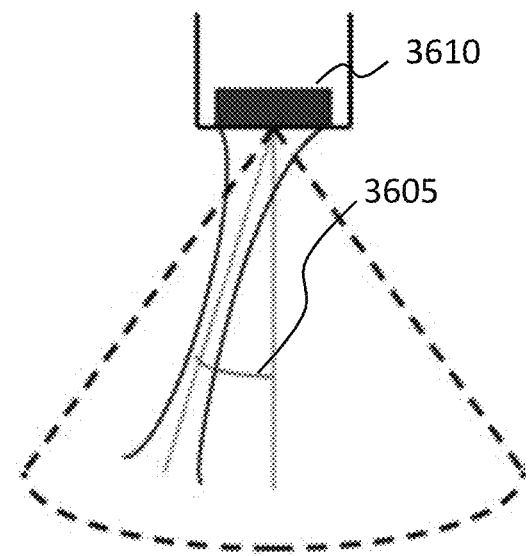
FIG. 23 illustrates an azimuth focus being altered electronically, according to an example of the principles described herein.

As shown in FIG. 23, the azimuth angle (3605) of an imaging device (3610) may vary to produce a circular sector field of view that spans as much as 90 degrees in an azimuth angle. This may be accomplished simultaneously or independently of the aperture size (FIG. 21, 3412) being altered. It is therefore possible to steer a transmit beam in 3D space and anatomy and flow imaging can be carried out in 3D space.

Elements and sub-elements of columns may be treated as separate, independent columns. Elements and sub-elements of rows may be treated as separate, independent rows. In some variations, columns and rows, or portions thereof, switch roles so that they are treated as rows and columns, respectively.

Further configurations may include that the respective receive amplifiers or single receive amplifier be enabled in a receive mode and disabled in a transmit mode, used for example, in B-mode anatomy imaging, Color Doppler, or PW flow imaging. Similarly, configurations include that the respective transmit drivers or single transmit driver be enabled in a transmit mode and disabled in a receive mode for the imaging modes mentioned for receive amplifiers. An example includes that each piezoelectric element is first placed into transmit mode and subsequently placed into receive mode to receive echoes from the transmit mode, wherein transmit power level, an azimuth focus, elevation focus, beam steering in 2D or 3D space, and an aperture size of the imaging device are altered electronically.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

For purposes of explanation, specific details set forth herein are to provide an understanding of the disclosure. It will be apparent, however, to one skilled in the art that the disclosure can be practiced without these details. Furthermore, one skilled in the art will recognize that examples of the present disclosure may be implemented in a variety of ways, such as a process, an apparatus, a system, a device, or a method on a tangible computer-readable medium.

One skilled in the art shall recognize: (1) that certain fabrication steps may optionally be performed; (2) that steps may not be limited to the specific order set forth herein; and (3) that certain steps may be performed in different orders, including being done contemporaneously.

Elements/components shown in diagrams are illustrative of exemplary embodiments of the disclosure and are meant to avoid obscuring the disclosure. Reference in the specification to "one example," "preferred example," "an example," or "examples" means that a particular feature, structure, characteristic, or function described in connection with the example is included in at least one example of the disclosure and may be in more than one example. The appearances of the phrases "in one example," "in an example," or "in examples" in various places in the specification are not necessarily all referring to the same example or examples. The terms "include," "including," "comprise," and "comprising" are understood to be open terms and any lists are examples and not meant to be limited to the listed items. Any headings used herein are for organizational purposes only and shall not be used to limit the scope of the description or the claims. Furthermore, the use of certain terms in various places in the specification is for illustration and should not be construed as limiting.

The invention claimed is:

1. An imaging device, comprising:
a transducer comprising a 2D array of piezoelectric elements arranged in rows and columns on a substrate of the transducer, each piezoelectric element having at least two terminals, each piezoelectric element having a first top electrode connected to a respective receive amplifier or a transmit driver under programmed control,
the 2D array formed by at least a first column and a second column, the piezoelectric elements being configured to (i) transmit and then subsequently receive or (ii) simultaneously transmit and receive,
wherein connections of the piezoelectric elements in the rows are electronically programmable to enable connection of an arbitrary number of piezoelectric elements in each row,
wherein adjacent piezoelectric elements in the 2D array are isolated from each other by at least two trenches extending into the substrate in a space between the adjacent piezoelectric elements.

2. The imaging device of claim 1, wherein elements and sub-elements of rows are controlled as separate, independent rows.

3. The imaging device of claim 1, wherein at least one piezoelectric element comprises two sub-elements and two terminals, each sub-element having a different center frequency and bandwidth such that when used in parallel exhibits a wider bandwidth than any one sub-element by itself.

4. The imaging device of claim 1, wherein each piezoelectric element comprises two sub-elements used for CW Doppler imaging, and wherein at least a first piezoelectric element of the array is placed in transmit mode while a second piezoelectric element of the array is simultaneously placed in receive mode.

5. The imaging device of claim 1, wherein for pulsed wave (PW) Doppler imaging, at least the first piezoelectric element is placed in transmit mode and switched to receive mode.

6. The imaging device of claim 1, wherein each piezoelectric element is first placed into transmit mode and subsequently placed into receive mode to receive echoes from the transmit mode, wherein transmit power level, an azimuth focus, elevation focus, beam steering in 2D or 3D space, and an aperture size of the imaging device are altered electronically.

7. The imaging device of claim 1, wherein a desired azimuth focal depth is adjusted for curvature in the transducer.

8. The imaging device of claim 1, wherein an elevation focus is adjusted electronically to include delay adjustments to compensate for curvature in the transducer.

9. The device of claim 1, wherein the at least two trenches comprise two trenches that extend into the substrate from a first side of the substrate.

10. The device of claim 1, wherein the at least two trenches comprise two trenches that extend into the substrate respectively from first and second sides of the substrate.

11. The device of claim 1, wherein the at least two trenches comprise at least three trenches, wherein at least a first trench extends into the substrate from a first side of the substrate, and wherein at least a second trench extends into the substrate from a second side of the substrate.

12. The device of claim 1, wherein the at least two trenches extend in a non-intersecting pattern within the 2D array.

13. An imaging device comprising an array of piezoelectric elements arranged in rows and columns on a substrate, the piezoelectric elements being configured to perform transmit and receive operations, the substrate comprising an arrangement of trenches that extends between the rows and columns of the piezoelectric elements in the array for isolating the piezoelectric elements from each other, the arrangement of trenches comprising at least two trenches extending alongside each other between adjacent piezoelectric elements for minimizing crosstalk between the piezoelectric elements of the array.

14. The device of claim 13, wherein the arrangement of trenches comprises two trenches that extend into the substrate from a first side of the substrate.

15. The device of claim 13, wherein the arrangement of trenches comprises two trenches that extend into the substrate respectively from first and second sides of the substrate.

16. The device of claim 13, wherein the arrangement of trenches comprises at least three trenches, wherein at least a first trench extends into the substrate from a first side of the substrate, and wherein at least a second trench extends into the substrate from a second side of the substrate.

17. The device of claim 13, wherein the at least two trenches extend in a non-intersecting pattern within the array.

18. The device of claim 13, wherein the at least two trenches are filled with air.

* * * * *